United States Patent
Pfister et al.

(10) Patent No.: US 11,921,105 B2
(45) Date of Patent: Mar. 5, 2024

(54) METHOD FOR IDENTIFYING POSITIVE ALLOSTERIC MODULATORS FOR ODORANT RECEPTORS

(71) Applicant: FIRMENICH SA, Satigny (CH)

(72) Inventors: Patrick Pfister, Plainsboro, NJ (US); Matthew Rogers, Plainsboro, NJ (US); Lily Wu, Plainsboro, NJ (US); Christian Margot, Satigny (CH)

(*) Notice: Subject to any disclaimer, the term of this patent is extended or adjusted under 35 U.S.C. 154(b) by 423 days.

(21) Appl. No.: 16/639,307

(22) PCT Filed: Dec. 20, 2018

(86) PCT No.: PCT/EP2018/086388
§ 371 (c)(1),
(2) Date: Feb. 14, 2020

(87) PCT Pub. No.: WO2019/122236
PCT Pub. Date: Jun. 27, 2019

(65) Prior Publication Data
US 2020/0408738 A1 Dec. 31, 2020

Related U.S. Application Data

(60) Provisional application No. 62/781,796, filed on Dec. 19, 2018, provisional application No. 62/609,017, filed on Dec. 21, 2017, provisional application No. 62/609,004, filed on Dec. 21, 2017.

(30) Foreign Application Priority Data

Feb. 20, 2018 (EP) .................................... 18157690
Apr. 11, 2018 (EP) .................................... 18166887

(51) Int. Cl.
*G01N 33/50* (2006.01)
(52) U.S. Cl.
CPC ..... *G01N 33/502* (2013.01); *G01N 2333/726* (2013.01)
(58) Field of Classification Search
CPC .................... G01N 33/502; G01N 2333/726
See application file for complete search history.

(56) References Cited

U.S. PATENT DOCUMENTS

2012/0015841 A1   1/2012   Shekdar et al.

FOREIGN PATENT DOCUMENTS

| CN | 105917228 A | 8/2016 | |
|----|----|----|----|
| JP | 2012516687 A | 7/2012 | |
| WO | 2014210585 A2 | 12/2014 | |
| WO | WO-2015020158 A1 * | 2/2015 | ........... G01N 33/566 |
| WO | 2016201152 A1 | 12/2016 | |

OTHER PUBLICATIONS

International Search Report and Written Opinion for corresponding International Application No. PCT/EP2018/086388, dated Mar. 8, 2019, 14 pages.
McClintock, T. S. et al., In Vivo Identification of Eugenol-Responsive and Muscone-Responsive Mouse Odorant Receptors, The Journal of Neuroscience, Nov. 19, 2014, vol. 34, No. 47, pp. 15669-15678.
Silva Teixeira, C. S. et al., Unravelling the Olfactory Sense: From the Gene to Odor Perception, Chemical Senses, Dec. 18, 2015, vol. 41, pp. 105-121.
Pronin, A. et al., Studies of Ectopically Expressed Olfactory Receptor Olfr558/PSGR2: Gene Expression, Function and Novel Molecular Probes, FASEB Journal, Apr. 1, 2016, vol. 30, No. 1_supplement, Abstract No. 709.7.
Sato-Akuhara, N. et al., Ligand Specificity and Evolution of Mammalian Musk Odor Receptors: Effect of Single Receptor Deletion on Odor Detection, The Journal of Neuroscience, Apr. 20, 2016, vol. 36, No. 16, pp. 4482-4491.
Tong, T. et al., Olfactory receptor 10J5 responding to α-cedrene regulates hepatic steatosis via the cAMP-PKA pathway, Scientific Reports, Aug. 25, 2017, vol. 7, No. 9471, pp. 1-13.
Araneda et al., "The molecular receptive range of an odorant receptor", Nature Neuroscience, Dec. 2000, pp. 1248-1255, 3(12).
May et al., "Allosteric Modulation of G Protein-Coupled Receptors", Annual Review of Pharmacology and Toxicology, 2007, pp. 1-51, 47(1).
Saito et al., "Odor Coding by a Mammalian Receptor Repertoire", Science Signaling, Nov. 6, 2009, pp. 1-28, 2 (60).

* cited by examiner

*Primary Examiner* — Ruixiang Li
(74) *Attorney, Agent, or Firm* — Armstrong Teasdale LLP

(57) ABSTRACT

The various aspects presented herein relate to the perfumery industry. More particularly, the various aspects presented herein relate to assays and methods for screening and identifying compositions and/or ingredients that intensify a subject's perception of target odorant compounds based on the use of particular olfactory receptors activated by the target odorant compound.

27 Claims, 22 Drawing Sheets
Specification includes a Sequence Listing.

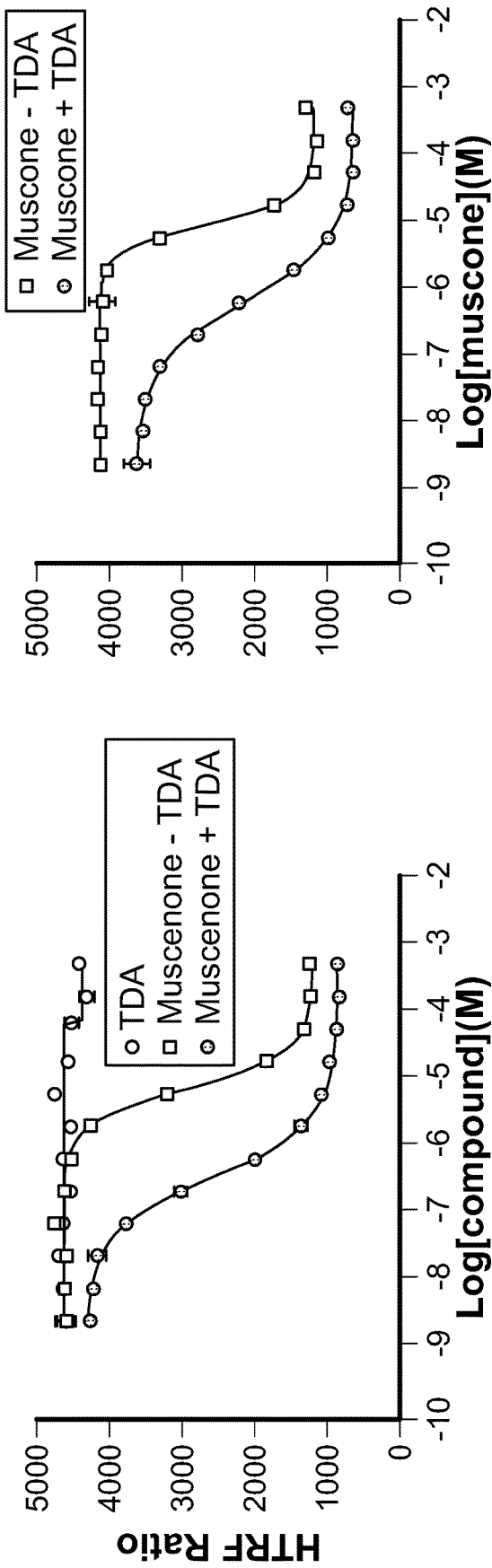
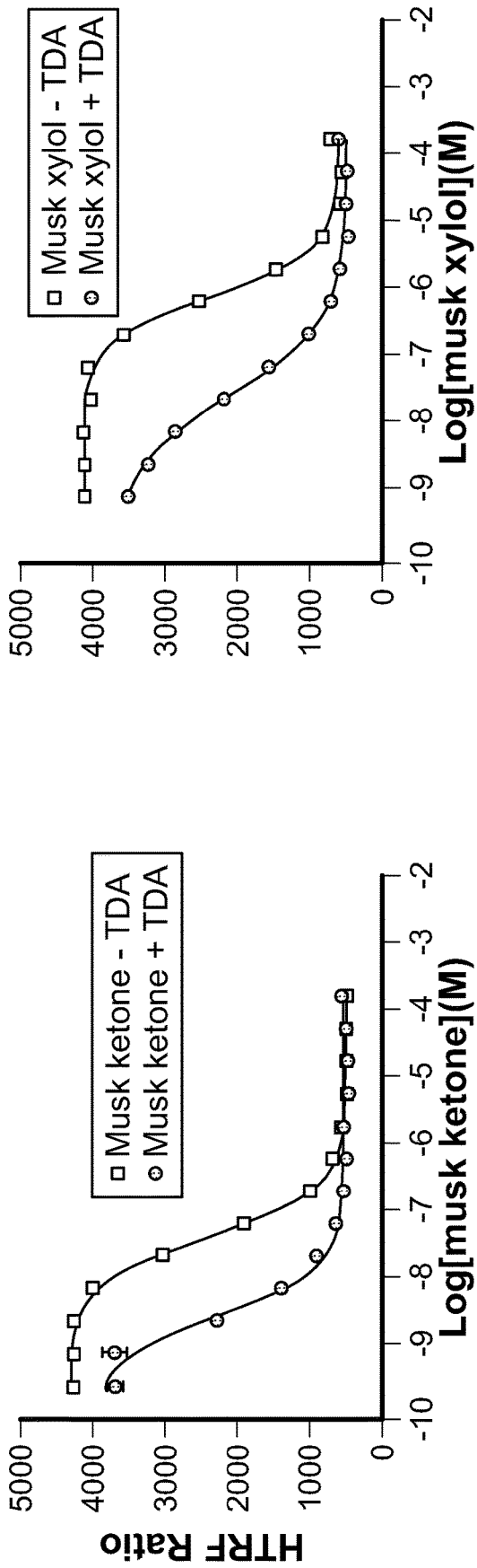

| Odorant Name | EC50 (uM) | | Fold shift |
|---|---|---|---|
| | -TDA | +TDA | |
| Muscenone | 7.6 | 0.4 | 21x |
| Muscone | 9.4 | 0.7 | 13x |
| Musk C | 0.05 | 0.003 | 16x |
| Musk X | 0.8 | 0.03 | 28x |

Figure 4

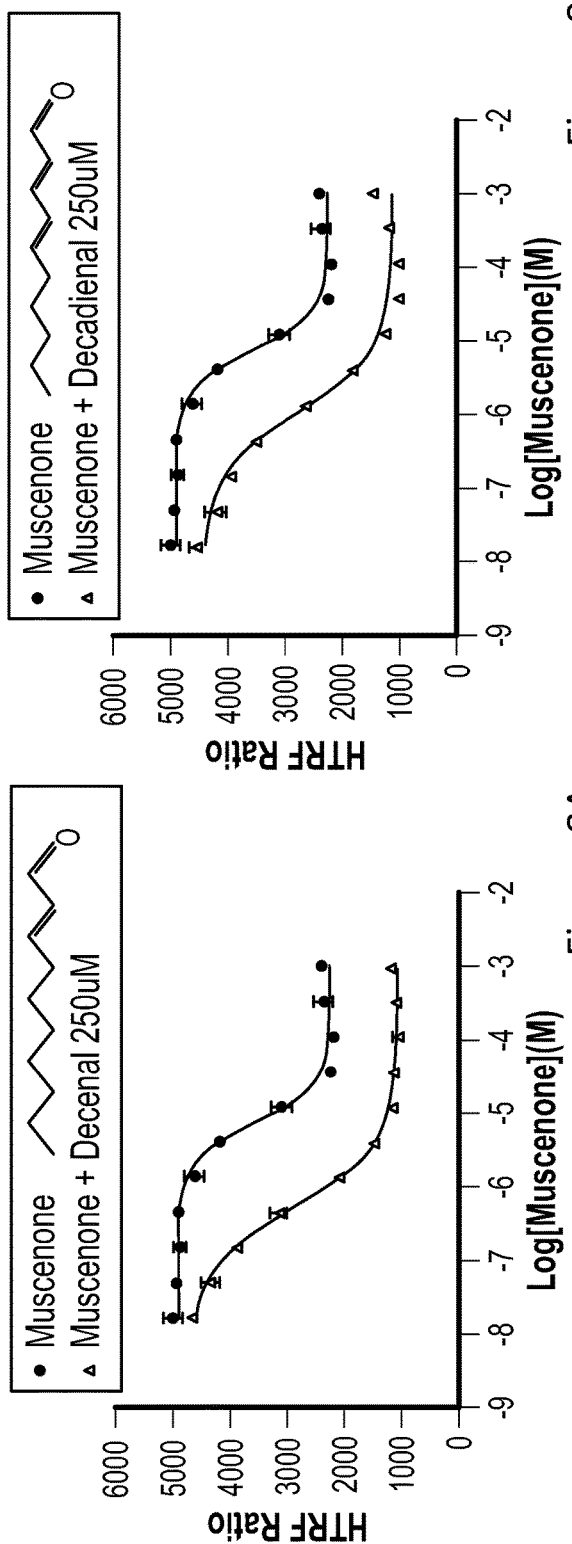
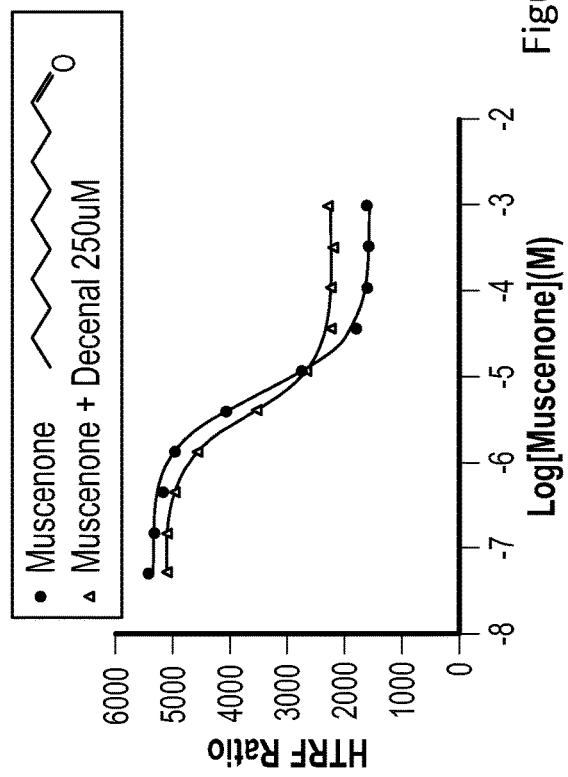
Figure 8A
Figure 8B
Figure 8C

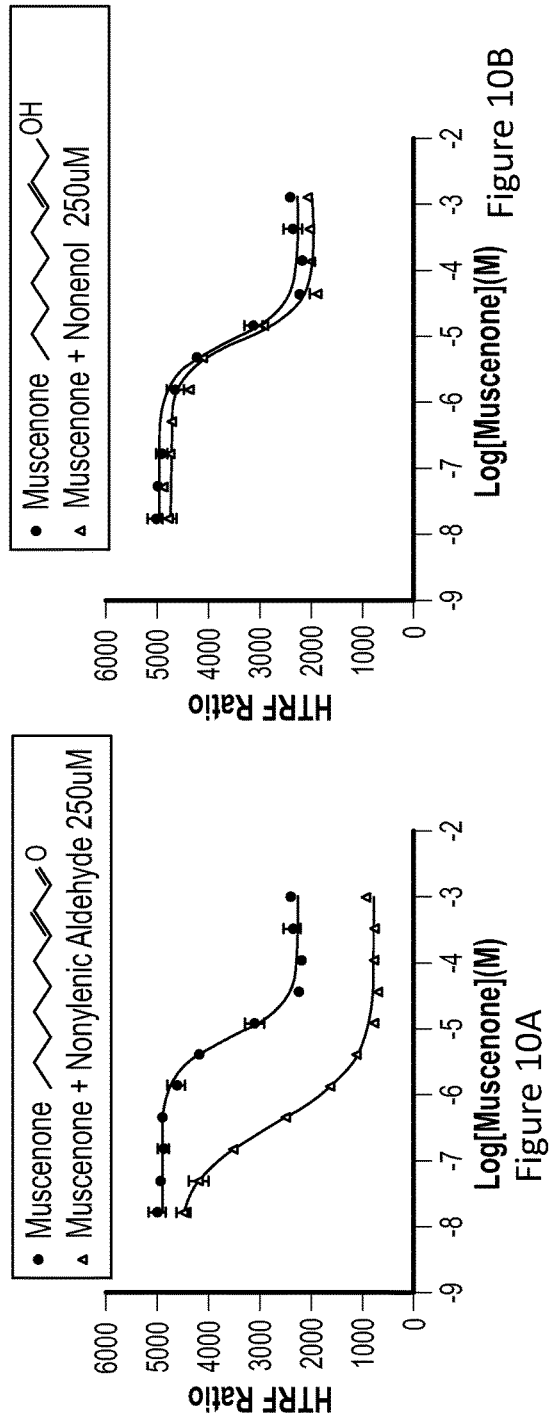
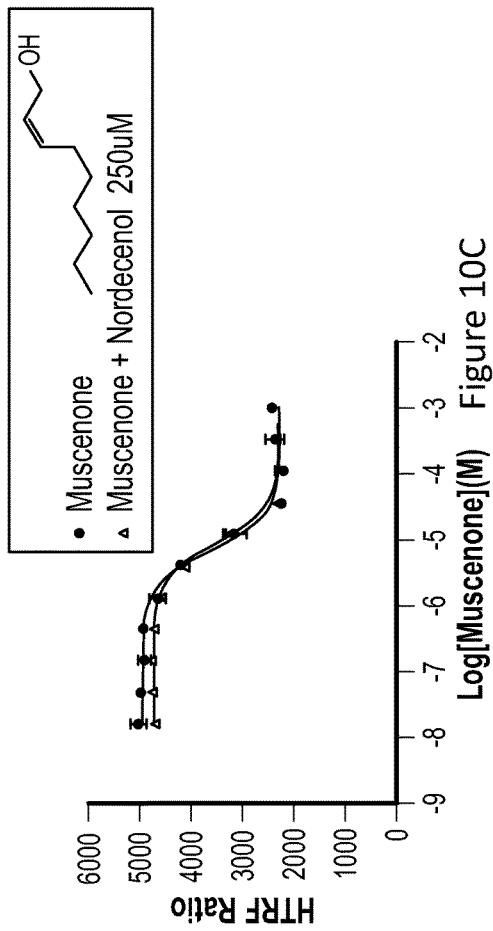
Figure 10A
Figure 10B
Figure 10C

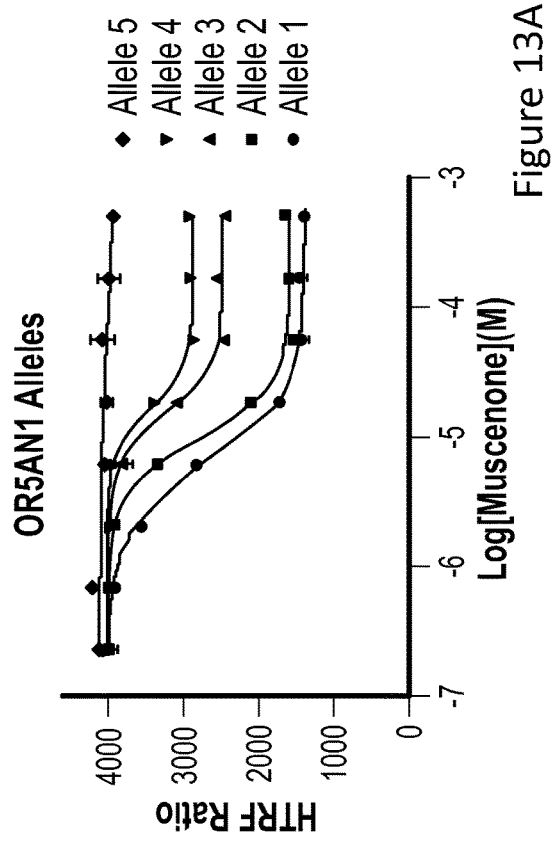
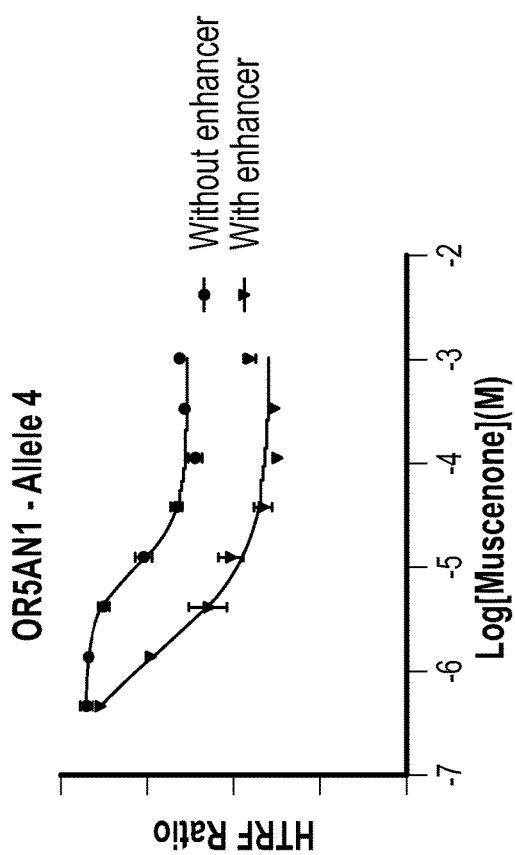
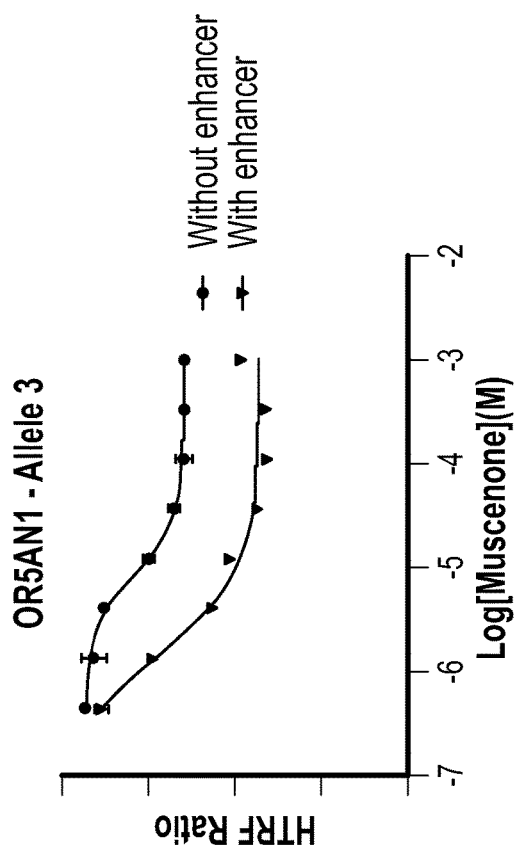
Figure 13A
Figure 13B
Figure 13C

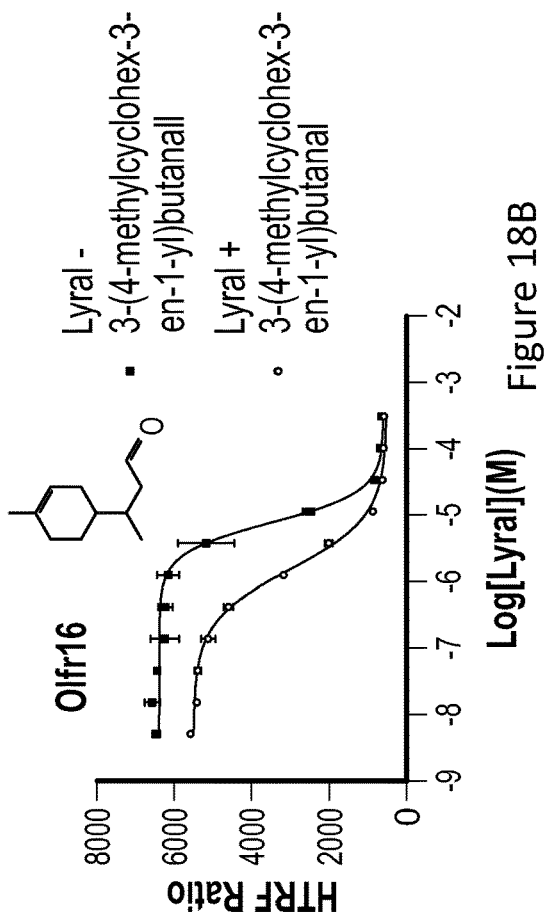
Figure 18A
Figure 18B
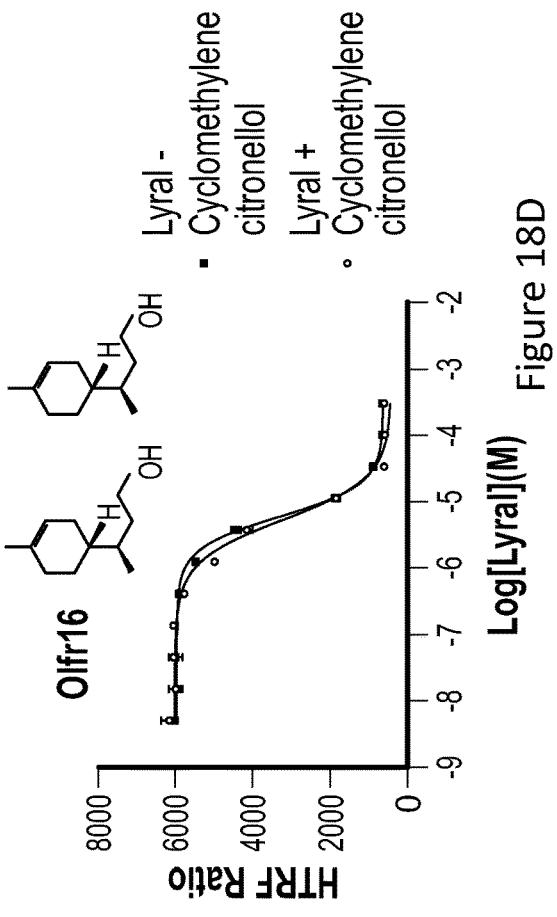
Figure 18C
Figure 18D

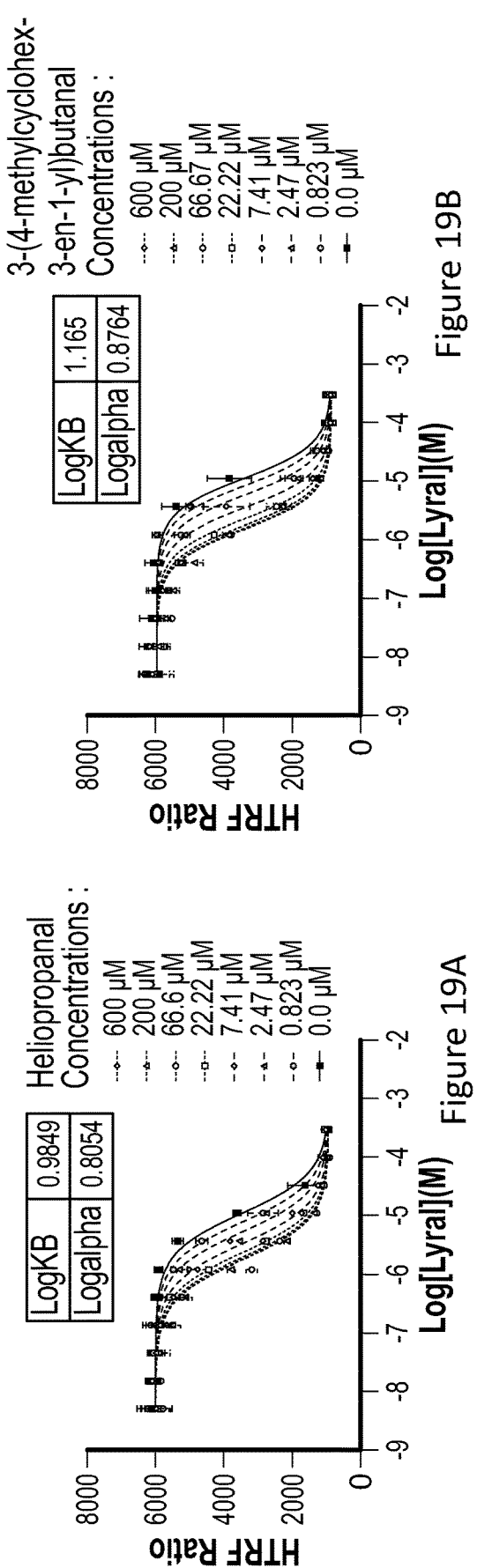
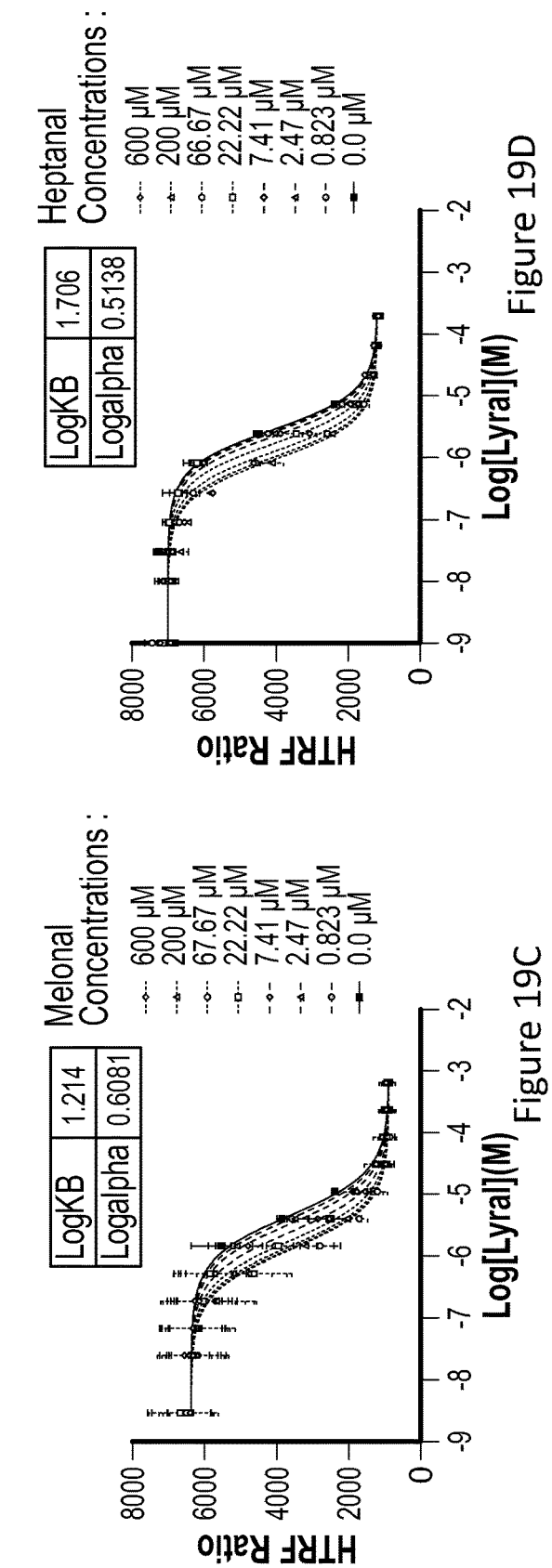
Figure 19A, Figure 19B, Figure 19C, Figure 19D

SEQUENCE LISTING

```
<160> NUMBER OF SEQ ID NOS: 17

<210> SEQ ID NO 1
<211> LENGTH: 937
<212> TYPE: DNA
<213> ORGANISM: Homo sapiens

<400> SEQUENCE: 1
atgactgggg gaggaaatat tacagaaatc acctatttca tcctgctggg attctcagat       60
tttcccagga tcataaaagt gctcttcact atattcctgg tgatctacat tacatctctg      120
gcctggaacc tctccctcat tgtttttaata aggatggatt cccacctcca tacacccatg     180
tatttcttcc tcagtaacct gtccttcata gatgtctgct atatcagctc cacagtcccc      240
aagatgctct ccaacctctt acaggaacag caaactatca cttttgttgg ttgtattatt      300
cagtacttta tcttttcaac gatgggactg agtgagtctt gtctcatgac agccatggct      360
tatgatcgtt atgctgccat ttgtaacccc ctgctctatt catccatcat gtcacccacc      420
ctctgtgttt ggatggtact gggagcctac atgactggcc tcactgcttc tttattccaa      480
attggtgctt tgcttcaact ccacttctgt gggtctaatg tcatcagaca tttcttctgt      540
gacatgcccc aactgttaat cttgtcctgt actgacactt tcttgtaca ggtcatgact       600 gctatattaa ccatgttctt tgggatagca agtgccctag ttatcatgat atcctatggc      660
tatattggca tctccatcat gaagatcact tcagctaaag gcaggtccaa ggcattcaac      720
acctgtgctt ctcatctaac agctgtttcc ctcttctata catcaggaat ctttgtctat      780
ttgagttcca gctctggagg ttcttcaagc tttgacagat ttgcatctgt tttctacact      840
gtggtcattc ccatgttaaa tcccttgatt tacagtttga ggaacaaaga aattaaagat      900
gccttaaaga ggttgcaaaa gagaaagtgc tgctgag                               937

<210> SEQ ID NO 2
<211> LENGTH: 311
<212> TYPE: PRT
<213> ORGANISM: Homo sapiens
```

<400> SEQUENCE: 2

Met Thr Gly Gly Gly Asn Ile Thr Glu Ile Thr Tyr Phe Ile Leu Leu
1               5                   10                  15
Gly Phe Ser Asp Phe Pro Arg Ile Ile Lys Val Leu Phe Thr Ile Phe
            20                  25                  30
Leu Val Ile Tyr Ile Thr Ser Leu Ala Trp Asn Leu Ser Leu Ile Val
        35                  40                  45
Leu Ile Arg Met Asp Ser His Leu His Thr Pro Met Tyr Phe Phe Leu
    50                  55                  60
Ser Asn Leu Ser Phe Ile Asp Val Cys Tyr Ile Ser Ser Thr Val Pro
65                  70                  75                  80
Lys Met Leu Ser Asn Leu Leu Gln Glu Gln Thr Ile Thr Phe Val
            85                  90                  95
Gly Cys Ile Ile Gln Tyr Phe Ile Phe Ser Thr Met Gly Leu Ser Glu
            100                 105                 110
Ser Cys Leu Met Thr Ala Met Ala Tyr Asp Arg Tyr Ala Ala Ile Cys
        115                 120                 125
Asn Pro Leu Leu Tyr Ser Ser Ile Met Ser Pro Thr Leu Cys Val Trp
    130                 135                 140
Met Val Leu Gly Ala Tyr Met Thr Gly Leu Thr Ala Ser Leu Phe Gln
145                 150                 155                 160
Ile Gly Ala Leu Leu Gln Leu His Phe Cys Gly Ser Asn Val Ile Arg
            165                 170                 175
His Phe Phe Cys Asp Met Pro Gln Leu Leu Ile Leu Ser Cys Thr Asp
            180                 185                 190
Thr Phe Phe Val Gln Val Met Thr Ala Ile Leu Thr Met Phe Phe Gly
        195                 200                 205
Ile Ala Ser Ala Leu Val Ile Met Ile Ser Tyr Gly Tyr Ile Gly Ile
    210                 215                 220
Ser Ile Met Lys Ile Thr Ser Ala Lys Gly Arg Ser Lys Ala Phe Asn
225                 230                 235                 240
Thr Cys Ala Ser His Leu Thr Ala Val Ser Leu Phe Tyr Thr Ser Gly
            245                 250                 255
Ile Phe Val Tyr Leu Ser Ser Ser Gly Gly Ser Ser Ser Phe Asp
            260                 265                 270
Arg Phe Ala Ser Val Phe Tyr Thr Val Val Ile Pro Met Leu Asn Pro
        275                 280                 285
Leu Ile Tyr Ser Leu Arg Asn Lys Glu Ile Lys Asp Ala Leu Lys Arg
    290                 295                 300
Leu Gln Lys Arg Lys Cys Cys
305                 310

<210> SEQ ID NO 3
<211> LENGTH: 930
<212> TYPE: DNA
<213> ORGANISM: Homo sapiens

<400> SEQUENCE: 3
atgaagagaa agaacttcac agaagtgtca gaattcattt tcttgggatt ttctagcttt      60
ggaaagcatc agataaccct ctttgtggtt ttcctaactg tctacatttt aactctggtt    120
gctaacatca tcattgtgac tatcatctgc attgaccatc atctccacac tcccatgtat    180
ttcttcctaa gcatgctggc tagttcagag acggtgtaca cactggtcat gtgccacga    240 atgcttttga gcctcatttt tcataaccaa cctatctcct ggcaggctg tgctacacaa    300

```
atgttctttt ttgttatctt ggccactaat aattgcttcc tgcttactgc aatggggtat    360
gaccgctatg tggccatctg cagacccctg agatacactg tcatcatgag caagggacta    420
tgtgcccagc tggtgtgtgg gtcctttggc attggtctga ctatggcagt tctccatgtg    480
acagccatgt tcaatttgcc gttctgtggc acagtggtag accacttctt ttgtgacatt    540
tacccagtca tgaaactttc ttgcattgat accactatca atgagataat aaattatggt    600
gtaagttcat ttgtgatttt tgtgcccata ggcctgatat ttatctccta tgtccttgtc    660
atctcttcca tccttcaaat tgcctcagct gagggctgga agaagacctt tgccacctgt    720
gtctcccacc tcactgtggt tattgtccac tgtggctgtg cctccattgc ctacctcaag    780
ccgaagtcag aaagttcaat agaaaaagac cttgttctct cagtgacgta caccatcatc    840
actcccttgc tgaaccctgt tgtttacagt ctgagaaaca aggaggtaaa ggatgccta     900 tgcagagttg tgggcagaaa tatttcttaa                                     930

<210> SEQ ID NO 4
<211> LENGTH: 309
<212> TYPE: PRT
<213> ORGANISM: Homo sapiens

<400> SEQUENCE: 4

Met Lys Arg Lys Asn Phe Thr Glu Val Ser Glu Phe Ile Phe Leu Gly
1               5                   10                  15

Phe Ser Ser Phe Gly Lys His Gln Ile Thr Leu Phe Val Val Phe Leu
            20                  25                  30

Thr Val Tyr Ile Leu Thr Leu Val Ala Asn Ile Ile Ile Val Thr Ile
        35                  40                  45

Ile Cys Ile Asp His His Leu His Thr Pro Met Tyr Phe Phe Leu Ser
    50                  55                  60

Met Leu Ala Ser Ser Glu Thr Val Tyr Thr Leu Val Ile Val Pro Arg
65                  70                  75                  80

Met Leu Leu Ser Leu Ile Phe His Asn Gln Pro Ile Ser Leu Ala Gly
                85                  90                  95

Cys Ala Thr Gln Met Phe Phe Val Ile Leu Ala Thr Asn Asn Cys
            100                 105                 110

Phe Leu Leu Thr Ala Met Gly Tyr Asp Arg Tyr Val Ala Ile Cys Arg
        115                 120                 125

Pro Leu Arg Tyr Thr Val Ile Met Ser Lys Gly Leu Cys Ala Gln Leu
    130                 135                 140

Val Cys Gly Ser Phe Gly Ile Gly Leu Thr Met Ala Val Leu His Val
145                 150                 155                 160

Thr Ala Met Phe Asn Leu Pro Phe Cys Gly Thr Val Val Asp His Phe
                165                 170                 175

Phe Cys Asp Ile Tyr Pro Val Met Lys Leu Ser Cys Ile Asp Thr Thr
            180                 185                 190

Ile Asn Glu Ile Ile Asn Tyr Gly Val Ser Ser Phe Val Ile Phe Val
        195                 200                 205

Pro Ile Gly Leu Ile Phe Ile Ser Tyr Val Leu Val Ile Ser Ser Ile
    210                 215                 220

Leu Gln Ile Ala Ser Ala Glu Gly Trp Lys Lys Thr Phe Ala Thr Cys
225                 230                 235                 240

Val Ser His Leu Thr Val Val Ile Val His Cys Gly Cys Ala Ser Ile
                245                 250                 255
```

```
Ala Tyr Leu Lys Pro Lys Ser Glu Ser Ser Ile Glu Lys Asp Leu Val
            260                 265                 270

Leu Ser Val Thr Tyr Thr Ile Ile Thr Pro Leu Leu Asn Pro Val Val
        275                 280                 285

Tyr Ser Leu Arg Asn Lys Glu Val Lys Asp Ala Leu Cys Arg Val Val
        290                 295                 300

Gly Arg Asn Ile Ser
305

<210> SEQ ID NO 5
<211> LENGTH: 948
<212> TYPE: DNA
<213> ORGANISM: Mus musculus

<400> SEQUENCE: 5
atgcctggag ggaggaatag cacagtcatc accaagttca tccttgtggg attctcagat    60
tttccaaagc tcaagctggt tctctttgtt atcttcctgg aagttatct ctccacagtg   120 gtgtggaact tgggcctcat catccttgatt aggattgacc cttacctaca cacacctatg  180
tacttcttcc tcagcaattt gtcattttta gatttctgtt acatttcatc tacaaccccct 240 aaaatgctct cgggattctt ccagaagtct aaatctatct cctttgttgg gtgcaccatg  300
cagtacttca tcttctcaag cctgggtctg tccgaatgct gccttctggc agccatggct  360
tatgaccggt atgctgccat tgtaatcct cttctctaca cagccatcat gtccccgtca   420
ctctgtgtgc acatggtggt tggagcctat agtactggtc tcttgggttc attgattcaa  480
ctgtgtgcta tacttcagct ccatttctgt gggccaaata ttataaacca tttcttttgt  540
gacctgcctc agctattagt tctttcctgc tctgaaacct ttccctgca agtcttgaaa  600 tttgtaatag cagtgatttt tggggtggca tctgtcattg ttatcctgat atcctatggt  660
tatatcattg cacaatcct gaatatcagc tcagtagaag taggtccaa ggcattcaat   720 acctgtgcct ctcacctgac agcagtcacc ctcttttttg gatcaggact ctttgtctat  780
atgcgcccca gctccaacag ttcccagggt tatgacaaga tggcttccgt gttctataca  840
gtggtgattc ccatgttgaa tcctctgatt tatagtctca ggaacaagga aataaaagat  900
gctcttcaga gatgtaaaaa taagtgcttt tctcagtgcc actgttag             948

<210> SEQ ID NO 6
<211> LENGTH: 315
<212> TYPE: PRT
<213> ORGANISM: Mus musculus

<400> SEQUENCE: 6

Met Pro Gly Gly Arg Asn Ser Thr Val Ile Thr Lys Phe Ile Leu Val
1               5                   10                  15

Gly Phe Ser Asp Phe Pro Lys Leu Lys Leu Val Leu Phe Val Ile Phe
            20                  25                  30

Leu Gly Ser Tyr Leu Ser Thr Val Val Trp Asn Leu Gly Leu Ile Ile
        35                  40                  45

Leu Ile Arg Ile Asp Pro Tyr Leu His Thr Pro Met Tyr Phe Phe Leu
    50                  55                  60

Ser Asn Leu Ser Phe Leu Asp Phe Cys Tyr Ile Ser Ser Thr Thr Pro
65                  70                  75                  80

Lys Met Leu Ser Gly Phe Phe Gln Lys Ser Lys Ser Ile Ser Phe Val
                85                  90                  95

Gly Cys Thr Met Gln Tyr Phe Ile Phe Ser Ser Leu Gly Leu Ser Glu
```

```
            100                 105                 110
Cys Cys Leu Leu Ala Ala Met Ala Tyr Asp Arg Tyr Ala Ala Ile Cys
        115                 120                 125

Asn Pro Leu Leu Tyr Thr Ala Ile Met Ser Pro Ser Leu Cys Val His
    130                 135                 140

Met Val Val Gly Ala Tyr Ser Thr Gly Leu Leu Gly Ser Leu Ile Gln
145                 150                 155                 160

Leu Cys Ala Ile Leu Gln Leu His Phe Cys Gly Pro Asn Ile Ile Asn
                165                 170                 175

His Phe Phe Cys Asp Leu Pro Gln Leu Leu Val Leu Ser Cys Ser Glu
            180                 185                 190

Thr Phe Pro Leu Gln Val Leu Lys Phe Val Ile Ala Val Ile Phe Gly
        195                 200                 205

Val Ala Ser Val Ile Val Ile Leu Ile Ser Tyr Gly Tyr Ile Ile Gly
    210                 215                 220

Thr Ile Leu Asn Ile Ser Ser Val Glu Gly Arg Ser Lys Ala Phe Asn
225                 230                 235                 240

Thr Cys Ala Ser His Leu Thr Ala Val Thr Leu Phe Phe Gly Ser Gly
                245                 250                 255

Leu Phe Val Tyr Met Arg Pro Ser Ser Asn Ser Ser Gln Gly Tyr Asp
            260                 265                 270

Lys Met Ala Ser Val Phe Tyr Thr Val Val Ile Pro Met Leu Asn Pro
        275                 280                 285

Leu Ile Tyr Ser Leu Arg Asn Lys Glu Ile Lys Asp Ala Leu Gln Arg
    290                 295                 300

Cys Lys Asn Lys Cys Phe Ser Gln Cys His Cys
305                 310                 315

<210> SEQ ID NO 7
<211> LENGTH: 930
<212> TYPE: DNA
<213> ORGANISM: Mus musculus

<400> SEQUENCE: 7
atgcagagaa ataacttcac tgaagtgata gagttcgtct tcctgggatt ctccagcttt      60
ggaaagcatc agataaccct ctttgtggtt ttcctaacca tctacatttt aactctggct     120
ggcaacatca ttatagtgac aatcacacac atagaccacc accttcacac tcccatgtac     180
ttctttctga gcatgttggc aagctcagag actgtgtaca cactggtcat tgtcccacga     240
atgctttcca gcctgatttt ttacaacctt cccatatcct tggcaggctg cgcaacccaa     300
atgttctttt ttgtcacctt ggccaccaac aactgctttc tgctcacagc aatgggttat     360
gatcgttatg tggctatttg taatcctctg agatatacaa tcatcatgag caagggaatg     420
tgtgccttgt tggtttgtgg gtctttaggc actggcctgg ttatggcagt tcttcatgtg     480
ccagccatgt ccatttgcc cttttgtggc acggtggtgg agcactttt ctgtgacata     540 tacccagtaa tgaagctttc ttgtgttgat accactgtca atgagataat caattatggt     600
gtaagttcat ttgtaattct tgtgcccata gggctgatat ttatctccta tgtgctcatt     660
gtctcttcca tccttaaaat tgtgtccact gaaggccaga agaaagcctt tgccacctgt     720
gcctctcatc tcactgtggt cattgtccac tatggctgtg cctccattgc ctacctcaaa     780
cccaaatcag aaagttcagt agaaaaagac cttcttctct ctgtgaccta cactatcatc     840
actcccttgc tgaaccctgt tgtctacagc ctcaggaaca aagaagtcaa agatgctcta     900
```
tgcagagctg tgggcagaaa cacttcttaa                                        930

<210> SEQ ID NO 8
<211> LENGTH: 309
<212> TYPE: PRT
<213> ORGANISM: Mus musculus

<400> SEQUENCE: 8

Met Gln Arg Asn Asn Phe Thr Glu Val Ile Glu Phe Val Phe Leu Gly
1               5                   10                  15

Phe Ser Ser Phe Gly Lys His Gln Ile Thr Leu Phe Val Val Phe Leu
            20                  25                  30

Thr Ile Tyr Ile Leu Thr Leu Ala Gly Asn Ile Ile Ile Val Thr Ile
        35                  40                  45

Thr His Ile Asp His His Leu His Thr Pro Met Tyr Phe Phe Leu Ser
    50                  55                  60

Met Leu Ala Ser Ser Glu Thr Val Tyr Thr Leu Val Ile Val Pro Arg
65                  70                  75                  80

Met Leu Ser Ser Leu Ile Phe Tyr Asn Leu Pro Ile Ser Leu Ala Gly
                85                  90                  95

Cys Ala Thr Gln Met Phe Phe Val Thr Leu Ala Thr Asn Asn Cys
            100                 105                 110

Phe Leu Leu Thr Ala Met Gly Tyr Asp Arg Tyr Val Ala Ile Cys Asn
        115                 120                 125

Pro Leu Arg Tyr Thr Ile Ile Met Ser Lys Gly Met Cys Ala Leu Leu
    130                 135                 140

Val Cys Gly Ser Leu Gly Thr Gly Leu Val Met Ala Val Leu His Val
145                 150                 155                 160

Pro Ala Met Phe His Leu Pro Phe Cys Gly Thr Val Val Glu His Phe
                165                 170                 175

Phe Cys Asp Ile Tyr Pro Val Met Lys Leu Ser Cys Val Asp Thr Thr
            180                 185                 190

Val Asn Glu Ile Ile Asn Tyr Gly Val Ser Ser Phe Val Ile Leu Val
        195                 200                 205

Pro Ile Gly Leu Ile Phe Ile Ser Tyr Val Leu Ile Val Ser Ser Ile
    210                 215                 220

Leu Lys Ile Val Ser Thr Glu Gly Gln Lys Lys Ala Phe Ala Thr Cys
225                 230                 235                 240

Ala Ser His Leu Thr Val Val Ile Val His Tyr Gly Cys Ala Ser Ile
                245                 250                 255

Ala Tyr Leu Lys Pro Lys Ser Glu Ser Val Glu Lys Asp Leu Leu
            260                 265                 270

Leu Ser Val Thr Tyr Thr Ile Ile Thr Pro Leu Leu Asn Pro Val Val
        275                 280                 285

Tyr Ser Leu Arg Asn Lys Glu Val Lys Asp Ala Leu Cys Arg Ala Val
    290                 295                 300

Gly Arg Asn Thr Ser
305

<210> SEQ ID NO 9
<211> LENGTH: 24
<212> TYPE: DNA
<213> ORGANISM: Artificial Sequence
<220> FEATURE:
<223> OTHER INFORMATION: FLAG tag

<400> SEQUENCE: 9

```
gattacaagg acgacgacga taag                                        24

<210> SEQ ID NO 10
<211> LENGTH: 8
<212> TYPE: PRT
<213> ORGANISM: Artificial Sequence
<220> FEATURE:
<223> OTHER INFORMATION: FLAG tag

<400> SEQUENCE: 10

Asp Tyr Lys Asp Asp Asp Asp Lys
1               5

<210> SEQ ID NO 11
<211> LENGTH: 60
<212> TYPE: DNA
<213> ORGANISM: Artificial Sequence
<220> FEATURE:
<223> OTHER INFORMATION: Rho tag

<400> SEQUENCE: 11
atgaacggga ccgagggccc aaacttctac gtgcctttct ccaacaagac gggcgtggtg   60

<210> SEQ ID NO 12
<211> LENGTH: 20
<212> TYPE: PRT
<213> ORGANISM: Artificial Sequence
<220> FEATURE:
<223> OTHER INFORMATION: Rho tag

<400> SEQUENCE: 12

Met Asn Gly Thr Glu Gly Pro Asn Phe Tyr Val Pro Phe Ser Asn Lys
1               5                   10                  15

Thr Gly Val Val
            20

<210> SEQ ID NO 13
<211> LENGTH: 51
<212> TYPE: DNA
<213> ORGANISM: Artificial Sequence
<220> FEATURE:
<223> OTHER INFORMATION: Lucy tag

<400> SEQUENCE: 13
atgagacccc agatcctgct gctcctggcc ctgctgaccc taggcctggc t             51

<210> SEQ ID NO 14
<211> LENGTH: 17
<212> TYPE: PRT
<213> ORGANISM: Artificial Sequence
<220> FEATURE:
<223> OTHER INFORMATION: Lucy tag

<400> SEQUENCE: 14

Met Arg Pro Gln Ile Leu Leu Leu Leu Ala Leu Leu Thr Leu Gly Leu
1               5                   10                  15

Ala

<210> SEQ ID NO 15
<211> LENGTH: 10
<212> TYPE: PRT
<213> ORGANISM: Artificial Sequence
<220> FEATURE:
<223> OTHER INFORMATION: Motif
```

```
<400> SEQUENCE: 15

Met Ala Tyr Asp Arg Tyr Val Ala Ile Cys
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Motif

<400> SEQUENCE: 16

Phe Ser Thr Cys Ser Ser His
1               5

<210> SEQ ID NO 17
<211> LENGTH: 8
<212> TYPE: PRT
<213> ORGANISM: Artificial Sequence
<220> FEATURE:
<223> OTHER INFORMATION: Motif

<400> SEQUENCE: 17

Pro Met Leu Asn Pro Phe Ile Tyr
1               5
```

METHOD FOR IDENTIFYING POSITIVE ALLOSTERIC MODULATORS FOR ODORANT RECEPTORS

CROSS-REFERENCE TO RELATED APPLICATIONS

This application is a U.S. National Phase Applications of PCT/EP2018/086388, filed Dec. 20, 2018, which claims priority to U.S. Provisional Patent Application Ser. No. 62/609,004, filed on Dec. 21, 2017, to U.S. Provisional Patent Application Ser. No. 62/609,017, filed on Dec. 21, 2017, to U.S. Provisional Patent Application Ser. No. 62/781,796, filed on Dec. 19, 2018, to European Patent Application Serial No. 18157690.1, filed on Feb. 20, 2018, and to European Patent Application Serial No. 18166887.2, filed on Apr. 11, 2018, the entire contents of which are hereby incorporated by reference in their entirety.

FIELD OF THE INVENTION

The technical field is directed to odorant and aroma receptors and assays that can be used to identify odorant and/or aroma compounds and more specifically positive modulators of human odorant receptor activity.

BACKGROUND

Olfaction is one of the most complex and poorly understood of human sensory systems. From olfactory receptor (OR) activation to perception, there are many steps that still require further investigation. If we can understand how the OR code for individual odorants and mixtures translates into perception then we can exploit this knowledge to bring significant benefit in several areas. These areas include odor modulators like malodor counteractants that block the perception of unpleasant odors, new flavor and fragrance ingredients that replace non-biodegradable or toxic compounds, and odorant enhancers that would limit our reliance on difficult to source compounds from natural sources or that would improve the sensitivity to certain fragrance ingredients. The 'olfactory receptor code' combinatorial paradigm is centered on the observation that any single OR may be activated by multiple odorants, and conversely most odorants are capable of activating several ORs. In the mouse genome there are approximately 1,200 distinct intact ORs. Humans, by contrast, have approximately 400. In both cases, the repertoire of ORs is activated by many thousands of odorants in the world, and it is this combinatorial complexity that allows for the breadth of olfactory sensations we can perceive. However, odorants or ligands for only 48 human ORs (approximately 12%) have been identified as of 2016 using traditional deorphanization methods [Teixeira C. S. S. et al., Chemical Senses, 41(2):105-21 (2016)]. In addition, the physiological relevance of most ligands for the human ORs, essentially identified in vitro, has not been tested.

A method that can rapidly and reliably identify a relatively small subset of ORs, within the entire repertoire of ORs that exist in an organism that are specifically activated or inhibited by one or more odorants is described in WO2014/210585.

Because ORs are encoded by the largest gene family in vertebrates, i.e. seven transmembrane Class A G-protein-coupled receptors (GPCRs), identification of receptors that are elemental to a given percept is difficult.

There remains a need to identify ORs receptors that are activated by particular odorant and/or aroma compounds. Once one or more ORs are identified that are activated by a particular odorant and/or aroma compound or group of such compounds, there remains a need to identify relevant odorant receptors that can be used in assays and methods to identify and pharmacologically characterize volatile modulators of OR activity such as allosteric modulators. Such allosteric modulation of an odorant receptor activity was at best speculative and eluded the field of olfaction.

Thus, methods for identifying relevant receptors and compounds that can be used in perfumery or other applications to modulate, improve, or enhance (using positive allosteric modulators) desired fragrances or aromas which can lead to more sensitive and more intense perception of perfumery or aroma tonalities or inhibit or counteract (using negative allosteric modulators or competitive antagonists) unwanted smells or compounds are desired.

SUMMARY

One aspect presented herein provides a high-throughput assay system for identifying one or more compounds from a group of compounds wherein the one or more compounds positively modulates the activity of an olfactory receptor induced by an agonist odorant compound, comprising:
  a. one or more isolated cells, each cell expressing one mammalian olfactory receptor, wherein the one or more cells comprises a target olfactory receptor that is activated by one or more odorant,
  b. a first compound that binds to the olfactory receptor and that activates the olfactory receptor, and
  c. at least one second compound that binds to the receptor non-competitively relative to the first compound and that enhances the activity of the receptor exposed to the first compound when compared to the activity of the receptor exposed to the first compound in the absence of the second compound,
wherein the first compound is an agonist odorant compound of the olfactory receptor,
wherein the first compound and the second compound are different compounds,
wherein the second compound is not an agonist of the receptor, and
wherein the activity of the receptor is synergistically enhanced by the combination of the first compound and the second compound.

In one aspect, the at least one second compound is selected from a pool of compounds based on structure-activity relationship (SAR) analysis.

In one aspect, the second compound binds to a site on the olfactory receptor distinct from the site where the first compound binds.

In one aspect, the second compound is a positive allosteric modulating compound.

In one aspect of the assay or the methods herein, the olfactory receptor is selected from the group consisting of OR5AN1, Olfr1440, OR10J5, or Olfr16.

In one aspect of the assay or the methods herein, at least one of the olfactory receptors comprises a polypeptide
  a. comprises an amino acid sequence having at least 70% sequence identity to SEQ ID NO: 2, 4, 6, or 8; and/or
  b. is encoded by a nucleic acid molecule comprising a nucleotide sequence having at least 70% sequence identity to SEQ ID NO: 1, 3, 5, or 7, or the reverse complement thereof.

In one aspect, the at least one of the olfactory receptors comprises a polypeptide a. comprises an amino acid sequence having at least 90%, 95%, 98%, 99% or 100% sequence identity to SEQ ID NO: 2, 4, 6, or 8; and/or
b. is encoded by a nucleic acid molecule comprising a nucleotide sequence having at least 90%, 95%, 98%, 99% or 100% sequence identity to SEQ ID NO: 1, 3, 5, or 7, or the reverse complement thereof.

In one aspect of the assay or methods, the first compound is a musk or a floral muguet compound.

In one aspect, the mammalian olfactory receptor is a mouse olfactory receptor or a human olfactory receptor.

In one aspect, the first compound comprises a musk compound and the olfactory receptor is OR5AN1 or Olfr1440; chimera and functional fragments thereof; and wherein the olfactory receptor comprises a polypeptide that
a. comprises an amino acid sequence having at least 70% sequence identity to SEQ ID NO: 2 or 6; and/or
b. is encoded by a nucleic acid molecule comprising a nucleotide sequence having at least 70% sequence identity to SEQ ID NO: 1 or 5, or the reverse complement thereof.

In one aspect, the musk compound comprises a macrocyclic ketone or a nitromusk compound.

In one aspect, the receptor is OR5AN1, the agonist odorant compound comprises a macrocyclic ketone or a nitromusk compound; and the selected compound comprises at least one positive allosteric modulator having the structure:

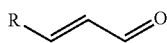

Formula (I)

in the form of any one of its stereoisomers or a mixture thereof,
wherein R represents a $C_{3-11}$ linear alkyl group optionally substituted by an $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, and wherein the compound of Formula (I) is a positive allosteric modulator of a musk olfactory receptor.

In another aspect, the compound of Formula (I) is selected from the group consisting of: (E,E)-2,4-decadienal, (E)-2-undecenal, (E,E)-2,4-nonadienal, (E)-2-tridecenal, (2E)-2-dodecenal, (2E,6Z)-2,6-nonadienal, (E,E)-2,6-nonadienal, (2E)-2,4-undecadienal, (2E)-2,4-dodecadienal, (E)-2-nonenal, (2E,4E,7Z)-decatrienal, (Z)-2-decenal, (E)-2-octenal, (E)-2-decenal, (Z)-4-(benzyloxy)but-2-enal, (E)-4-(benzyloxy)but-2-enal, (E)-4-cyclohexylidenebut-2-enal, (2E)-3-(4-methylphenyl)-2-propenal, (2E,5E)-6,10-dimethyl-2,5,9-undecatrienal, (2E)-7,8-dimethyl-2,7-nonadienal, methyl (5E)-7-oxo-5-heptenoate, (2E)-7-methyl-2,6-octadienal, (2E)-6,6-dimethyl-2-heptenal, (+−)-(2E)-5,9-dimethyl-2,8-decadienal, (E)-2-tetradecenal, and (E)-8-methoxy-4,8-dimethylnon-2-enal, and combinations thereof.

In another aspect, the first compound comprises a floral muguet compound and the olfactory receptor is OR10J5 or Olfr16; chimera and functional fragments thereof; and wherein the olfactory receptor comprises a polypeptide that
a. comprises an amino acid sequence having at least 70% sequence identity to SEQ ID NO: 4 or 8; and/or
b. is encoded by a nucleic acid molecule comprising a nucleotide sequence having at least 70% sequence identity to SEQ ID NO: 3 or 7, or the reverse complement thereof.

In one aspect, the floral muguet compound is 3-(4-hydroxy-4-methylpentyl)cyclohex-3-ene-1-carbaldehyde, 4-(4-hydroxy-4-methylpentyl)cyclohex-3-ene-1-carbaldehyde or a mixture thereof.

In one aspect, the receptor is OR10J5, the agonist odorant compound comprises a floral muguet compound; and the selected compound comprises at least one positive allosteric modulator selected from the group consisting of octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

In one aspect, the modulated activity comprises
a. modulating the binding affinity of the first compound to the orthosteric site,
b. modulating the binding activation efficacy of the first compound to the orthosteric site, and/or
c. modulating the G-protein binding site.

One aspect presented herein provides a method for identifying at least one positive allosteric modulating compound that enhances the activity of an olfactory receptor in the presence of an agonist of the receptor, comprising
a. providing one or more isolated cells, each cell expressing one mammalian olfactory receptor,
b. exposing the one or more cells to a first compound that activates the olfactory receptor,
c. exposing the one or more cells to one or more test compound, and
d. selecting at least one second compound from the one or more test compounds when the at least one second compound in combination with the first compound has a synergistic effect on the receptor activity as a positive allosteric modulating compound;

wherein the first compound is an agonist odorant compound of the olfactory receptor,
wherein the first compound and the second compound are different compounds, and
wherein the second compound is not an agonist of the receptor.

In one aspect, the activation of the olfactory receptor to the first compound is measured by measuring the response of said olfactory receptor in the presence and absence of the first compound.

In one aspect, the at least one second compound is selected from one or more test compounds from a chemically diverse compound library.

In one aspect, the at least one second compound is selected from one or more test compounds based on structure-activity relationship (SAR) analysis of the compounds identified initially.

The method of any one of the preceding aspects, wherein the second compound binds to a site on the olfactory receptor distinct from the site where the first compound binds.

In one aspect, prior to step a) of the assay system or the method provided herein, the one or more cells is transformed to express the target olfactory receptor.

In one aspect, the olfactory receptor is heterologous to the one or more cells.

In one aspect, the cell is selected from the group consisting of HEK293, CHO, Xenopus oocytes, COS, S2, Sf9, insect, yeast and cells derived from the olfactory placode.

One aspect presented herein provides a method for identifying a compound that enhances the activity of an olfactory receptor induced by an agonist odorant compound comprising:
(i) screening one or more compounds in a binding assay in the presence of the agonist odorant compound;
(ii) selecting one or more of the compounds screened that specifically enhances the specific binding or the effect of the binding of an agonist odorant compound to a mammalian olfactory receptor; and
(iii) identifying compounds that potentially modulate the perception of the agonist odorant compound based on their enhancement of the specific binding or the effect of the binding of the agonist odorant compound to the olfactory receptor.

In one aspect, the enhancement of the effect of the binding of the agonist odorant compound to the olfactory receptor comprises enhancing the potency and/or efficacy of the activity of the receptor compared to the activity of the receptor in the absence of the selected compound.

In one aspect, select compounds that enhance the potency and/or efficacy of the activity of the receptor compared to the activity of the receptor in the absence of the selected compound can covalently bind to the target receptor.

In one aspect, the receptor is OR5AN1, the agonist odorant compound comprises a musk compound; and the selected compound is a positive allosteric modulator comprising a positive allosteric modulator having the structure:

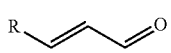

Formula (I)

in the form of any one of its stereoisomers or a mixture thereof,
wherein R represents a $C_{3-11}$ linear alkyl group optionally substituted by an $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, and wherein the compound of Formula (I) is a positive allosteric modulator of a musk olfactory receptor.

In one aspect, the compound of Formula (I) is selected from the group consisting of: (E,E)-2,4-decadienal, (E)-2-undecenal, (E,E)-2,4-nonadienal, (E)-2-tridecenal, (2E)-2-dodecenal, (2E,6Z)-2,6-nonadienal, (E,E)-2,6-nonadienal, (2E)-2,4-undecadienal, (2E)-2,4-dodecadienal, (E)-2-nonenal, (2E,4E,7Z)-decatrienal, (Z)-2-decenal, (E)-2-octenal, (E)-2-decenal, (Z)-4-(benzyloxy)but-2-enal, (E)-4-(benzyloxy)but-2-enal, (E)-4-cyclohexylidenebut-2-enal, (2E)-3-(4-methylphenyl)-2-propenal, (2E,5E)-6,10-dimethyl-2,5,9-undecatrienal, (2E)-7,8-dimethyl-2,7-nonadienal, methyl (5E)-7-oxo-5-heptenoate, (2E)-7-methyl-2,6-octadienal, (2E)-6,6-dimethyl-2-heptenal, (+−)-(2E)-5,9-dimethyl-2,8-decadienal, (E)-2-tetradecenal, and (E)-8-methoxy-4,8-dimethylnon-2-enal.

In one aspect, the receptor is OR10J5, the agonist odorant compound comprises a floral muguet compound; and the selected compound comprises at least one positive allosteric modulator selected from the group consisting of octanal; (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

In one aspect, the one or more selected compound is selected based on structure-activity relationship (SAR) analysis specifically designed to identify the chemical determinants of putative enhancement.

In one aspect, the screening comprises calculating an activation window to confirm the statistical quality of the data and to measure the synergistic effect enhancement at $EC_{05-50}$, and in another aspect at $EC_{20}$.

One aspect presented herein provides a use of a polypeptide that can be activated by an agonist, the polypeptide selected from a human olfactory receptor that is activated by the agonist for use in a screening assay for identifying one or more positive allosteric modulating compound of the agonist.

One aspect presented herein provides a use of a polypeptide that can be activated by a musk, comprising an amino acid sequence having at least 70%, 75%, 80%, 85%, 90%, 95%, 96%, 97%, 98%, 99%, or 100% sequence identity to SEQ ID NO: 2 or 6 for identifying a positive allosteric modulating compound of musk.

One aspect presented herein provides a use of a polypeptide that can be activated by a floral muguet compound, comprising an amino acid sequence having at least 70%, 75%, 80%, 85%, 90%, 95%, 96%, 97%, 98%, 99%, or 100% sequence identity to SEQ ID NO: 4 or 8 for identifying a positive allosteric modulating compound of the floral muguet receptor activity.

BRIEF DESCRIPTION OF THE FIGURES

FIG. 3 shows the dose response curves of OR5AN1 to all four of agonist muscone, MUSCENONE®, musk xylol and musk ketone in the presence and absence of tridecylenic aldehyde, and a dose-response to tridecylenic aldehyde alone.

FIG. 4 gives the $EC_{50}$ values obtained from the dose response curves obtained in FIG. 3 and summarizes the corresponding the EC50 fold shift.

FIG. 8 shows the distinct enhancement levels obtained on OR5AN1 with a) decenal, b) decadienal and c) decanal, and the requirement of the unsaturation.

FIG. 10 shows the distinct enhancement levels obtained on OR5AN1 with a) nonylenic aldehyde, b) nonenol and c) nordecenol, and the absence of enhancement with an alcohol functional group.

FIG. 13 shows OR5AN1 alleles are not functionally equivalent when activated with MUSCENONE® but enhancement restores activity of hypofunctional alleles.

FIG. 18 shows the distinct enhancement levels obtained on Olfr16 LYRAL®-induced activation with a) heliopropanal, b) 3-(4-methylcyclohex-3-en-1-yl)butanal, c) heliotropine and d) cyclomethylene citronellol, and the absence of enhancement for the latter two compounds.

FIG. 19 displays a series of dose response curves of OR10J5 to LYRAL® in the presence of serial concentrations of a) heliopropanal, b) 3-(4-methylcyclohex-3-en-1-yl)butanal, c) melonal and d) heptanal, and also indicates the corresponding calculated log values for the cooperativity factor α and the equilibrium constant KB.

DETAILED DESCRIPTION

Definitions

Figure 1:
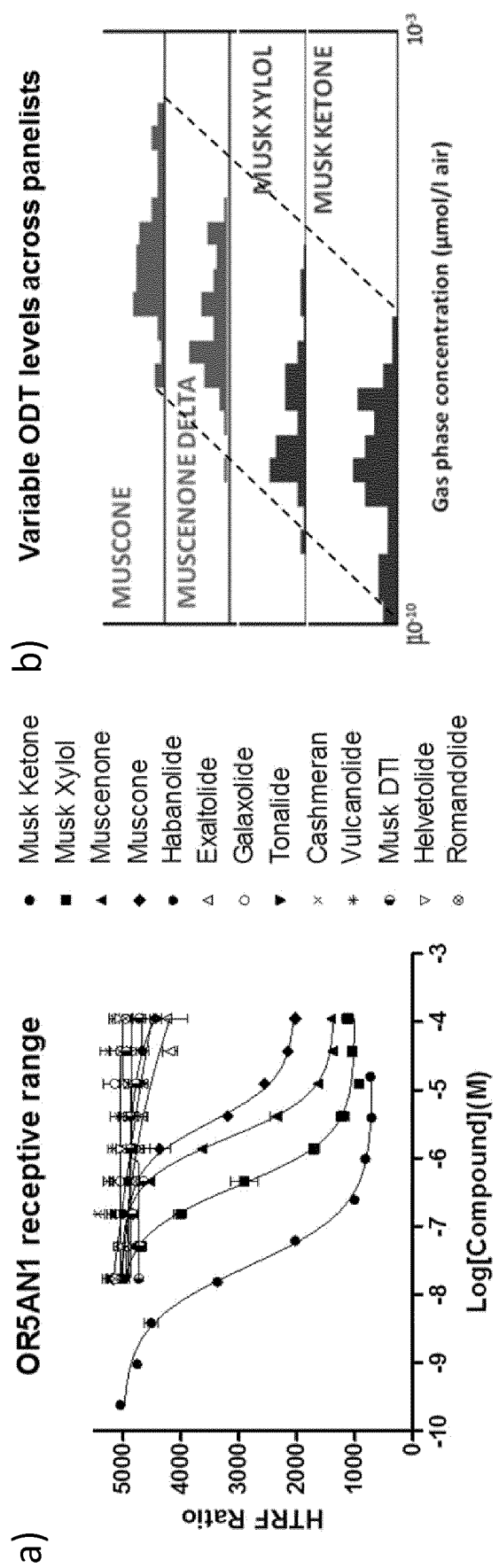
FIG. 1 shows the correlation between musk-induced in vitro levels of OR5AN1 activation recordings for a series of distinct musks (a) and the overall increasing human sensitivities as shown by odor detection threshold recordings of muscone, MUSCENONE®, musk xylol and musk ketone (b).

For the descriptions herein and the appended claims, the use of "or" means "and/or" unless stated otherwise.

Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The following terms have the meanings ascribed to them unless specified otherwise.

As used herein, the term "OR" or "olfactory receptor" or "odorant receptor" refers to one or more members of a family of G protein-coupled receptors (GPCRs) that are expressed in olfactory cells. Olfactory receptor cells can also be identified on the basis of morphology or by the expression of proteins specifically expressed in olfactory cells. OR family members may have the ability to act as receptors for olfactory signal transduction.

A target olfactory receptor refers to an olfactory receptor that can be correlated to sensory perception whether in vitro, in vivo, or ex vivo.

"Musk OR" refers to a member of the family of G protein-coupled receptors (GPCRs) that is expressed in an olfactory cell, which receptors bind and/or are activated by a musk in a binding or activity assay for identifying ligands that bind and/or activate GPCRs. Such assays are described below. Musks receptors herein will include fragments, variants, including synthetic and naturally occurring, and chimeras or recombinant nucleic acids or proteins that respond to or bind a musk compound. The same definition applies in analogy to other relevant or target ORs that can be identified by the methods described herein.

An odorant refers to any type of odorant including but not limited to a perfume, a perfume ingredient, an aroma, a foodstuff, a flavor or a flavor ingredient.

An agonist of an OR or an agonist compound refers to a compound or a ligand that binds to an OR, activates the OR and has the potential to induce a receptor transduction cascade.

As considered herein, a compound that is not an agonist of an olfactory receptor refers to a compound or ligand that binds to an OR non-competitively relative to an agonist compound and that enhances or inhibits the activity of the receptor exposed to the agonist compound when compared to the activity of the receptor exposed to the agonist compound in the absence of the compound that is not an agonist. In one aspect, the compound that is not an agonist binds to a site on the receptor different from the site where the agonist compound binds.

In one aspect, a compound that is not an agonist of an olfactory receptor has a potency and efficacy substantially lower than that of an agonist, for example, when the $EC_{50}$ value is substantially higher than that of an agonist compound and the efficacy is typically less than 20% of the efficacy of a full agonist response at saturation.

Potency refers to the measure of the activity of a receptor induced by the binding of an agonist (odorant) in terms of amount required to produce a given activity level. It indicates the sensitivity of the receptor to different agonist concentrations and is usually obtained by calculating the $EC_{50}$ (the agonist concentration necessary to achieve half-maximal receptor activity).

Efficacy refers to the measure of the intensity by which the receptor responds to a given agonist and is obtained by measuring the activation span between constitutive (baseline activity in the absence of an agonist) and agonist induced activity. Maximum efficacy is obtained at receptor saturation.

An orthosteric binding site refers to a ligand or odorant compound binding site for an agonist or a competitive antagonist. A binding event to the orthosteric site generally leads to the activation by the agonist or the inhibition by the competitive antagonist of the receptor's activity.

An allosteric binding site refers to a binding site that is topographically distinct from the orthosteric binding site. Allosteric binding in the presence of orthosteric agonist is not sterically hindered and hence occurs in a non-competing fashion. Certain allosteric ligands can act as either positive allosteric modulators (PAMs) or negative allosteric modulators (NAMs), for example, to potentiate or inhibit activation of the receptor by the agonist, respectively.

Binding competition occurs when two molecules compete to bind at the same binding site. The binding probability for each ligand is dependent on its respective affinity to the receptor and its concentration compared to the other ligand. Competition typically occurs when both ligands bind at the orthosteric site. This can be identified by performing a competition assay, such as the Schild regression analysis; when no competition is observed, both ligands can bind the receptor at the same time at two distinct binding sites, defined as the orthosteric and the allosteric binding sites, wherein the binding sites can be separated topographically on the receptor or can be adjacent or overlapping. In this case, the binding of the orthosteric ligand is not linearly dependent on the concentration of the allosteric ligand. The allosteric binding can modulate several properties of the receptor such as agonist affinity and signal transduction efficiency.

Positive or negative allosteric modulators or positive or negative allosteric modulator compounds refer to compounds or ligands that enhance or inhibit the effect of the orthosteric agonist compound or ligand binding, but are largely inactive in the absence of an orthosteric agonist compound or ligand. Allosteric inhibition or enhancement of a receptor's activity can occur by modulating the receptor's conformation and modify: 1) the orthosteric site affinity to its agonists, 2) the effect of orthosteric binding activation (e.g. efficacy); or 3) the binding to the G-protein in the case of GPCRs and decrease or increase the signal transduction efficiency, respectively.

A cooperativity factor refers to the measure of the degree of modulation of an orthosteric ligand binding effect due to the presence of an allosteric ligand.

The ability of compounds of the present disclosure to inhibit or antagonize an olfactory receptor may be determined by any suitable method readily selected by one of ordinary skill in the art, such as, for example, via an ex vivo cultured neuron assay, or via an in vitro assay using a cell line that expresses a relevant olfactory receptor, e.g. a musk olfactory receptor.

Such assays for inhibitors and activators include, e.g., expressing OR family members in cells or cell membranes, applying putative modulator compounds, in the presence or absence of agonist molecules, e.g. musk, and then determining the functional effects on olfactory transduction, as described in the Examples below. Samples or assays comprising OR family members that are treated with a potential inhibitor are compared to control samples without the inhibitor to examine the extent of inhibition. Control samples (untreated with inhibitors, but treated with the agonist) are assigned a relative maximal OR activity value of 100%.

Olfactory receptor activity assays may reveal the following data: (i) whether or not a given compound is an activator of the olfactory receptor or not, and the specificity of the compound for the particular olfactory receptor; (ii) the $EC_{50}$ of an agonist for an olfactory receptor (i.e., the $EC_{50}$ of the agonist); and/or (iii) the efficacy of an agonist for an olfactory receptor, determined by the amplitude of the response (i.e., the span between baseline and saturated activity levels).

In some aspects, enhanced activation of an OR is achieved when the normalized OR activity value (100%) relative to the agonist control is greater than 100%, for example, about 110%, optionally 120% or 150%, or greater. In one aspect, enhancement of an OR is achieved if the potency of an agonist for the OR in the presence of the enhancer compound is increased. In one aspect, the increase in potency is determined via a shift in the $EC_{50}$ for the agonist. Alternatively, in another aspect, enhancement of an OR is achieved if the $EC_{50}$ value of the agonist in the presence of the enhancer compound is decreased from between 2-fold to 30-fold. In one aspect, enhancement of an OR is achieved if the $EC_{50}$ value of the agonist compound is decreased 2-fold. In another aspect, enhancement of an OR is achieved if the $EC_{50}$ value of the agonist in the presence of the enhancer compound is decreased 30-fold.

In some aspects, enhancement of an OR is achieved if the efficacy of an OR agonist in the presence of the enhancer compound is increased relative to the agonist control. In one aspect, enhancement of an OR is achieved if the efficacy value of the agonist in the presence of the enhancer compound is increased from between 1.05-fold to 2-fold or greater. In one aspect, enhancement of an OR is achieved if the efficacy value of the agonist in the presence of the enhancer compound is increased by about 1.05-fold. In another aspect, enhancement of an OR is achieved if the efficacy value of the agonist in the presence of the enhancer compound is increased by about 2-fold.

In one aspect, inhibition of an OR is achieved when the normalized OR activity value (100%) relative to the agonist control is less than 100%, for example, about 80%, optionally 50% or 25-0%. In one aspect, inhibition of an OR is achieved if the potency of an agonist for the OR is decreased. In another aspect, the decrease in potency is determined via a shift in the $EC_{50}$ for the agonist. In one aspect, inhibition of an OR is achieved if the $EC_5$s value of the agonist in the presence of an antagonist compound is increased from between about 2-fold to about 30-fold. In one aspect, inhibition of an OR is achieved if the $EC_{50}$ value of the agonist in the presence of the antagonist compound is increased 2-fold. In one aspect, inhibition of an OR is achieved if the $EC_{50}$ value of the agonist in the presence of the antagonist compound is increased 30-fold.

In some aspects, inhibition of an OR is achieved if the efficacy of an OR agonist in the presence of the antagonist compound is decreased. In one aspect, inhibition of an OR is achieved if the efficacy value of the agonist in the presence of the antagonist compound is decreased from between about 1.25-fold to 4-fold or greater. In one aspect, inhibition of an OR is achieved if the efficacy value of the agonist in the presence of the antagonist compound is decreased to 0. In another aspect, inhibition of an OR is achieved if the efficacy value of the agonist in the presence of the antagonist compound is decreased 1.25-fold. In one aspect, inhibition of an OR is achieved if the efficacy value of the agonist in the presence of the antagonist compound is decreased 4-fold.

A synergistically enhanced activity of an OR refers to the activity of the receptor being increased by exposure of the receptor in the presence of a combination of an agonist compound and a positive allosteric modulator compound when compared to the activity of the receptor exposed to the agonist alone. In one aspect, the synergistically enhanced activity includes about a 2-fold to 30-fold increase in potency and/or about 1.05-fold to 1.5-fold or more increase in efficacy.

"OR" or "odorant receptor" or "olfactory receptor" polypeptides are considered as such if they pertain to the 7-transmembrane-domain G protein-coupled receptor superfamily encoded by a single ~1 kb long exon and exhibit characteristic olfactory receptor-specific amino acid motifs. The seven domains are called "transmembrane" or "TM" domains TM I to TM VII connected by three "internal cellular loop" or "IC" domains IC I to IC III, and three "external cellular loop" or "EC" domains EC I to EC III. The motifs and the variants thereof are defined as, but not restricted to, the MAYDRYVAIC motif (SEQ ID NO: 15) overlapping TM III and IC II, the FSTCSSH motif (SEQ ID NO: 16) overlapping IC III and TM VI, the PMLNPFIY motif (SEQ ID NO: 17) in TM VII as well as three conserved C residues in EC II, and the presence of highly conserved GN residues in TM I [Zhang, X. & Firestein, S. Nat. Neurosci. 5, 124-133 (2002); Malnic, B., et al. Proc. Natl. Acad. Sci. U.S.A 101, 2584-2589 (2004)].

"OR" nucleic acids encode a family of GPCRs with seven transmembrane regions that have "G protein-coupled receptor activity," e.g., they may bind to G proteins in response to extracellular stimuli and promote production of intracellular second messengers such as $IP_3$, cAMP, cGMP, and $Ca^{2+}$ via stimulation of enzymes such as phospholipase C and adenylate cyclase III.

"Paralogous" OR genes or "paralogs" are the result of gene duplications and refer to closely related homologous genes within the same species.

"Orthologous" OR genes or "orthologs" are defined as phylogenetically linked by a gene present in a common ancestor and refer to closely related homologous genes in other species.

The "N terminal domain" region starts at the N-terminus (amino terminus) of a peptide or protein and extends to a region close to the start of the first transmembrane region.

"Transmembrane regions" comprise the seven "transmembrane domains," which refers to the domain of OR polypeptides that lies within the plasma membrane, and may also include the corresponding cytoplasmic (intracellular) and extracellular loops. The seven transmembrane regions and extracellular and cytoplasmic loops can be identified using standard methods such as hydrophobicity profiles, or as described in Kyte & Doolittle, J. Mol. Biol., 157:105-32 (1982), or in Stryer. The general secondary and tertiary structure of transmembrane domains, in particular the seven transmembrane domains of G protein-coupled receptors such as olfactory receptors, are known in the art. Thus, primary structure sequence can be predicted based on known transmembrane domain sequences, as described in detail below. These transmembrane domains are useful for in vitro ligand-binding assays.

The phrase "functional effects" in the context of assays for testing compounds that modulate OR family member mediated olfactory transduction includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, signal transduction receptor-ligand interactions, second messenger concentrations (e.g., cAMP, cGMP, $IP_3$, or intracellular $Ca^{2+}$), in vitro, in vivo, and ex vivo and also includes other physiologic effects such as increases or decreases of neurotransmitter or hormone release.

By "determining the functional effect" or "confirming the activity" in the context of assays is meant assays for a compound that increases or decreases a parameter that is indirectly or directly under the influence of an OR family member, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte OR gene expression; tissue culture cell OR expression; transcriptional activation of OR genes or activity induced genes such as egr-1 or c-fos; ligand-binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

The terms "purified," "substantially purified," and "isolated" as used herein refer to the state of being free of other, dissimilar compounds with which the compound of the invention is normally associated in its natural state, so that the "purified," "substantially purified," and "isolated" subject comprises at least 0.5%, 1%, 5%, 10%, or 20%, or at least 50% or 75% of the mass, by weight, of a given sample. In one particular embodiment, these terms refer to the compound of the invention comprising at least 95, 96, 97, 98, 99 or 100% of the mass, by weight, of a given sample. As used herein, the terms "purified," "substantially purified," and "isolated" "isolated," when referring to a nucleic acid or protein, of nucleic acids or proteins, also refers to a state of purification or concentration different than that which occurs naturally in the mammalian, especially human body. Any degree of purification or concentration greater than that which occurs naturally in the mammalian, especially human body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

As used herein, the terms "amplifying" and "amplification" refer to the use of any suitable amplification methodology for generating or detecting recombinant of naturally expressed nucleic acid, as described in detail, below. For example, the invention provides methods and reagents (e.g., specific degenerate oligonucleotide primer pairs, oligo dT primer) for amplifying (e.g., by polymerase chain reaction, PCR) naturally expressed (e.g., genomic DNA or mRNA) or recombinant (e.g., cDNA) nucleic acids of the invention in vivo, ex vivo or in vitro.

The term "7-transmembrane receptor" means a polypeptide belonging to a superfamily of transmembrane proteins that have seven domains that span the plasma membrane seven times (thus, the seven domains are called "transmembrane" or "TM" domains TM I to TM VII).
The families of olfactory and certain taste receptors each belong to this super-family. 7 transmembrane receptor polypeptides have similar and characteristic primary, secondary and tertiary structures, as discussed in further detail below.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues.

In addition to the gene sequences shown in the sequences disclosed herein, it will be apparent for the person skilled in the art that variants also include DNA sequence polymorphisms that may exist within a given population, which may lead to changes in the amino acid sequence of the polypeptides disclosed herein. Such genetic polymorphisms may exist in cells from different populations or within a population due to natural allelic variation. Allelic variants may also include functional equivalents.

Further embodiments also relate to the molecules derived by such sequence polymorphisms from the concretely disclosed nucleic acids. These natural variations usually bring about a variance of about 1 to 5% in the nucleotide sequence of a gene or in the amino acid sequence of the polypeptides disclosed herein. As mentioned above, the nucleic acid encoding the polypeptide of an embodiment herein is a useful tool to modify non-human host organisms or host cells intended to be used in the methods described herein.

The terms "polypeptide," "peptide" and "protein" are used interchangeably herein to refer to a polymer of amino acid residues, whether comprising naturally occurring amino acids or polymers and non-naturally occurring amino acids or polymers. The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" means also the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence potentially amplified using a primer. "Recombinant" means also modifications obtained by genome editing techniques, such as CRISPR/Cas9, of a cell that leads to stable or transient expression of endogenous genes such as the receptor gene referred to herein.

The term "expression vector" refers to any recombinant expression system for the purpose of expressing a nucleic acid sequence of the invention in vitro, ex vivo, or in vivo, constitutively or inducibly, in any cell, including prokaryotic, yeast, fungal, plant, insect or mammalian cell. The term includes any linear or circular expression systems including but not limited to viral vectors, bacteriophages and plasmids. The skilled person is capable of selecting a suitable vector according to the expression system. The term includes expression systems that remain episomal or integrate into the host cell genome. The expression systems can have the ability to self-replicate or not, i.e., drive transient expression in a cell. The term includes recombinant "expression cassettes" which can contain the minimum elements needed for transcription of the recombinant nucleic acid. The term also covers cassettes or vectors for expression of endogenous genes through, for example, genome editing methods such as CRISPR/Cas9.

By "a non-human organism or a host cell" is meant a non-human organism or a cell that contains a nucleic acid as described herein or an expression vector and supports the replication or expression of the expression vector. Host cells may be prokaryotic cells such as *E. coli*, or eukaryotic cells such as yeast, insect, amphibian, or mammalian cells such as CHO, HeLa, HEK-293, and the like, e.g., cultured cells, explants, and cells in vivo.

By "tag" or "tag combination" is meant a short polypeptide sequence that can be added to the odorant receptor protein. Typically, the DNA encoding a "tag" or a "tag combination" is added to the DNA encoding the receptor, eventually resulting in a fusion protein where the "tag" or a "tag combination" is fused to the N-terminus or C-terminus of the receptor. Lucy, FLAG® and/or Rho tags can enhance the receptor trafficking to the cell membrane, hence the can assist in expression of a functional odorant receptor for in vitro cell based assay [Shepard, B. et al. PLoS One 8, e68758-e68758 (2013), and Zhuang, H. & Matsunami, H. J. Biol. Chem. 282, 15284-15293 (2007)].

Particular Embodiments

The assays and methods described herein make use of relevant human olfactory receptors and/or corresponding mouse orthologs in assays and methods for the identification of one or more compounds from a group of compounds wherein the one or more compounds positively modulates the activity of the olfactory receptor that is induced by an agonist odorant compound, where the agonist is of particular interest to perfumery, and where the combination of the target receptor, its agonist and the one or more compounds is used in the screening assays or methods.

The present disclosure provides for the identification of compounds that can be used in perfumery applications to modulate, that is, enhance desired fragrances or target agonists, such as, for example, a musk or a floral compound such as muscone or a floral muguet compound, respectively. In some aspects, volatile compounds that enhance the target agonist are positive allosteric modulators of the target agonist olfactory receptor. Without intending to be limited to any particular theory, synergistic interaction between perfumery ingredients can lead to more sensitive and more intense perception of perfumery tonalities. Such compounds thus enable new routes to optimize perfumery rules and create better performing commercial perfumery formulations.

In one embodiment, the human olfactory receptor OR5AN1 and/or its corresponding mouse ortholog Olfr1440 are used as receptors activated by various musk agonist compounds to identify compounds that modulate the activity of the receptor in the presence of the musk agonist compound. The human olfactory receptor OR5AN1 and its corresponding mouse ortholog Olfr1440 have approximately 66% sequence identity at the amino acid level.

In one embodiment, in view of the correlation between sensory outcome and the response of the OR5AN1 to musks compounds, OR5AN1 is selected as a relevant target receptor activated by particular musks, i.e. macrocyclic ketones and nitromusks, for use in assays and methods for screening for and selecting positive allosteric modulators of these musk compounds.

In another embodiment, the human olfactory receptor OR10J5 and/or its corresponding mouse ortholog Olfr16 is used as receptors for various floral muguet agonist compounds to identify compounds that modulate the activity of the receptor in the presence of a floral muguet agonist compound. The human olfactory receptor OR10J5 and its corresponding mouse ortholog Olfr16 have approximately 87% sequence identity at the amino acid level.

OR10J5 and its corresponding mouse ortholog Olfr16 floral muguet compound-induced activity correlates with the sensory outcome of perception of a floral, lily of the valley, hydroxycitronellal odor note, and an overall olfactive character reminding strongly of the one of the very well-known ingredient 3-(4-hydroxy-4-methylpentyl)cyclohex-3-ene-1-carbaldehyde, 4-(4-hydroxy-4-methylpentyl)cyclohex-3-ene-1-carbaldehyde or a mixture thereof (sold under the tradename LYRAL®, hereinafter referred to as "LYRAL®".

A floral muguet compound refers to certain compounds that impart a lily of the valley-like or muguet floral note, including but not limited to a lyral compound.

Examples of floral muguet compounds include, but are not limited to the compounds disclosed in International Patent Application Publication Nos. WO2017/009175 A1, or WO2010/091969 A1, or WO2011/029743 A1, or WO2018/134221 A1, or WO2008/068310 A1, or WO2014/198709 A1, or WO2013/117433 A1, or WO2014/180945 A1, or WO2014/180952 A1, or WO2016/074118 A1, or WO2016/074697 A1, or WO2016/074719 A1, WO2014/180952 A1, or WO2001/090038 A1, or WO2008/053148 A1, or WO2017/066214 A1.

Other examples of floral muguet compounds include, but are not limited to the compounds disclosed in U.S. Patent Application Publication Nos. US2013/0090390 A1, or US2011/0117046 A1, or US2011/0118170 A1, or US2009/0036347 A1, or US2011/0217257 A1.

Other examples of floral muguet compounds include, but are not limited to the compounds disclosed in U.S. Pat. Nos. 5,527,769 A, or 7,834,219 B1, or 2,710,825 A, or 4,352,937 A.

Other examples of floral muguet compounds include, but are not limited to the compounds disclosed in European Patent Application Publication Nos. EP2594626 A1, or EP0392258 A2, or EP2322495 A1, or EP1029845 A1, or EP1054053 A2, or EP1529770 A1.

Other examples of floral muguet compounds include, but are not limited to the compounds disclosed in European Patent Nos. EP2594626 B1, or EP685444 B1, or EP2594626 B1.

Other examples of floral muguet compounds include, but are not limited to the compounds disclosed in UK Patent Application Publication Nos. GB2528467 A, or GB988502 A, or GB1057360 A, or GB2529901 A.

Other examples of floral muguet compounds include, but are not limited to the compounds disclosed in Lamboley et al., Synthesis and Properties of Conformationally Constrained Analogues of Floral-Type Odorants, Helvetica Chimica Acta, vol. 84, pp 1767-1793 (2004).

Other examples of floral muguet compounds include, but are not limited to the compounds disclosed in Schroeder et al., γ-Unsaturated Aldehydes as Potential Lilial Replacers, Chemistry & Biodiversity, vol. 11, pp 1651-1673 (2014.

Other examples of floral muguet compounds include, but are not limited to the compounds disclosed in Skouroumounis et al., Synthesis of 1,3,4,5-Tetrahydro-2-benzoxepin Derivatives as Conformationally Restricted Analogues of Cyclamenaldehyde-Type Compounds and as Intermediates for Highly Odour-Active Homologues, Helvetica Chimica Acta, vol. 79, pp 1095-1109 (1996).

Other examples of floral muguet compounds include, but are not limited to the compounds disclosed in Winter et al., Synthesis and Odor Properties of Substituted Indane-2-carboxaldehydes. Discovery of a New Floral (Muguet) Fragrance Alcohol, Helvetica Chimica Acta, vol. 88, pp 3118-3127 (2005).

Other examples of floral muguet compounds include, but are not limited to the compounds disclosed in Coulomb, J, Beyond Mguet, Perfume and Flavorist, vol. 43 (2018).

In some embodiments, floral muguet compound is selected from the group consisting of: 3(4)-(4-hydroxy-4-methylpentyl)cyclohex-3-ene-1-carbaldehyde, 4(4)-(4-hydroxy-4-methylpentyl)cyclohex-3-ene-1-carbaldehyde or a mixture thereof; (4Z)-9-hydroxy-5,9-dimethyl-4-decenal (A)+(4E)-9-hydroxy-5,9-dimethyl-4-decenal; 3-[4-(2-hydroxy-2-methylpropyl)-2-methylphenyl]propanal; 3-[4-(2- hydroxy-2-methylpropyl)phenyl]propanal; (+−)-3-[4-(2-hydroxy-2-methylpropyl)phenyl]-2-methylpropanal; (+−)-4-(4-hydroxy-4-methylpentyl)-3,6-dihydro-2H-pyran-2-carbaldehyde; (2,5-dimethyl-2-indanyl)methyl formate; (2,5-dimethyl-1,3-dihydroinden-2-yl)methanol; (2,5,6-trimethyl-1,3-dihydroinden-2-yl)methanol; (2,4,6-trimethyl-1,3-dihydroinden-2-yl)methanol; 4-methyl-2-(2-methylpropyl)oxan-4-ol; 7-hydroxy-3,7-dimethyloctanal; and mixtures thereof.

In some embodiments, the floral muguet compound may comprise LYRAL® and/or may comprise a compound such as 3(4)-(4-hydroxy-4-methylpentyl)cyclohex-3-ene-1-carbaldehyde, 4(4)-(4-hydroxy-4-methylpentyl)cyclohex-3-ene-1-carbaldehyde or a mixture thereof, which may be sold under the following tradenames: LYRAL®, KOVANOL®, MUGONAL®, and LANDOLAL®.

This method can be used with other relevant target receptors and agonists (e.g. agonist of particular importance to perfumery) for identifying potential positive allosteric modulators of key agonists of these target receptors.

In one embodiment provided herein is an isolated nucleic acid molecule comprising a nucleic acid sequence having at least 70%, 75%, 80%, 85%, 90%, 95%, 96%, 97%, 98%, 99%, or 100% sequence identity to SEQ ID NO: 1, 3, 5, or 7, or the reverse complement thereof.

In one embodiment provided herein is an isolated nucleic acid sequence as described above which encodes a polypeptide comprising an amino acid sequence having at least 70%, 75%, 80%, 85%, 90%, 95%, 96%, 97%, 98%, 99%, or 100% sequence identity to SEQ ID NO: 2, 4, 6, or 8.

In a further embodiment provided herein is an isolated polypeptide comprising an amino acid sequence having at least 70%, 75%, 80%, 85%, 90%, 95%, 96%, 97%, 98%, 99%, or 100% sequence identity to SEQ ID NO: 2, 4, 6, or 8.

In one embodiment, a non-human organism or a host cell is transformed to express a polypeptide comprising an amino acid sequence having at least 70%, 75%, 80%, 85%, 90%, 95%, 96%, 97%, 98%, 99%, or 100% sequence identity to SEQ ID NO: 2, 4, 6, or 8.

In one embodiment, a non-human organism or a host cell is transformed to express a polypeptide comprising an amino acid sequence that is identical to SEQ ID NO: 2, 4, 6, or 8.

Further provided herein is an expression vector comprising a nucleic acid that encodes a polypeptide comprising an amino acid sequence having at least 70%, 75%, 80%, 85%, 90%, 95%, 96%, 97%, 98%, 99%, or 100% sequence identity to SEQ ID NO: 2, 4, 6, or 8.

Also provided herein is an expression vector comprising a nucleic acid that comprises a nucleic acid sequence having at least 70%, 75%, 80%, 85%, 90%, 95%, 96%, 97%, 98%, 99%, or 100% sequence identity SEQ ID NO: 1, 3, 5, or 7, or the reverse complement thereof.

Also provided herein is an expression vector having a nucleic acid wherein the nucleic acid comprises a nucleotide sequence that is identical to SEQ ID NO: 1, 3, 5, or 7, or the reverse complement thereof.

ORs can be specific for one single agonist or they may be activated by a panel of structurally different agonist or by a panel of agonists with similar structure. Agonist can also specifically activate a single OR or may activate several ORs. As an initial step for conducting the assay or methods described herein, an appropriate receptor-agonist pair is identified and selected. In one aspect, such receptor-agonist is preferably of particular interest for designing perfumery compositions.

For example, referring to FIG. 1 and Example 1, olfactory receptor OR5AN1 is a human olfactory receptor whose musk-induced activity in vitro correlates with sensory outcome of musk perception. The OR5AN1 olfactory receptor was specifically activated by the musk compounds muscone, MUSCENONE®, musk xylol, and musk ketone, and the observed activity levels, i.e. potency and efficacy, ranking correlated with individuals at the sensory level (FIG. 1). Accordingly, an in vitro screening assay of OR5AN1 activity has a predictive power with respect to the putative sensory outcome of the identified compound and thus OR5AN1 represents a good target for musk directed receptor-based enhancement.

The test substances to be tested in the methods and assays described herein are not particularly limited. The test substance may be a naturally occurring substance or a chemically or biologically synthesized artificial substance. The test substance may be a compound or a mixture of compounds.

Figure 6:
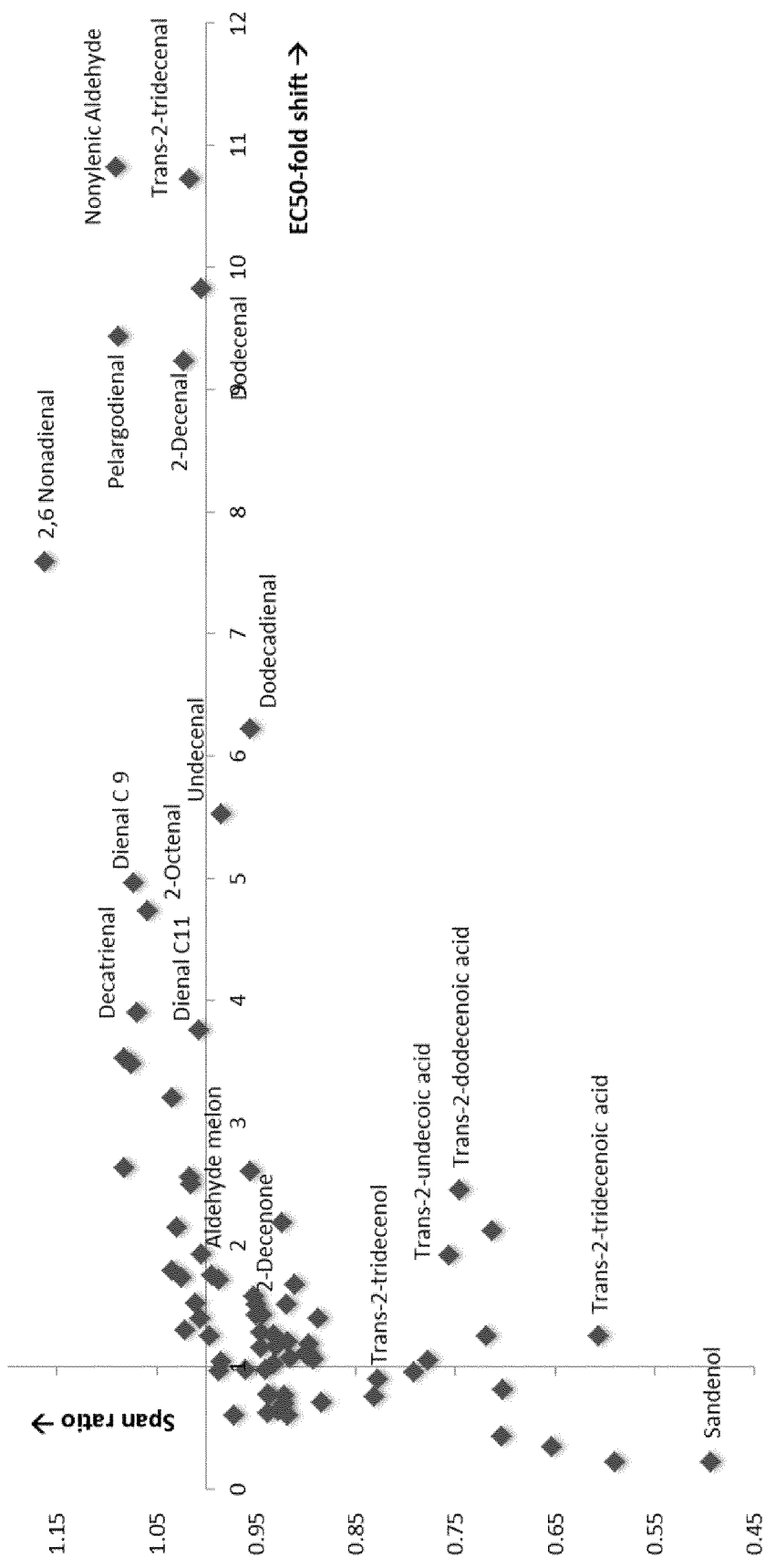
FIG. 6 shows a ranking of 67 volatile compounds according to their OR5AN1 Musk response enhancement capacity based on potency shift and efficacy increase.

Referring to FIG. 6, α-β-mono-unsaturated disubstituted aliphatic aldehydes were systematically found to exhibit potent enhancement of the activity of the OR5AN1 olfactory receptor.

Accordingly, one aspect presented herein provides a positive allosteric modulator having the structure:

Formula (I)

in the form of any one of its stereoisomers or a mixture thereof, wherein R represents a $C_{3-11}$ linear alkyl group optionally substituted by an $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, and wherein the compound of Formula (I) is a positive allosteric modulator of a musk olfactory receptor.

For the sake of clarity, by the expression "any one of its stereoisomers", or the similar, it is meant the normal meaning understood by a person skilled in the art, i.e. that the invention compound can be a pure enantiomer (if chiral) or diastereomer (e.g. the double bond is in a conformation E or Z).

In some aspects, the compound of Formula (I) is selected from the group consisting of: (E,E)-2,4-decadienal, (E)-2-undecenal, (E,E)-2,4-nonadienal, (E)-2-tridecenal, (2E)-2-dodecenal, (2E,6Z)-2,6-nonadienal, (E,E)-2,6-nonadienal, (2E)-2,4-undecadienal, (2E)-2,4-dodecadienal, (E)-2-nonenal, (2E,4E,7Z)-decatrienal, (Z)-2-decenal, (E)-2-octenal, (E)-2-decenal, (Z)-4-(benzyloxy)but-2-enal, (E)-4-(benzyloxy)but-2-enal, (E)-4-cyclohexylidenebut-2-enal, (2E)-3-(4-methylphenyl)-2-propenal, (2E,5E)-6,10-dimethyl-2,5,9-undecatrienal, (2E)-7,8-dimethyl-2,7-nonadienal, methyl (5E)-7-oxo-5-heptenoate, (2E)-7-methyl-2,6-octadienal, (2E)-6,6-dimethyl-2-heptenal, (+−)-(2E)-5,9-dimethyl-2,8-decadienal, (E)-2-tetradecenal, and (E)-8-methoxy-4,8-dimethylnon-2-enal.

In one aspect, the receptor is OR10J5, the agonist odorant compound comprises a floral muguet compound; and the selected compound comprises at least one positive allosteric modulator selected from the group consisting of: octanal;

(E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof; 4-ethylbenzaldehyde; 6-methoxy-2,6-dimethylheptanal; (E)-non-2-enal; and combinations thereof.

In one aspect, the positive allosteric modulators specifically enhance the activity of the particular receptor independently of the receptor agonist (activating compound).

Methods of Monitoring OR Activity

As long as the function of the OR is not impaired, it may be used in any form in a method or assay described herein. For example, the OR may be use as follows: tissues or cells which intrinsically express an OR such as olfactory sensory neurons isolated from living bodies and cultured products thereof; olfactory cell membrane bearing the OR; recombinant cells genetically modified so as to express the OR and cultured products thereof; membrane of the recombinant cells; and artificial lipid bilayer membrane carrying the OR.

In a further embodiment, indicators for monitoring the activity of olfactory receptors are selected from a fluorescent calcium indicator dye, a calcium indicator protein (e.g. GCaMP, a genetically encoded calcium indicator), a fluorescent cAMP indicator, a cell mobilization assay, a cellular dynamic mass redistribution assay, a label-free cell based assay, a cAMP response element (CRE) mediated reporter protein, a biochemical cAMP HTRF assay, a beta-arrestin assay, or an electrophysiological recording. Particularly, a calcium indicator dye is selected that can be used to monitor the activity of olfactory receptors expressed on the membrane of the olfactory neurons (e.g., Fura-2 AM).

In a particular embodiment, compounds are screened sequentially and the odorant-dependent changes in calcium dye fluorescence are measured using a fluorescent microscope or fluorescent-activated cell sorter (FACS).

In a further embodiment, molecular 3D receptor modeling of olfactory receptors is used to assess the binding potential in silico and to identify compounds that may activate, mimic, block, inhibit, modulate, and/or enhance the activity of an olfactory receptor.

As an example, olfactory neurons activated by the target agonist, e.g. musk or floral compounds, are isolated using either a glass microelectrode attached to a micromanipulator or a FACS machine. Mouse olfactory sensory neurons are screened by Ca2+ imaging similar to procedures previously described [Malnic, B., et al. Cell 96, 713-723 (1999); Araneda, R. C. et al. J. Physiol. 555, 743-756 (2004); and WO2014/210585 hereby incorporated by reference in its entirety]. Particularly, a motorized movable microscope stage is used to increase the number of cells that can be screened to at least 1,500 per experiment. Since there are approximately 1,200 different olfactory receptors in the mouse and each olfactory sensory neurons expresses only 1 of 1,200 olfactory receptor genes, this screening capacity will cover virtually the entire mouse odorant receptor repertoire. In other words, the combination of calcium imaging for high-throughput olfactory sensory neuron screening leads to the identification of nearly all of the odorant receptors that respond to a particular profile of odorants. In a particular aspect, odorant receptors that respond to the target agonist, e.g. musk or floral compounds, can be isolated. For example, at least one neuron is isolated.

For calcium imaging of olfactory neurons, the main olfactory epithelium may be dissected from a mouse before neuronal dissociation. Dissected olfactory epithelium may then be transferred to a dissociation buffer for mechanical and enzymatic dissociation. Dissociated neurons may then be seeded onto a coverslip allowing the screening of thousands of cells by fluorescence microscopy and the cells may be loaded with a calcium sensitive dye (Fura-2 AM) for example for about 30 minutes at 31° C. and transferred onto the microscope ready for screening. Cells are stimulated by perfusing diluted solutions of odorants (in physiological saline) over the dissociated olfactory neurons. The rare cells that respond to the malodor compound are identified by for example stimulating the receptors with 50 µm of the malodor compounds and then by monitoring the intracellular Ca2+ flux indicated by changes in Fura-2 fluorescence. After analysis, responding cells may be retrieved from a glass coverslip with a suction micropipette. Isolated cells are then pooled into one sample or treated individually for subsequent identification of the odorant receptor genes expressed as mRNA in the responding cells.

In a particular embodiment, the mRNAs of olfactory neurons are purified and amplified according to the method generally described in Marko, N. F., et al., (2005) A robust method for the amplification of RNA in the sense orientation. BMC genomics, 6, 27; doi:10.1186/1471-2164-6-27 (Eberwine method). At least a portion of the transcriptome (up to including the entire transcriptome) is sequenced using Next-Generation Sequencing (NGS) technologies or hybridized to known genes using Microarray technologies. NGS is generally discussed and described in Metzker, M. L. Nat. Rev. Genet. 11, 31-46 (2010). In a particular embodiment, a minimum of 5 neurons presenting the same response profile are pooled. The mRNAs are released by cell lysis immediately after picking; no DNAse and no purification steps are carried out. The mRNA are amplified by two consecutive rounds of in vitro transcription (IVT). The amplification may be done according to MesageAmpII aRNA kit (Ambion, AMA1751) with the following parameters: two rounds of consecutive 14 hour long IVT.

In a further embodiment, the mRNA of a single olfactory neuron is purified and amplified with LD-PCR (Long Distance Polymerase Chain Reaction) based methods such as the one described in NGS-ready kits (e.g., Clontech/Takara, SMARTer® Ultra® Low Input RNA Kit for Sequencing—v3, cat. 634848) for next-generation sequencing (NGS). Single cell mRNA is first reverse transcribed into the corresponding cDNA, which subsequently is amplified with 18 PCR cycles and serves as NGS sample for transcriptome sequencing.

In yet another embodiment, the identity of a group or gene family of olfactory receptors for the target agonist, e.g. musk or floral compounds, is determined (e.g., up to as many as the number of neurons picked) by comparing the results of the NGS reads obtained from the isolated activated olfactory sensory neurons to a reference genome sequence of the same species. Particularly, the putative receptors for the target agonist, e.g. musk or floral compounds, will be the most highly abundant olfactory receptor mRNA in the olfactory neuron-derived NGS sample or present in more than one independent biological replicate. Because of the combinatorial nature of the olfactory code (one compound activates many ORs and one OR can be activated by many compounds), pooling several neurons activated by given compounds allows the retrieval of virtually all of the receptors responsible for the perception of these molecules in a single NGS experiment. Pooling functionally similar neurons thus greatly improves the deorphanization throughput and speed.

Standard bioinformatics tools are then used to identify the most closely related human odorant receptor(s) to other putative mammalian (non-human) receptor(s) for the target agonist, e.g. musk or floral compounds, under the assumption that homologous sequence receptors retain similar function. Several methods successfully identify human OR-ligand pairs based on this assumption [Armelin-Correa and Malnic (2017)] and up to 80% of mouse-human orthologs appear to maintain similar functional response profiles [Adipietro, K. A, et al. PLoS Genet. 8, e1002821-e1002821 (2012)]. Default parameters of BLASTP and/or BLASTN algorithm, or other ortholog pair identification algorithms such as InParanoid may be used.

The human or non-human mammalian receptors for the target agonist, e.g. musk or floral compounds, may be adapted to a functional assay that can be used to identify compounds that bind, suppress, block, inhibit, and/or modulate the activity of the olfactory receptors. In particular, the assay may be a cell-based assay or a binding assay and the method for identifying compounds may be a high-throughput screening assay. More particularly, provided herein are receptor-based assays adaptable for high-throughput screening of receptors with compound libraries for the discovery of positive allosteric modulator compounds to the particular agonist of interest.

In one embodiment, the target agonist (e.g. musk or floral compounds) receptor gene sequences are identified from the target agonist-sensitive cells as follows: Pooled neurons are heated to 75° C. for 10 minutes to break the cell membrane and render their mRNA available for amplification. This amplification step is important when applying NGS technologies with limited amount of starting material, typically between 1 to 15 cells. A linear amplification according to the Eberwine method (IVT) ensures the maintenance of the relative transcription levels of expressed genes. Two consecutive overnight (14h) rounds of in vitro transcription are used to yield sufficient amounts of cRNA; Amplified cRNA is then used to generate an Illumina HiSeq cDNA library. The resulting short sequences of typically 75 to 150 base pairs (commonly referred to as "reads") are aligned against the reference genome of the mouse (such as UCSC version mm9 or mm10) in order to build the full transcriptome of these cells. Quantitative analysis of the transcriptome data yields a list of transcribed odorant receptor genes and their respective expression levels. Odorant receptor genes that show the most abundant levels of mRNA (most abundant "reads") or are present in more than one replicate experiment are considered putative target agonist receptors.

The predicted mouse OR genes are then used to mine the latest versions of both the mouse and human genome databases in order to identify the most closely related receptors (i.e. highest sequence similarity) in mouse (paralogous genes) and in human (orthologous genes). This process may be performed using the BLAST search algorithm (publically available at the NCBI website), a sequence similarity search tool, where every putative gene sequence previously obtained from the initial transcriptome analysis is used as a query sequence. The newly identified genes identified from this data mining process are considered to be potential musk or floral receptors under the assumption that paralogous and orthologous genes are highly likely to possess similar activities. In a particular embodiment, pairwise comparison of sequence homology is carried out to identify closely related receptors in mouse and humans and the receptors are identified as described in WO2014/210585. Other approaches may also be used such as RT-PCR and microarray or mass spectrometry approaches.

In a further embodiment, to complete the deorphanization process, the candidate OR genes are further expressed in vitro for confirmation of activity against the compounds used to isolate the olfactory sensory neurons and other structurally-related compounds of interest. The mouse receptors identified from isolated olfactory neurons that respond to the target agonist (e.g. musk or floral compounds) at their N-terminus with short polypeptide sequences (e.g., FLAG® (SEQ ID NO: 10), Rho (SEQ ID NO: 12; 20 first amino acids of the bovine rhodopsin receptor), and/or Lucy (SEQ ID NO: 14; cleavable leucine-rich signal peptide sequence) tags), transiently expressed in HEK 293T cells, and stimulated separately with the target agonist (e.g. musk or floral compounds) to confirm their identity as bona fide receptors of the particular target agonist. In a further embodiment, an RTP1 gene can also be expressed in the cell lines whether through activation of the endogenous RTP1 gene, as described in WO 2016201153 A1, or through transformation or viral transduction. Co-expression of the human G alpha subunit $G\alpha_{olf}$ in this cell-based assay activates the Gs transduction pathway that leads to an internal cAMP increase upon binding to the appropriate ligand. Alternatively, co-expression of the human G alpha subunit $G\alpha_{15}$ in the cell based assay activates the Gq transduction pathway that leads to an internal $Ca^{2+}$ increase upon binding to the appropriate ligand. The above process and the results obtained so far serve to validate the process for rapid and reliable identification of mammalian odorant receptors for the target agonist.

Further provided are assays for identifying compounds that are positive allosteric modulators of the target agonist based on the use of the particular target agonist-receptor pair. In a further embodiment provided herein is a positive allosteric modulator compound that binds to a site on the olfactory receptor different than the site where the agonist binds and enhances the activity of at least one olfactory receptor selected from the group consisting of OR5AN1, OR10J5, Olfr1440 or Olfr16, and that is identified by the methods described herein, for example, the compounds described herein below.

In one embodiment the activity of the compound is determined by comparing its binding in combination with the target agonist to that of the target agonist alone, and to that of the compound alone.

In a further embodiment, a compound is contacted to a receptor, or a chimera or fragment in combination with the target agonist, wherein the receptor, or a chimera or fragment thereof is expressed in a cell that is recombinantly modified to express the receptor polypeptide.

The activity of the compound can be determined using in vivo, ex vivo, in vitro and synthetic screening systems.

In another embodiment, the contacting is performed with liposomes or virus-induced budding membranes containing the polypeptides described herein.

In another embodiment, the methods for identifying compounds that bind, suppress, block, inhibit, and/or modulate the activity of an olfactory receptor that are specific to the target agonist may be performed on intact cells or a membrane fraction from cells expressing the polypeptides described here.

In one embodiment, the ORs described herein are involved in the perception of the particular target agonist, e.g. musk or floral muguet compounds, and constitute valuable candidate receptors for the identification of positive allosteric modulator compounds that would enhance the perception of the particular target agonist when in combination with the target agonist.

Polypeptides Applicable According to the Invention

The present invention relates to "functional equivalents" or "analogs" or "functional mutations" of the polypeptides specifically described herein.

For example, "functional equivalents" refer to polypeptides which, in a test used for OR activity, display at least a 1 to 10%, or at least 20%, or at least 50%, or at least 75%, or at least 90% higher or lower OR activity, as defined herein.

"Functional equivalents", according to the invention, also cover particular mutants, which, in at least one sequence position of the amino acid sequences stated herein, have an amino acid that is different from that concretely stated, but nevertheless possess one of the aforementioned biological activities. "Functional equivalents" thus comprise the mutants obtainable by one or more, like 1 to 20, 1 to 15 or 5 to 10 amino acid additions, substitutions, in particular conservative substitutions, deletions and/or inversions, where the stated changes can occur in any sequence position, provided they lead to a mutant with the profile of properties according to the invention. Functional equivalence is in particular also provided if the activity patterns coincide qualitatively between the mutant and the unchanged polypeptide, i.e. if, for example, interaction with the same agonist or antagonist, however at a different rate, (i.e. expressed by an $EC_{50}$ or $IC_{50}$ value or any other parameter suitable in the present technical field) is observed. Examples of suitable (conservative) amino acid substitutions are shown in the following table:

| Original residue | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxyl groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent polypeptides can be determined on the basis of the concrete parameters of the invention.

"Functional equivalents" also comprise fragments, preferably individual domains or sequence motifs, of the polypeptides according to the invention, which for example display the desired biological function.

"Functional equivalents" are, moreover, fusion proteins, which have one of the polypeptide sequences stated herein or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" which are also comprised in accordance with the invention are homologs to the specifically disclosed polypeptides. These have at least 60%, preferably at least 75%, in particular at least 80 or 85%, such as, for example, 90, 91, 92, 93, 94, 95, 96, 97, 98 or 99%, homology (or identity) to one of the specifically disclosed amino acid sequences, calculated by the algorithm of Pearson and Lipman, Proc. Natl. Acad, Sci. (USA) 85(8), 1988, 2444-2448. A homology or identity, expressed as a percentage, of a homologous polypeptide according to the invention means in particular an identity, expressed as a percentage, of the amino acid residues based on the total length of one of the amino acid sequences described specifically herein.

The identity data, expressed as a percentage, may also be determined with the aid of BLAST alignments, algorithm blastp (protein-protein BLAST), or by applying the Clustal settings specified herein below.

In the case of a possible protein glycosylation, "functional equivalents" according to the invention comprise polypeptides as described herein in deglycosylated or glycosylated form as well as modified forms that can be obtained by altering the glycosylation pattern.

Such functional equivalents or homologues of the polypeptides according to the invention can be produced by mutagenesis, e.g. by point mutation, lengthening or shortening of the protein or as described in more detail below.

Such functional equivalents or homologues of the polypeptides according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art (e.g. Narang, S. A. (1983); Itakura et al. (1984) (a); Itakura et al., (1984) (b); Ike et al. (1983)). Generation of polypeptides with codon-optimized nucleic acid sequences, i.e. adapted to the codon usage frequency of the host cell, are also covered under this method.

Several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues (Arkin and Yourvan (1992); Delgrave et al. (1993)).

Coding Nucleic Acid Sequences Applicable According to the Invention

The invention also relates to nucleic acid sequences that code for polypeptides as defined herein.

The present invention also relates to nucleic acids with a certain degree of "identity" to the sequences specifically disclosed herein. "Identity" between two nucleic acids means identity of the nucleotides, in each case over the entire length of the nucleic acid.

For example the identity may be calculated by means of the Vector NTI Suite 7.1 program of the company Informax (USA) employing the Clustal Method (Higgins D G, Sharp P M. ((1989))) with the following settings:

| Multiple alignment parameter | |
| --- | --- |
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

| Pairwise alignment parameter | |
| --- | --- |
| FAST algorithm | on |
| K-tuple size | 1 |
| Gap penalty | 3 |
| Window size | 5 |
| Number of best diagonals | 5 |

Alternatively the identity may be determined according to Chenna, et al. (2003), the web page: http://www.ebi.ac.uk/Tools/clustalw/index.html# and the following settings

| | |
| --- | --- |
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The invention also relates to nucleic acid sequences (single-stranded and double-stranded DNA and RNA sequences, e.g. cDNA and mRNA), coding for one of the above polypeptides and their functional equivalents, which can be obtained for example using artificial nucleotide analogs.

The invention relates both to isolated nucleic acid molecules, which code for polypeptides according to the invention or biologically active segments thereof, and to nucleic acid fragments, which can be used for example as hybridization probes or primers for identifying or amplifying coding nucleic acids according to the invention.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (see below) on at least about 12, preferably at least about 25, for example about 40, 50 or 75 successive nucleotides of a sense strand of a nucleic acid sequence according to the invention or of a corresponding antisense strand.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, (1989)). In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences ac-cording to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These standard conditions vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), (1985), Brown (ed) (1991).

"Hybridization" can in particular be carried out under stringent conditions. Such hybridization conditions are for example described in Sambrook (1989), or in Current Protocols in Molecular Biology, John Wiley & Sons, N.Y. (1989), 6.3.1-6.3.6.

As used herein, the term hybridization or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein.

Appropriate hybridization conditions can be selected by those skilled in the art with minimal experimentation as exemplified in Ausubel et al. (1995, Current Protocols in Molecular Biology, John Wiley & Sons, sections 2, 4, and 6). Additionally, stringency conditions are described in Sambrook et al. (1989, Molecular Cloning: A Laboratory Manual, 2nd ed., Cold Spring Harbor Press, chapters 7, 9, and 11).

As used herein, defined conditions of low stringency are as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 18-20 h at 40° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of moderate stringency are as follows. Filters containing DNA are pretreated for 7 h at 50° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 30 h at 50° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in the prehybridization mixture containing 100 µg/ml denatured salmon sperm DNA and 5-20×106 cpm of 32P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 minutes.

Other conditions of low, moderate, and high stringency well known in the art (e.g., as employed for cross-species hybridizations) may be used if the above conditions are inappropriate (e.g., as employed for cross-species hybridizations).

The invention also relates to derivatives of the concretely disclosed or derivable nucleic acid sequences.

Thus, further nucleic acid sequences according to the invention can be derived from the sequences specifically disclosed herein and can differ from it by addition, substitution, insertion or deletion of individual or several nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism, as well as naturally occurring variants, e.g. splicing variants or allelic variants, thereof.

It also relates to sequences that can be obtained by conservative nucleotide substitutions (i.e. the amino acid in question is replaced by an amino acid of the same charge, size, polarity and/or solubility).

The invention also relates to the molecules derived from the concretely disclosed nucleic acids by sequence polymorphisms. These genetic polymorphisms can exist between individuals within a population owing to natural variation. These natural variations usually produce a variance of 1 to 5% in the nucleotide sequence of a gene.

Derivatives of nucleic acid sequences according to the invention mean for example allelic variants, having at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

Furthermore, derivatives are also to be understood to be homologues of the nucleic acid sequences according to the invention, for example animal, plant, fungal or bacterial homologues, shortened sequences, single-stranded DNA or RNA of the coding and noncoding DNA sequence. For example, homologues have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

Generation of Functional Polypeptide Mutants

Moreover, a person skilled in the art is familiar with methods for generating functional mutants, that is to say nucleotide sequences which code for a polypeptide with at least 80%, 81%, 82%, 83%, 84%, 85%, 86%, 87%, 88%, 89%, 90%, 91%, 92%, 93%, 94%, 95%, 96%, 97%, 98% or 99% sequence identity to anyone of SEQ ID NO: 2, 4, 6, or 8; and/or encoded by a nucleic acid molecule comprising a nucleotide sequence having at least 70% sequence identity to SEQ ID NO: 1, 3, 5, or 7.

Depending on the technique used, a person skilled in the art can introduce entirely random or else more directed mutations into genes or else noncoding nucleic acid regions (which are for example important for regulating expression) and subsequently generate genetic libraries. The methods of molecular biology required for this purpose are known to the skilled worker and for example described in Sambrook and Russell, Molecular Cloning. 3rd Edition, Cold Spring Harbor Laboratory Press 2001.

Methods for modifying genes and thus for modifying the polypeptide encoded by them have been known to the skilled worker for a long time, such as, for example site-specific mutagenesis, where individual or several nucleotides of a gene are replaced in a directed fashion (Trower M K (Ed.) 1996; In vitro mutagenesis protocols. Humana Press, New Jersey), saturation mutagenesis, in which a codon for any amino acid can be exchanged or added at any point of a gene (Kegler-Ebo D M, Docktor C M, DiMaio D (1994) Nucleic Acids Res 22:1593; Barettino D, Feigenbutz M, Valcarel R, Stunnenberg H G (1994) Nucleic Acids Res 22:541; Barik S (1995) Mol Biotechnol 3:1), error-prone polymerase chain reaction, where nucleotide sequences are mutated by error-prone DNA polymerases (Eckert K A, Kunkel T A (1990) Nucleic Acids Res 18:3739);

the SeSaM method (sequence saturation method), in which preferred exchanges are prevented by the polymerase. Schenk et al., Biospektrum, Vol. 3, 2006, 277-279 the passaging of genes in mutator strains, in which, for example owing to defective DNA repair mechanisms, there is an increased mutation rate of nucleotide sequences (Greener A, Callahan M, Jerpseth B (1996) An efficient random mutagenesis technique using an E. coli mutator strain. In: Trower M K (Ed.) In vitro mutagenesis protocols. Humana Press, New Jersey), or DNA shuffling, in which a pool of closely related genes is formed and digested and the fragments are used as templates for a polymerase chain reaction in which, by repeated strand separation and reassociation, full-length mosaic genes are ultimately generated (Stemmer WPC (1994) Nature 370:389; Stemmer WPC (1994) Proc Natl Acad Sci USA 91:10747).

Using so-called directed evolution (described, inter alia, in Reetz M T and Jaeger K-E (1999), Topics Curr Chem 200:31; Zhao H, Moore J C, Volkov A A, Arnold F H (1999), Methods for optimizing industrial polypeptides by directed evolution, In: Demain A L, Davies J E (Ed.) Manual of industrial microbiology and biotechnology. American Society for Microbiology), a skilled worker can produce functional mutants in a directed manner and on a large scale. To this end, in a first step, gene libraries of the respective polypeptides are first produced, for example using the methods given above. The gene libraries are expressed in a suitable way, for example by bacteria or by phage display systems.

The relevant genes of host organisms which express functional mutants with properties that largely correspond to the desired properties can be submitted to another mutation cycle. The steps of the mutation and selection or screening can be repeated iteratively until the present functional mutants have the desired properties to a sufficient extent. Using this iterative procedure, a limited number of mutations, for example 1, 2, 3, 4 or 5 mutations, can be performed in stages and assessed and selected for their influence on the activity in question. The selected mutant can then be submitted to a further mutation step in the same way. In this way, the number of individual mutants to be investigated can be reduced significantly.

The results according to the invention also provide important information relating to structure and sequence of the relevant polypeptides, which is required for generating, in a targeted fashion, further polypeptides with desired modified properties. In particular, it is possible to define so-called "hot spots", i.e. sequence segments that are potentially suitable for modifying a property by introducing targeted mutations.

Information can also be deduced regarding amino acid sequence positions, in the region of which mutations can be effected that should probably have little effect on the activity, and can be designated as potential "silent mutations".

Constructs for Preparing Polypeptides of the Invention

The nucleotide sequence as described above may be part of an expression cassette. The terms expression cassette and expression construct are used synonymously. The preferably recombinant expression construct contains a nucleotide sequence which encodes a polypeptide according to the invention and which is under genetic control of regulatory nucleic acid sequences.

In a process applied according to the invention, the expression cassette may be part of an expression vector, in particular of a recombinant expression vector.

An "expression unit" is understood as meaning, in accordance with the invention, a nucleic acid with expression activity which comprises a promoter as defined herein and, after functional linkage with a nucleic acid to be expressed or a gene, regulates the expression, i.e. the transcription and the translation of said nucleic acid or said gene. It is therefore in this connection also referred to as a "regulatory nucleic acid sequence". In addition to the promoter, other regulatory elements, for example enhancers, can also be present.

An "expression cassette" or "expression construct" is understood as meaning, in accordance with the invention, an expression unit which is functionally linked to the nucleic acid to be expressed or the gene to be expressed. In contrast to an expression unit, an expression cassette therefore comprises not only nucleic acid sequences which regulate transcription and translation, but also the nucleic acid sequences that are to be expressed as protein as a result of transcription and translation.

The terms "expression" or "overexpression" describe, in the context of the invention, the production or increase in intracellular activity of one or more polypeptides in a microorganism, which are encoded by the corresponding DNA. To this end, it is possible for example to introduce a gene into an organism, replace an existing gene with another gene, increase the copy number of the gene(s), use a strong promoter or use a gene which encodes for a corresponding polypeptide with a high activity; optionally, these measures can be combined.

Preferably such constructs according to the invention comprise a promoter 5'-upstream of the respective coding sequence and a terminator sequence 3'-downstream and optionally other usual regulatory elements, in each case in operative linkage with the coding sequence.

A "promoter", a "nucleic acid with promoter activity" or a "promoter sequence" is understood as meaning, in accordance with the invention, a nucleic acid which, when functionally linked to a nucleic acid to be transcribed, regulates the transcription of said nucleic acid.

In this context, a "functional" or "operative" linkage is understood as meaning for example the sequential arrangement of one of the nucleic acids with promoter activity and of a nucleic acid sequence to be transcribed and optionally further regulatory elements, for example nucleic acid sequences which ensure the transcription of nucleic acids, and for example a terminator, in such a way that each of the regulatory elements can perform its function upon transcription of the nucleic acid sequence. This does not necessarily require a direct linkage in the chemical sense. Genetic control sequences, for example enhancer sequences, can even exert their function on the target sequence from more remote positions or even from other DNA molecules. Preferred arrangements are those in which the nucleic acid sequence to be transcribed is positioned behind (i.e. at the 3'-end of) the promoter sequence so that the two sequences are joined together covalently. The distance between the promoter sequence and the nucleic acid sequence to be expressed recombinantly can be smaller than 200 base pairs, or smaller than 100 base pairs or smaller than 50 base pairs.

In addition to promoters and terminator, the following may be mentioned as examples of other regulatory elements: targeting sequences, enhancers, polyadenylation signals, selectable markers, amplification signals, replication origins and the like. Suitable regulatory sequences are described, for example, in Goeddel, Gene Expression Technology: Methods in Enzymology 185, Academic Press, San Diego, CA (1990).

Nucleic acid constructs according to the invention comprise in particular a sequence coding for a polypeptide for example derived from SEQ ID NO: 1, 3, 5, or 7, or the reverse complement thereof. or derivatives and homologs thereof, and the nucleic acid sequences which can be derived therefrom and which have been linked operatively or functionally with one or more regulatory signals, advantageously for controlling, for example increasing, gene expression.

In addition to these regulatory sequences, the natural regulation of these sequences may still be present before the actual structural genes and optionally may have been genetically modified so that the natural regulation has been switched off and expression of the genes has been enhanced. The nucleic acid construct may, however, also be of simpler construction, i.e. no additional regulatory signals have been inserted before the coding sequence and the natural promoter, with its regulation, has not been removed. Instead, the natural regulatory sequence is mutated such that regulation no longer takes place and the gene expression is increased.

A preferred nucleic acid construct advantageously also comprises one or more of the already mentioned "enhancer" sequences in functional linkage with the promoter, which sequences make possible an enhanced expression of the nucleic acid sequence. Additional advantageous sequences may also be inserted at the 3'-end of the DNA sequences, such as further regulatory elements or terminators. One or more copies of the nucleic acids according to the invention may be present in a construct. In the construct, other markers, such as genes which complement auxotrophisms or antibiotic resistances, may also optionally be present so as to select for the construct.

Examples of suitable regulatory sequences are present in promoters such as cos, tac, trp, tet, trp-tet, lpp, lac, lpp-lac, lacIq, T7, T5, T3, gal, trc, ara, rhaP (rhaPBAD)SP6, lambda-PR or in the lambda-PL promoter, and these are advantageously employed in Gram-negative bacteria. Further advantageous regulatory sequences are present for example in the Gram-positive promoters amy and SPO2, in the yeast or fungal promoters ADC1, MFalpha, AC, P-60, CYC1, GAPDII, TEF, rp28, ADH. Artificial promoters may also be used for regulation.

For expression in a host organism, the nucleic acid construct is inserted advantageously into a vector such as, for example, a plasmid or a phage, which makes possible optimal expression of the genes in the host. Vectors are also understood as meaning, in addition to plasmids and phages, all the other vectors which are known to the skilled worker, that is to say for example viruses such as SV40, CMV, baculovirus and adenovirus, transposons, IS elements, plasmids, cosmids and linear or circular DNA. These vectors are capable of replicating autonomously in the host organism or else chromosomally. These vectors are a further development of the invention.

Suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III113-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac+, pBIN19, pAK2004 or pDH51. The abovementioned plasmids are a small selection of the plasmids which are possible. Further plasmids are well known to the skilled worker and can be found for example in the book Cloning Vectors (Eds. Pouwels P. H. et al. Elsevier, Amsterdam-New York-Oxford, 1985, ISBN 0 444 904018).

In a further development of the vector, the vector which comprises the nucleic acid construct according to the invention or the nucleic acid according to the invention can advantageously also be introduced into the microorganisms in the form of a linear DNA and integrated into the host organism's genome via heterologous or homologous recombination. This linear DNA can consist of a linearized vector such as a plasmid or only of the nucleic acid construct or the nucleic acid according to the invention.

For optimal expression of heterologous genes in organisms, it is advantageous to modify the nucleic acid sequences to match the specific "codon usage" used in the organism. The "codon usage" can be determined readily by computer evaluations of other, known genes of the organism in question.

An expression cassette according to the invention is generated by fusing a suitable promoter to a suitable coding nucleotide sequence and a terminator or polyadenylation signal. Customary recombination and cloning techniques are used for this purpose, as are described, for example, in T. Maniatis, E. F. Fritsch and J. Sambrook, Molecular Cloning: A Laboratory Manual, Cold Spring Harbor Laboratory, Cold Spring Harbor, NY (1989) and in T. J. Silhavy, M. L. Berman and L. W. Enquist, Experiments with Gene Fusions, Cold Spring Harbor Laboratory, Cold Spring Harbor, NY (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which makes possible optimal expression of the genes in the host. Vectors are well known to the skilled worker and can be found for example in "cloning vectors" (Pouwels P. H. et al., Ed., Elsevier, Amsterdam-New York-Oxford, 1985).

Nucleic acid and amino acid sequences identified and/or used herein are listed below:

```
Human OR5AN1
Homo sapiens OR5AN1 Musk receptor
DNA
                                                           SEQ ID NO: 1
atgactgggggaggaaatattacagaaatcacctatttcatcctgctgggattctcagattttcccaggatcataaa agtgctcttcactatattcctggtgatctacattacatctctggcctggaacctctccctcattgttttaataagga tggattcccacctccatacacccatgtatttcttcctcagtaacctgtccttcatagatgtctgctatatcagctcc acagtccccaagatgctctccaacctcttacaggaacagcaaactatcacttttgttggttgtattattcagtactt tatcttttcaacgatgggactgagtgagtcttgtctcatgacagccatggcttatgatcgttatgctgccatttgta accccctgctctattcatccatcatgtcacccaccctctgtgtttggatggtactgggagcctacatgactggcctc actgcttctttattccaaattggtgctttgcttcaactccacttctgtgggtctaatgtcatcagacatttcttctg tgacatgccccaactgttaatcttgtcctgtactgacactttctttgtacaggtcatgactgctatattaaccatgt tctttgggatagcaagtgccctagttatcatgatatcctatggctatattggcatctccatcatgaagatcacttca gctaaaggcaggtccaaggcattcaacacctgtgcttctcatctaacagctgtttccctcttctatacatcaggaat ctttgtctatttgagttccagctctggaggttcttcaagctttgacagatttgcatctgttttctacactgtggtca ttcccatgttaaatcccttgatttacagtttgaggaacaaagaaattaaagatgccttaaagaggttgcaaaagaga aagtgctgctgag Protein
                                                           SEQ ID NO: 2
MTGGGNITEITYFILLGFSDFPRIIKVLFTIFLVIYITSLAWNLSLIVLIRMDSHLHTPMYFFLSNLSFIDVCYISS TVPKMLSNLLQEQQTITFVGCIIQYFIFSTMGLSESCLMTAMAYDRYAAICNPLLYSSIMSPTLCVWMVLGAYMTGL
```

-continued

TASLFQIGALLQLHFCGSNVIRHFFCDMPQLLILSCIDTFFVQVMTAILTMFFGIASALVIMISYGYIGISIMKITS

AKGRSKAFNICASHLTAVSLFYISGIFVYLSSSSGGSSSFDRFASVFYIVVIPMLNPLIYSLRNKEIKDALKRLQKR

KCC

Human OR10J5
*Homo sapiens*_OR10J5_Floral muguet receptor
DNA

SEQ ID NO: 3 atgaagagaaagaacttcacagaagtgtcagaattcattttcttgggattttctagctttggaaagcatcagataac cctctttgtggttttcctaactgtctacattttaactctggttgctaacatcatcattgtgactatcatctgcattg accatcatctccacactcccatgtatttcttcctaagcatgctggctagttcagagacggtgtacacactggtcatt gtgccacgaatgcttttgagcctcattttcataaccaacctatctccttggcaggctgtgctacacaaatgttctt ttttgttatcttggccactaataattgcttcctgcttactgcaatggggtatgaccgctatgtggccatctgcagac ccctgagatacactgtcatcatgagcaagggactatgtgcccagctggtgtgtgggtcctttggcattggtctgact atggcagttctccatgtgacagccatgttcaatttgccgttctgtggcacagtggtagaccacttcttttgtgacat ttacccagtcatgaaactttcttgcattgataccactatcaatgagataataaattatggtgtaagttcatttgtga tttttgtgcccataggcctgatatttatctccctatgtccttgtcatctcttccatccttcaaattgcctcagctgag ggctggaagaagaccttttgccacctgtgtctcccacctcactgtggttattgtccactgtggctgtgcctccattgc ctacctcaagccgaagtcagaaagttcaatagaaaaagaccttgttctctcagtgacgtacaccatcatcactccct tgctgaaccctgttgtttacagtctgagaaacaaggaggtaaaggatgccctatgcagagttgtgggcagaaatatt tcttaa Protein

SEQ ID NO: 4

MKRKNFTEVSEFIFLGFSSFGKHQITLFVVFLTVYILTLVANIIIVTIICIDHHLHTPMYFFLSMLASSETVYTLVI

VPRMLLSLIFHNQPISLAGCATQMFFFVILATNNCFLLTAMGYDRYVAICRPLRYTVIMSKGLCAQLVCGSFGIGLT

MAVLHVTAMFNLPFCGTVVDHFFCDIYPVMKLSCIDTTINEIINYGVSSFVIFVPIGLIFISYVLVISSILQIASAE

GWKKTFATCVSHLTVVIVHCGCASIAYLKPKSESSIEKDLVLSVTYTIITPLLNPVVYSLRNKEVKDALCRVVGRNI

S

Mouse Olfr1440
*Mus musculus*_Olfr1440_Musk receptor
DNA

SEQ ID NO: 5 atgcctggagggaggaatagcacagtcatcaccaagttcatccttgtgggattctcagatttttccaaagctcaagct ggttctctttgttatcttcctgggaagttatctctccacagtggtgtggaacttgggcctcatcatcttgattagga ttgaccccttacctacacacacctatgtacttcttcctcagcaatttgtcattttttagatttctgttacatttcatct acaaccctaaaatgctctcgggattcttccagaagtctaaatctatctcctttgttgggtgcaccatgcagtactt catcttctcaagcctgggtctgtccgaatgctgccttctggcagccatggcttatgaccggtatgctgccatttgta atcctcttctctacacagccatcatgtccccgtcactctgtgtgcacatggtggttggagcctatagtactggtctc ttgggttcattgattcaactgtgtgctatacttcagctccatttctgtgggccaaatattataaaccatttcttttg tgacctgcctcagctattagttctttcctgctctgaaacctttcccctgcaagtcttgaaatttgtaatagcagtga ttttgggggtggcatctgtcattgttatcctgatatcctatggttatatcattggcacaatcctgaatatcagctca gtagaaggtaggtccaaggcattcaatacctgtgcctctcacctgacagcagtcaccctctttttggatcaggact ctttgtctatatgcgccccagctccaacagttcccagggttatgacaagatggcttccgtgttctatacagtggtga ttcccatgttgaatcctctgatttatagtctcaggaacaaggaaataaaagatgctcttcagagatgtaaaaataag tgcttttctcagtgccactgttag -continued Protein
SEQ ID NO: 6

MPGGRNSTVITKFILVGFSDFPKLKLVLFVIFLGSYLSTVVWNLGLIILIRIDPYLHIPMYFFLSNLSFLDFCYISS

TTPKMLSGFFQKSKSISFVGCTMQYFIFSSLGLSECCLLAAMAYDRYAAICNPLLYTAIMSPSLCVHMVVGAYSTGL

LGSLIQLCAILQLHFCGPNIINHFFCDLPQLLVLSCSETFPLQVLKFVIAVIFGVASVIVILISYGYIIGTILNISS

VEGRSKAFNTCASHLTAVTLFFGSGLFVYMRPSSNSSQGYDKMASVFYTVVIPMLNPLIYSLRNKEIKDALQRCKNK

CFSQCHC

Mouse Olfr16
Mus musculus_Olfr16_Floral muguet receptor
DNA
SEQ ID NO: 7

Atgcagagaaataacttcactgaagtgatagagttcgtcttcctgggattctccagctttggaaagcatcagataac cctctttgtggttttcctaaccatctacattttaactctggctggcaacatcattatagtgacaatcacacacatag accaccaccttcacactcccatgtacttctttctgagcatgttggcaagctcagagactgtgtacacactggtcatt gtcccacgaatgctttccagcctgatttttacaaccttcccatatccttggcaggctgcgcaacccaaatgttctt ttttgtcaccttggccaccaacaactgctttctgctcacagcaatgggttatgatcgttatgtggctatttgtaatc ctctgagatatacaatcatcatgagcaagggaatgtgtgccttgttggtttgtgggtctttaggcactggcctggtt atggcagttcttcatgtgccagccatgttccatttgccttttgtggcacggtggtggagcacttttctgtgacat atacccagtaatgaagctttcttgtgttgataccactgtcaatgagataatcaattatggtgtaagttcatttgtaa ttcttgtgcccatagggctgatatttatctcctatgtgctcattgtctcttccatccttaaaattgtgtccactgaa ggccagaagaaagcctttgccacctgtgcctctcatctcactgtggtcattgtccactatggctgtgcctccattgc ctacctcaaacccaaatcagaaagttcagtagaaaaagaccttcttctctctgtgacctacactatcatcactccct tgctgaaccctgttgtctacagcctcaggaacaaagaagtcaaagatgctctatgcagagctgtgggcagaaacact tcttaa Protein
SEQ ID NO: 8

MQRNNFTEVIEFVFLGFSSFGKHQITLFVVFLTIYILTLAGNIIIVTITHIDHHLHTPMYFFLSMLASSETVYTLVI

VPRMLSSLIFYNLPISLAGCATQMFFFVTLATNNCFLLTAMGYDRYVAICNPLRYTIIMSKGMCALLVCGSLGTGLV

MAVLHVPAMFHLPFCGTVVEHFFCDIYPVMKLSCVDTIVNEIINYGVSSFVILVPIGLIFISYVLIVSSILKIVSTE

GQKKAFATCASHLTVVIVHYGCASIAYLKPKSESSVEKDLLLSVTYTIITPLLNPVVYSLRNKEVKDALCRAVGRNT

S

FLAG tag
DNA
SEQ ID NO: 9
gattacaaggacgacgacgataag

Protein
SEQ ID NO: 10
DYKDDDDK

Rho tag
DNA
SEQ ID NO: 11
atgaacgggaccgagggcccaaacttctacgtgcctttctccaacaagacgggcgtggtg Protein
SEQ ID NO: 12
MNGTEGPNFYVPFSNKTGVV Lucy tag
DNA
SEQ ID NO: 13
atgagaccccagatcctgctgctcctggccctgctgaccctaggcctggct protein
SEQ ID NO: 14
MRPQILLLLALLTLGLA -continued Motif

MAYDRYVAIC

SEQ ID NO: 15

Motif

FSTCSSH

SEQ ID NO: 16

Motif

PMLNPFIY

SEQ ID NO: 17

The following examples are illustrative only and are not meant to limit the scope of invention as set forth in the Summary, Description or in the Claims.

EXAMPLES

Example 1: Identification of Odorant Receptors Relevant to Sensory Outcome

Various target compounds (e.g. musky, floral, or woody ingredients) of importance to perfumery are chosen. The method as described in WO2014/210585 can be used to identify a relatively small subset of ORs within the entire repertoire of ORs that exist in an organism that are specifically activated or inhibited by one or more of these compounds. Transcriptomic analyses such as NGS approaches or proteomics analyses such as mass spectrometry represent additional means to identify ORs ex vivo. Alternatively, in vivo approaches such as the DREAM method allow for OR deorphanization upon gas phase delivery of volatile compounds [Von Der Weid B. et al., Nature neuroscience, 18(10):1455-63 (2015)].

Olfactory receptors can be evaluated to determine whether the psychophysical (sensory) outcome of the target compound perception could be correlated to the target compound-induced activity in vitro. Such olfactory receptors that seemingly have a predictive power with respect to putative sensory outcome are chosen for further screening for target compound directed receptor-based enhancement. Alternatively, olfactory receptors activated by particular agonists of interest to perfumery are chosen. The particular target receptor-agonist pair is used in assays or methods for screening and identifying positive allosteric modulator compounds of the target agonist.

Example 2: Identification of a Musk Olfactory Receptor

The musk compounds muscone, MUSCENONE®, musk xylol and musk ketone formed a highly correlated group with respect to mean odor detection thresholds at the sensory level. To test whether the sensory correlation observed between the four musk compounds was linked to a single odorant receptor's activity, the response of the OR5AN1 olfactory receptor to musk compounds was evaluated. The receptor specificity and the sensitivity values observed were compared to the human psychophysical (sensory) odor detection threshold data (FIG. 1).

The OR5AN1 olfactory receptor was specifically activated by muscone, MUSCENONE®, musk xylol and musk ketone. However, none of the other musk compounds tested were able to activate the OR5AN1 olfactory receptor. See FIG. 1a.

The observed musk receptor (FIG. 1a) and psychophysical (FIG. 1b) activity rankings were the same when considering the Pearson correlation for the mean or the median odor detection threshold values (sensory outcome) obtained for the musk compounds with either the ligand potency ($EC_{50}$ values) or efficacy (maximum span) of OR5AN1 olfactory receptor activity.

The psychophysical measures showed a strong direct correlation with $EC_{50}$ and an even stronger correlation with the efficacy (r=0.87 and r=−0.91, respectively) with the median odor detection thresholds. Similar correlation values were obtained with the mean odor detection thresholds. Both the median and the average sensitivity obtained at the group level followed the potency and the efficacy ranking obtained in vitro (Table 1).

TABLE 1

Musk ranking by pharmacological potency on OR5AN1 and perceptual detection threshold.

| Rank order | Odorant name | EC50 [a] Log(M) | Span [b] (HTRF ratio) | Median odor detection threshold Log (μmol/l air) | Mean odor detection threshold Log (μmol/l air) |
|---|---|---|---|---|---|
| 1. | Musk ketone | $2.56e^{-8}$ | 4312 | $6.41e^{-9}$ | $6.11e^{-9}$ |
| 2. | Musk xylol | $3.57e^{-7}$ | 4217 | $1.02e^{-8}$ | $2.20e^{-8}$ |
| 3. | Muscenone ® | $2.01e^{-6}$ | 3629 | $1.04e^{-7}$ | $1.26e^{-7}$ |
| 4. | Muscone | $3.29e^{-6}$ | 2979 | $1.09e^{-6}$ | $1.21e^{-6}$ |

[a] EC50 Pearson correlation to Median, r = 0.866177 and to Mean, r = 0.869362
[b] Span Pearson correlation to Median, r = −0.91012 and to Mean, r = −0.91267

In other words, the receptor activation profile fully recapitulated the psychophysical data and was sufficient to explain the observed sensory correlation between musk compounds. Accordingly, OR5AN1 represents a good target for musk directed receptor-based enhancement screening. Identifying further sensory key target receptors enables the screening for enhancement of additional perfumery tonalities (e.g. musky, floral, woody, marine).

Example 3: Identification of Putative OR5AN1 Activity Enhancers

Using a cell-based assay, OR5AN1 was tested in an HEK293T cell line wherein the endogenous RTP1 gene has been activated and the odorant receptor chaperone was expressed (WO2016/201153 A1). The Flag-Rho-tagged receptor was co-transfected with the olfactory canonical G-protein $G_{olf}$ and was exposed to a binary mixture of a single concentration of MUSCENONE® and a test compound.

A large library of volatile compounds was used to create binary mixtures of each compound with MUSCENONE® at ~$EC_{10}$, a concentration eliciting only a ~10% of full activity level of OR5AN1 by itself. An activation cell-based assay was used for the initial enhancer candidate identification. Single binary mixture-induced receptor activity was detected by measuring the cAMP increase in the cytosol using an HTRF (Homogenous Time-Resolved Fluorescence unit) based kit (CisBio, cAMP dynamic 2 kit, 62AM4PEJ).

Figure 2:
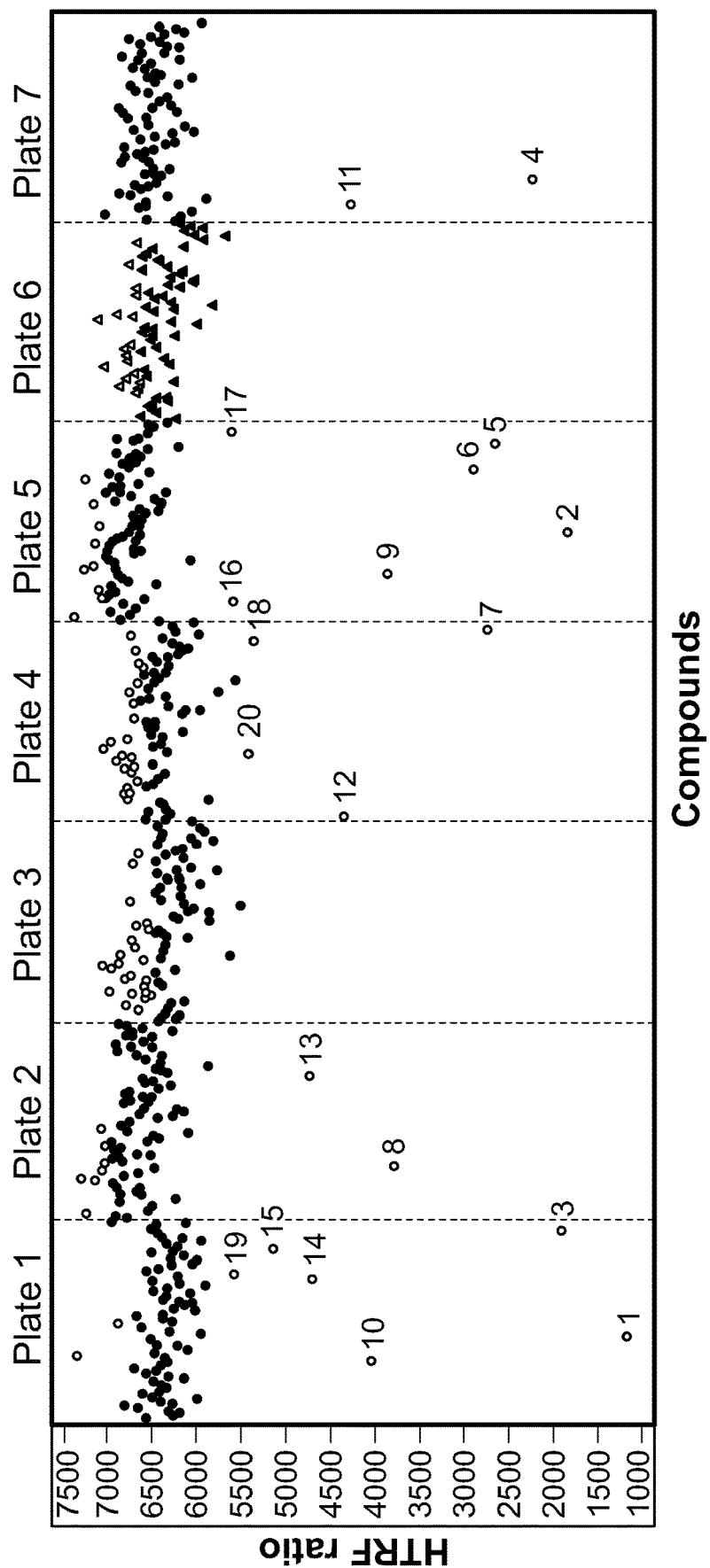
FIG. 2 shows the result of a single point binary mixture of MUSCENONE® and perfumery raw materials screening for OR5AN1 Musk-induced activity enhancement.

481 binary mixtures were created by mixing a MUSCENONE® stock solution with a stock solution of each test compound to a final concentration 10 and 500 PM, respectively. Stock solutions were made of compounds dissolved in pure DMSO. Each mixture was presented to a cell line expressing the OR5AN1 olfactory receptor. In FIG. 2, mixtures are represented by dots (●), empty wells in plate 6 by triangles (▲). The final concentration of DMSO in each binary mixture was 0.17%, and had no visible effect on the cells.

The resulting activation was then measured and compared to MUSCENONE® alone (defining the baseline of the enhancement assay). The quality of the HTS process was determined and the window variability and signal reliability were assessed by calculating the Z' value of each plate. Twenty hits were obtained, five of which were macrocyclic ketone and nitromusk OR5AN1 olfactory receptor agonists (hit no 1, 2, 3, 5 and 9). See FIG. 2 and Table 2. These OR5AN1 olfactory receptor agonists further confirmed that the dynamic range of the assay window was sufficient (as the responses recorded were well above baseline) and thus likely sensitive enough to detect even low levels of putative enhancement.

15 candidates, marked as "enhancement" in Table 2 were identified. Strikingly, 80% of these putative enhancers (12/15) belonged to the same class of chemicals: unsaturated aliphatic aldehydes. Next, two parallel dose-response experiments to confirm the true enhancement properties of the potential candidates were performed. First, a dose-response of each individual candidate was performed to determine if it was an agonist by itself. Second, a MUSCENONE® dose-response curve in the presence and absence of a 250 μM concentration of the putative modulator was assessed for $EC_{50}$ shifts. Molecules that increased the response of the OR5AN1 olfactory receptor to MUSCENONE® but did not display measurable intrinsic agonist activity themselves were considered to be true enhancers and were selected for further studies.

TABLE 2

Compounds selected from the enhancement screen, numbered by decreasing OR5AN1 activity (span).

| | Molecules | Hit Type |
|---|---|---|
| 1 | 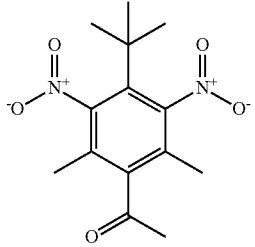 Musk Ketone Pur | Agonist |
| 2 | Chiral 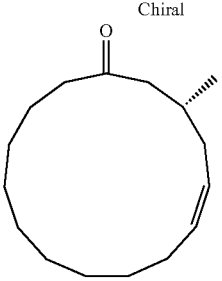 Dextro Muscenone | Agonist |
| 3 | 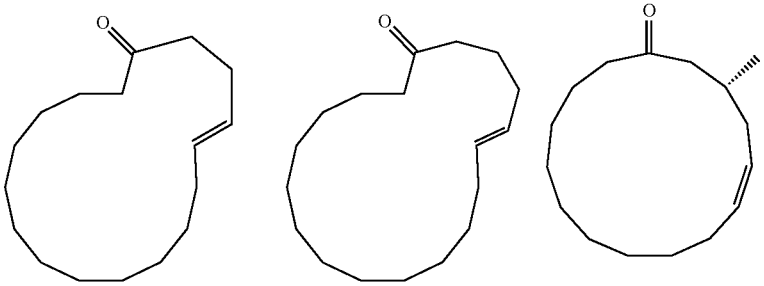 Muscenone Delta | Agonist |

TABLE 2-continued

Compounds selected from the enhancement screen, numbered by decreasing OR5AN1 activity (span).

| | Molecules | Hit Type |
|---|---|---|
| 4 | Pelargodienal | Enhancement |
| 5 | Musc X | Agonist |
| 6 | Nonylenic Aldehyde | Enhancement |
| 7 | Octenal, 2- | Agonist |
| 8 | decadienal, E2, E4- | Enhancement |
| 9 | Muscenone Laevo (Chiral) | Agonist |
| 10 | Dodecenal | Enhancement |
| 11 | 2-Decenal | Enhancement |
| 12 | N302 | Enhancement |
| 13 | Tridecylenic Aldehyde | Enhancement |

US 11,921,105 B2
TABLE 2-continued
Compounds selected from the enhancement screen, numbered by decreasing OR5AN1 activity (span).
| | Molecules | Hit Type |
|---|---|---|
| 14 | 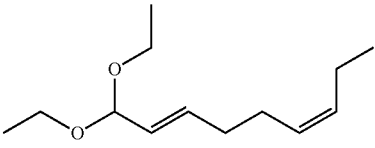<br>Nonadienal dea | Enhancement |
| 15 | 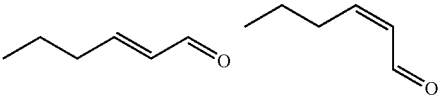<br>Hexenal, 2- | Enhancement |
| 16 | 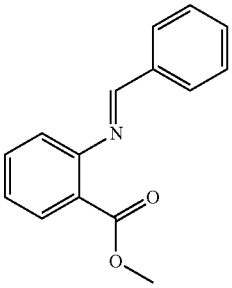<br>Amadolene Pur | Enhancement |
| 17 | 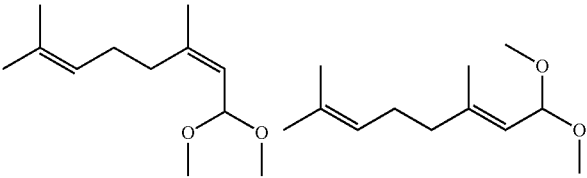<br>Citral Dimethylacetal | Enhancement |
| 18 | 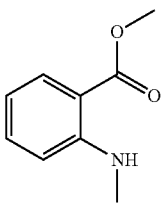<br>Methyl n-methyl-anthranylate | Enhancement |
| 19 | 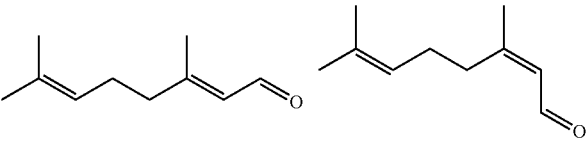<br>Neral & Geranial | Enhancement |

TABLE 2-continued

Compounds selected from the enhancement screen, numbered by decreasing OR5AN1 activity (span).

| | Molecules | Hit Type |
|---|---|---|
| 20 | 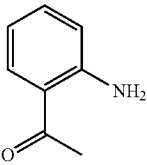
Ortho Amino-cetophenone | Enhancement |

From this analysis, the volatile tridecylenic aldehyde (TDA), an aliphatic α-β mono-unsaturated aldehyde was identified. This compound did not activate the OR5AN1 olfactory receptor by itself but in combination with MUS-CENONE® yielded a clear enhancement effect compared to MUSCENONE® alone. See FIG. 3.

Tridecylenic aldehyde appeared to be an effective enhancer of the OR5AN1 olfactory receptor. The addition of TDA at 250 μM led to a drastic reduction in the MUSCENONE® $EC_{50}$ (an approximate 21 fold shift) and to an overall greater maximal activation level (increased span) (FIG. 3a). When tested by itself, TDA did not display any significant activity aside from very minor binding activity above approximately 100 μM. At this concentration, the binding of TDA yielded an activation of less than 8% of the MUSCENONE® activation window. Tridecylenic aldehyde is therefore not considered a true agonist of OR5AN1.

The effect of TDA on musk compound-induced activation of the OR5AN1 olfactory receptor was observed with muscone, musk xylol and musk ketone. All agonists exhibited comparable leftward dose-response curve shifts in the presence of a 250 μM concentration of TDA (FIG. 3b-d). This indicated that the enhancement was mediated through a receptor binding event and not likely mediated by OR5AN1-independent effects such as on the assay cells themselves. The decrease in $EC_{50}$ ranged between 13 and 28 fold in repeat experiments (FIG. 4). The apparent enhancement observed with binary mixtures of musk and TDA is inconsistent with a binding of competitive nature, mainly because TDA, which is not an agonist, also does not act as an antagonist. Rather, this type of data is indicative of a non-competitive binding site for TDA.

Tables 3a and 3b below reports the effect of additional compounds on the $EC_{50}$ and span of MUSCENONE®.

TABLE 3a

| | $EC_{50}$ (Potency Fold Shift) Concentration of Enhancer (μM) | | |
|---|---|---|---|
| Compound (Enhancer) | 600 | 200 | 66.6 |
| 1 (2E)-7,8-dimethyl-2,7-nonadienal | 3.99 | 9.03 | 1.52 |
| 2 methyl(5E)-7-oxo-5-heptenoate | 4.29 | 2.16 | 1.18 |
| 3 (2E)-7-methyl-2,6-octadienal | 29.14 | 5.60 | 1.36 |
| 4 (2E)-6,6-dimethyl-2-heptenal | 6.88 | 3.30 | 1.15 |
| 5 (+−)-(2E)-5,9-dimethyl-2,8-decadienal | 9.07 | 9.56 | 1.84 |

TABLE 3a-continued

| | $EC_{50}$ (Potency Fold Shift) Concentration of Enhancer (μM) | | |
|---|---|---|---|
| Compound (Enhancer) | 600 | 200 | 66.6 |
| 7 (E)-2-tetradecenal | 7.13 | 5.06 | 3.34 |
| 8 4-hydroxy-2-nonenal | 4.99 | n/a | 1.30 |
| 9 Trans-2,6,7-dimethyl-2,6-octadienal | n/a | 4.47 | 1.18 |

TABLE 3b

| | Span (Efficacy Fold Shift) Concentration of Enhancer (μM) | | |
|---|---|---|---|
| Compound (Enhancer) | 600 | 200 | 66.6 |
| 1 (2E)-7,8-dimethyl-2,7-nonadienal | 1.24 | 1.31 | 1.07 |
| 2 methyl(5E)-7-oxo-5-heptenoate | 1.18 | 1.15 | 0.99 |
| 3 (2E)-7-methyl-2,6-octadienal | 1.18 | 1.20 | 1.06 |
| 4 (2E)-6,6-dimethyl-2-heptenal | 1.14 | 1.02 | 1.06 |
| 5 (+−)-(2E)-5,9-dimethyl-2,8-decadienal | 1.15 | 1.22 | 1.02 |
| 7 (E)-2-tetradecenal | 1.04 | 1.00 | 0.94 |
| 8 4-hydroxy-2-nonenal | 1.09 | 1.32 | 1.00 |
| 9 Trans-2,6,7-dimethyl-2,6-octadienal | 1.03 | 1.13 | 1.05 |

Example 4: Tridecylenic Aldehyde Acts as Positive Allosteric Modulators (PAM) to Enhance OR5AN1 Olfactory Receptor Activity Functional dose-response experiments were performed to reveal the allosteric nature of the interaction between tridecylenic aldehyde (TDA) and OR5AN1. The level of enhancement of OR5AN1's activation was evaluated at distinct concentrations of the enhancer. Using the same cell-based assay described above, dose response curves of OR5AN1 to MUSCENONE® in the presence of serial concentrations of tridecylenic aldehyde spanning from 0 to 1 mM were performed. The curves were obtained by applying the simplified Allosteric EC50 shift effect equation (available in Prism5, v. 5.02) derived from the ternary complex interaction model. The enhancement levels recorded were not linearly dependent on the concentration of the enhancer, and the following key parameters values for a (the cooperativity factor) and $K_B$ (the equilibrium dissociation constant of TDA) obtained from the model: α=15.7 and $K_B$=259 μM. α>1 is indicative of positive allosteric modulation. Following this method, 2-decenal and nonylenic aldehyde, two potent enhancers, exhibited allosteric modulation properties similar to TDA with the following key parameters: 2-decenal, $\alpha=37.3$ and $K_B=264$ µM; Nonylenic aldehyde, $\alpha=28.8$ and $K_B=96$ µM.

Full pharmacological characterization of the enhancers provides a means to rank order the enhancers based on 1) the potency shift they induce when in combination with a perfumery ingredient (e.g. musky, floral or woody ingredients), 2) the efficacy (the activity level of the target receptor) increase compared to the efficacy observed with the compound alone, 3) the affinity of the enhancing compound for the receptor, 4) the minimal concentration necessary for enhancement to occur, and/or 5) the most efficient ratio of enhancer to perfumery compound that leads to the greatest enhancement performance.

Figure 5B:
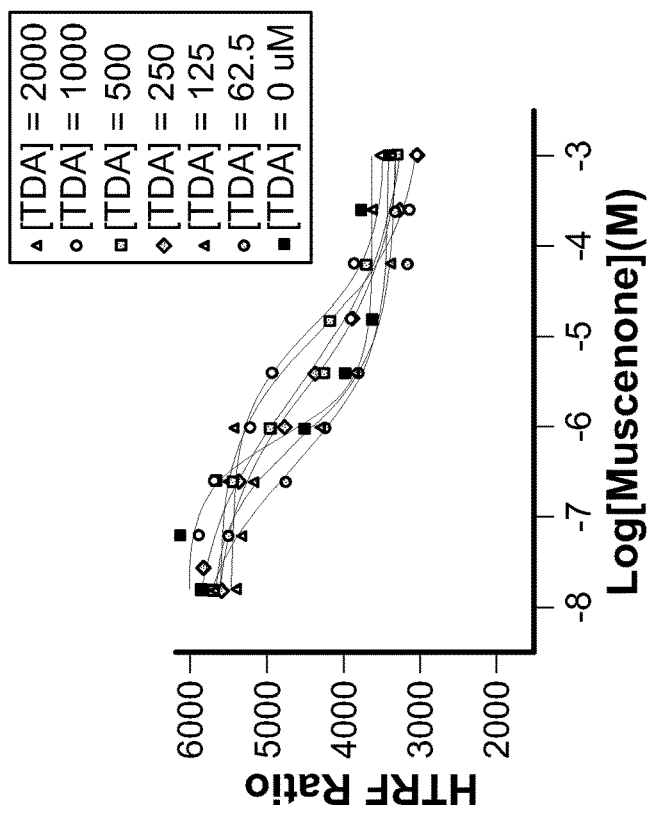
FIG. 5 displays a series of dose response curves of OR5AN1 to MUSCENONE® in the presence of serial concentrations of tridecylenic aldehyde and also indicates the calculated log values for the cooperativity factor α and the equilibrium constant KB.
Figure 5A:
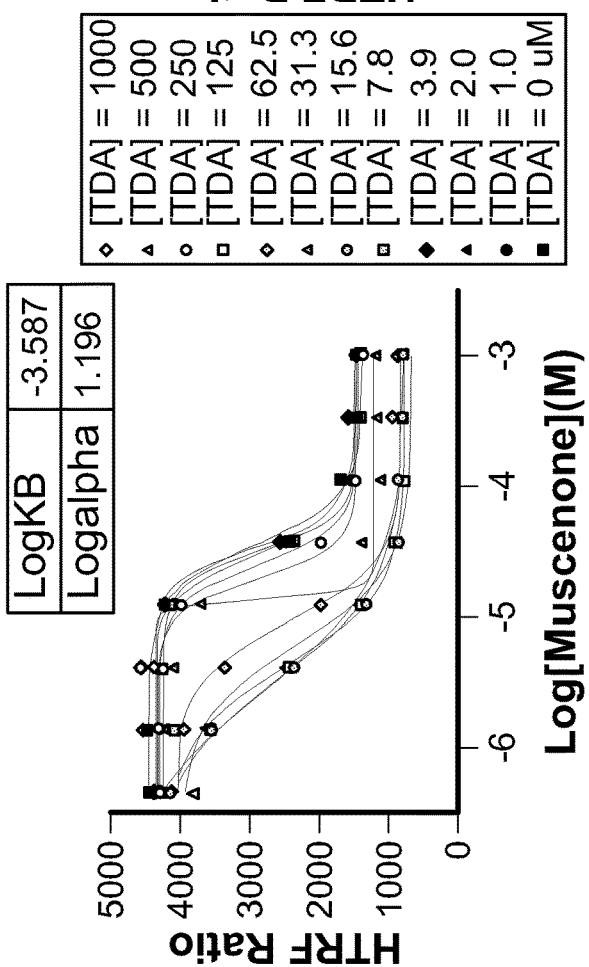

Furthermore and as a control, a similar experiment was performed on the mouse MUSCENONE® responsive odorant receptor Olfr1440, the ortholog of OR5AN1. Tridecylenic did not enhance the activity of the Olfr1440 receptor. Rather, the aldehyde led to a slight inhibition of the Olfr1440 MUSCENONE®-induced activation (FIG. 5). This further supports the view that enhancement of OR5AN1 by tridecylenic aldehyde is receptor-mediated and receptor-specific.

Example 5: The Structure-Activity Relationship of Positive Allosteric Modulators of the OR5AN1 Olfactory Receptor A chemically diverse set of 67 volatile compounds structurally related to the aliphatic unsaturated aldehydes found initially (see Example 2 and FIG. 1) was generated for structure-activity-relationship (SAR) analysis. The sixty-seven molecules were tested for their enhancement properties on OR5AN1 to characterize the necessary chemical requirements.

Dose response curves to MUSCENONE® were obtained in the presence of 250 µM of each compound and compared to a dose-response curve of MUSCENONE® alone. The resulting enhancement was quantified by means of $EC_{50}$-fold shift (potency increase) and the efficacy span ratio (efficacy increase).

The $EC_{50}$-fold shift was obtained by dividing the $EC_{50}$ of MUSCENONE®+compound by the reference $EC_{50}$ MUSCENONE® alone. The span ratio was obtained by dividing the span of MUSCENONE®+compound by the reference span of MUSCENONE® alone. Specifically, diverse aliphatic α-β mono- or poly-unsaturated molecules have been compared.

α-β-mono-unsaturated disubstituted aliphatic aldehydes were systematically found to exhibit the most potent enhancement. Functional group replacement, saturation modification and additional substitutions appear to reduce or eliminate the potential of that compound to enhance the receptor (FIGS. 6, 8-12). Additional modifications around the α-β mono-unsaturated aliphatic aldehydes such as substitution at the α position or cyclisation of the aliphatic tail prevented enhancement effects to take place.

Figure 7:
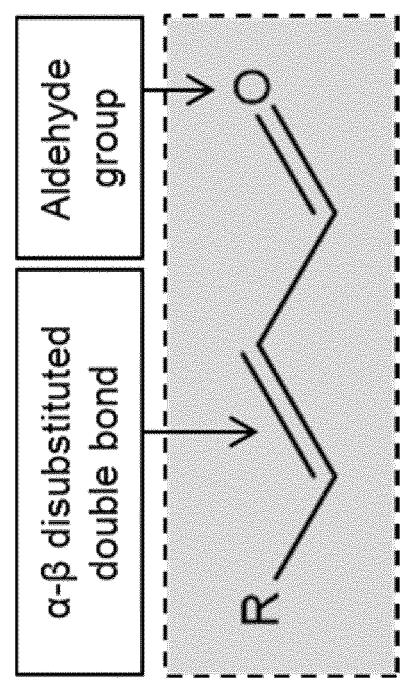
FIG. 7 depicts the chemical requirements identified from the SAR analyses that are preferred to elicit OR5AN1 Musk response enhancement.
Figure 9B:
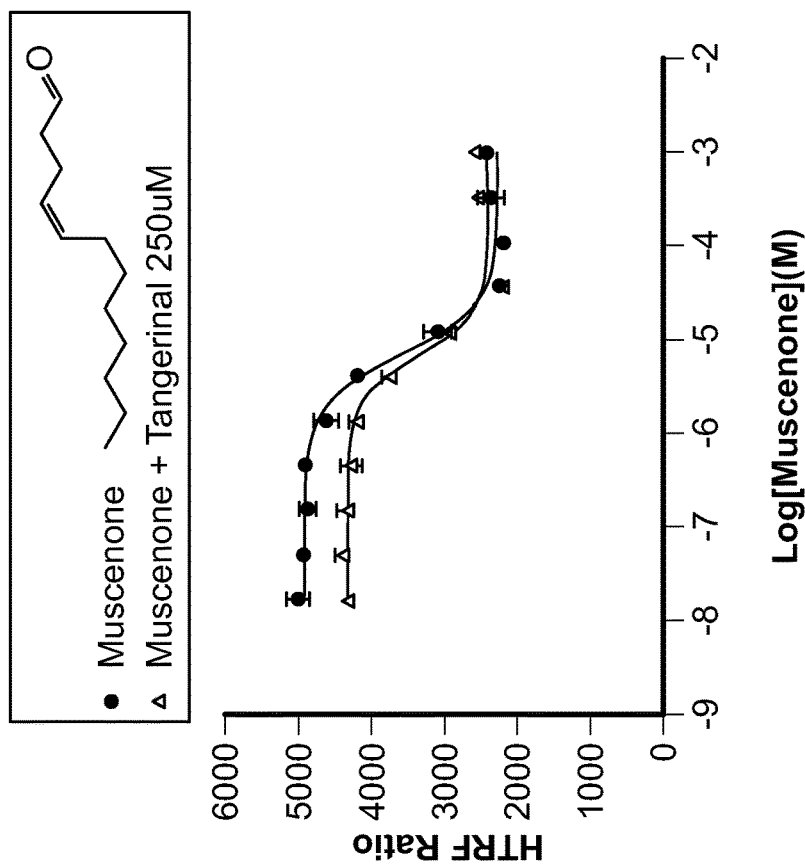
FIG. 9 shows the distinct enhancement levels obtained on OR5AN1 with a) dodecenal and b) tangerinal, and the importance of the unsaturation position.
Figure 9A:
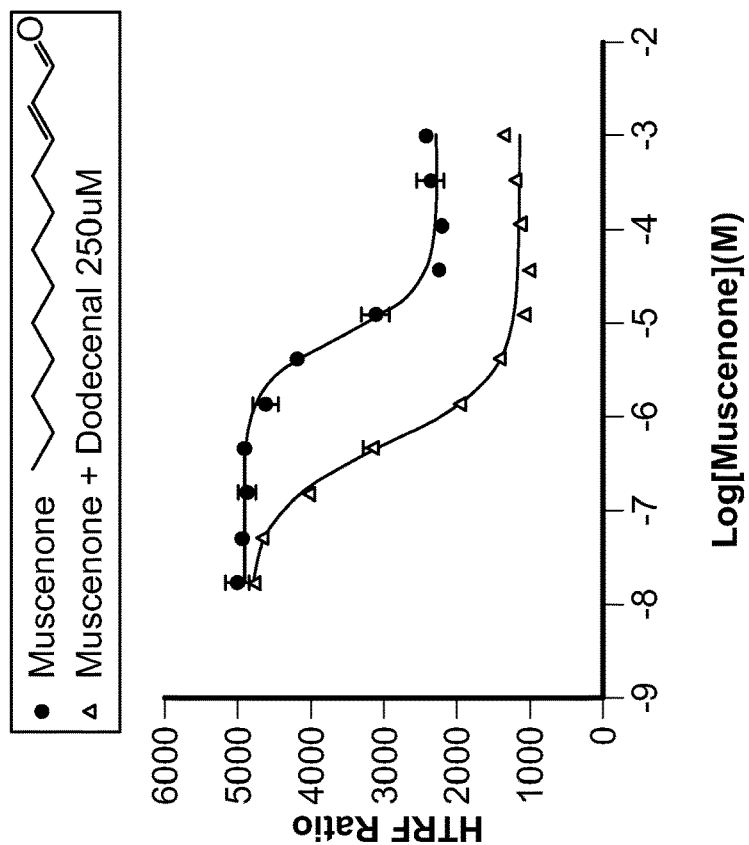

A resulting generic chemical structure showing the required chemical features for specific OR5AN1 enhancing has been determined (FIG. 7). Pairwise comparisons of the dose-response curves obtained with the α-β-mono-unsaturated aldehydes and derived saturational or functional isomers further exemplifies the necessary chemical features required for OR5AN1 enhancement (FIGS. 8-12). FIG. 8 shows the distinct enhancement levels obtained with decenal, decadienal and decanal, and the requirement of the unsaturation. FIG. 9 shows the distinct enhancement levels obtained with dodecenal and tangerinal, and the importance of the unsaturation position.

Figure 11B:
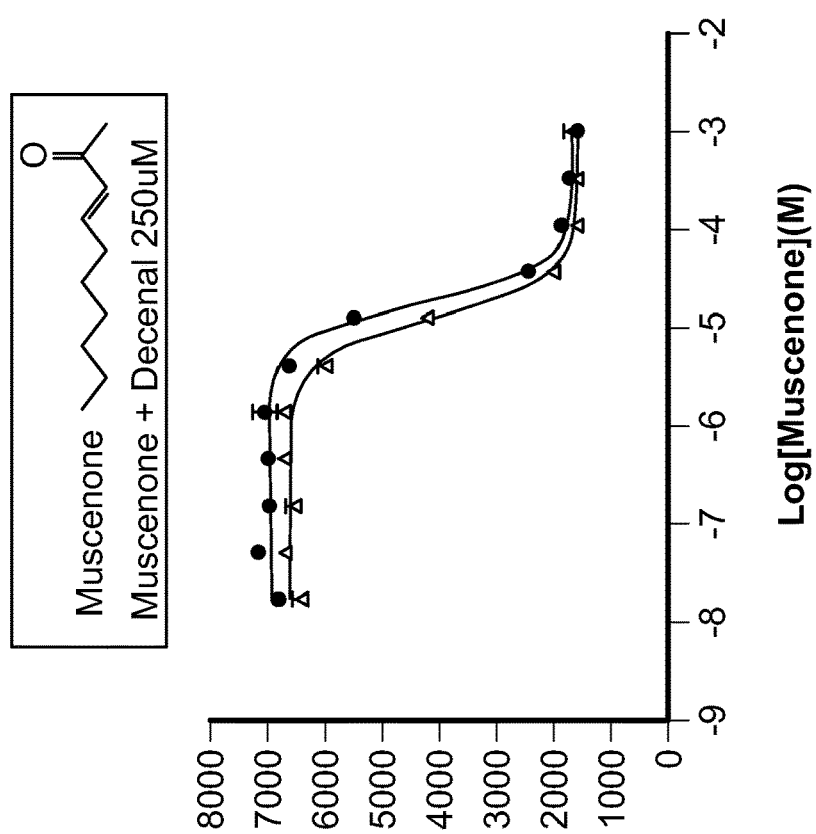
FIG. 11 shows the distinct enhancement levels obtained on OR5AN1 with a) decenal and b) decenone, and the absence of enhancement with a ketone functional group.
Figure 11A:
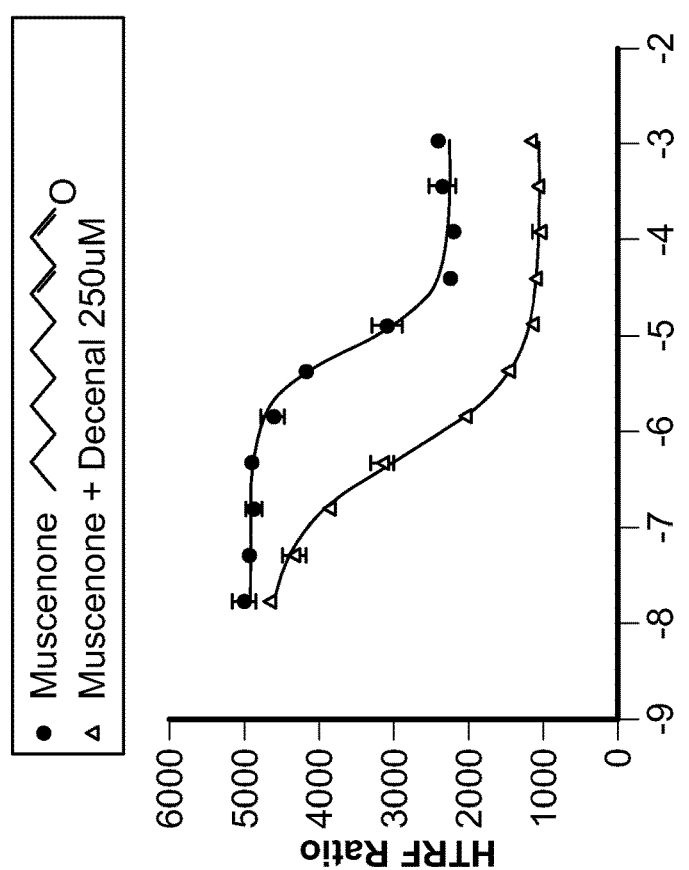
Figure 12B:
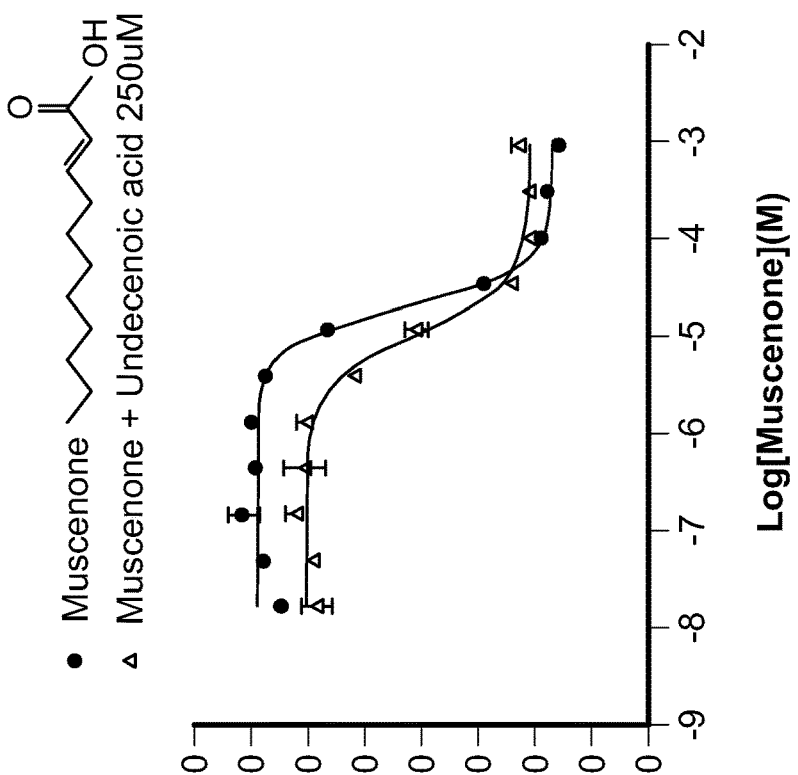
FIG. 12 shows the distinct enhancement levels obtained on OR5AN1 with a) undecenal and b) undecenoic acid, and the absence of enhancement with an acid group.
Figure 12A:
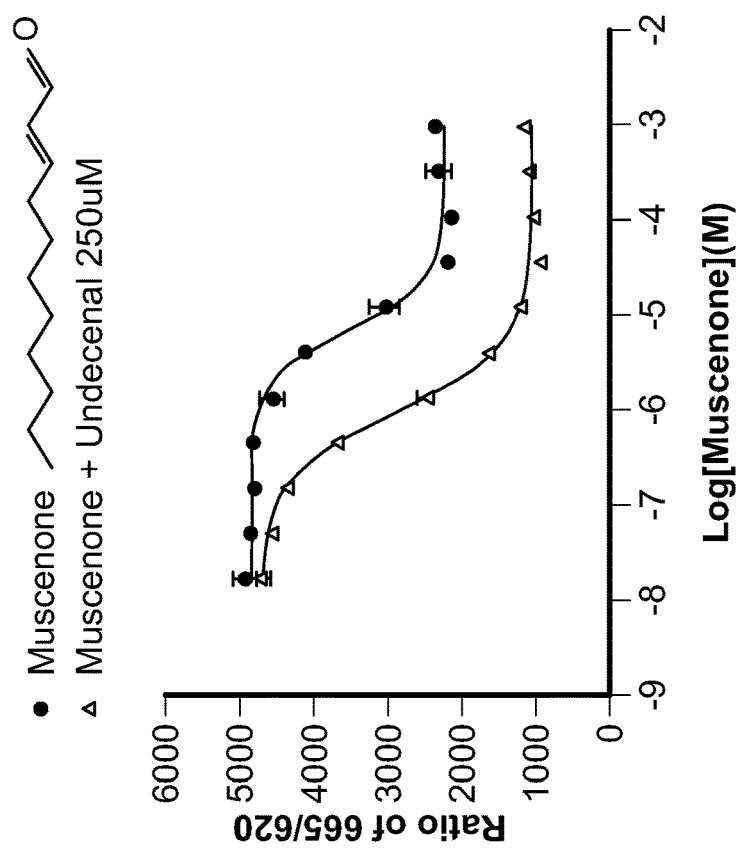

FIG. 10 shows the distinct enhancement levels obtained with nonylenic aldehyde, nonenol and nordecenol, and the absence of enhancement when an alcohol functional group is used instead of an aldehyde group. FIG. 11 shows the distinct enhancement levels obtained with decenal and decenone, and the absence of enhancement when a ketone functional group is used. And FIG. 12 shows the distinct enhancement levels obtained with undecenal and undecenoic acid, and the absence of enhancement when an acid functional group is used.

A SAR analysis was conducted to identify the best enhancers and determine the chemical requirements needed for compounds that enhanced a given receptor. In the case of OR5AN1, at least 10 potent enhancers have been identified, all of which are volatile compounds applicable to perfumery creation/design. Without intending to be limited to any particular theory, when several enhancers are at hand for creation, a subsequent organoleptic characterization of their inherent smell further allows selecting the volatile compounds that best fit downstream applications with respect to the overall tonality of the application (i.e. a perfume). In other words, an enhancing ingredient portfolio corresponding to each target molecule, for example, musk, is generated and provides perfumers with more creation tools.

Example 6: Hypofunctional OR Alleles can be Restored in the Presence of an Enhancer Olfactory receptors are frequently encoded by several alleles for any given OR gene, from a single allele to over fifteen alleles. Natural allelic variations can range from about 1% to 5% in the nucleotide sequence of a gene or in the amino acid sequence of the polypeptide it encodes.

Five OR5AN1 alleles are known to be present in human populations. These alleles are functionally not equivalent and exhibit distinct activity levels ranging from fully functional (allele 1 and 2), hypofunctional (allele 3 and 4) to loss-of function (allele 5) (FIG. 13).

Testing the hypofunctional OR5AN1 allele 3 and 4 in a cell-based assay in the presence and in the absence of the identified enhancer tridecylenic aldehyde showed a substantial increase in the activity level. The observed $EC_{50}$ value for OR5AN1 allele 3 exhibited a 6.0 fold shift (from 9.0 µM to 1.5 µM in the presence of 250 µM tridecylenic aldehyde) and an activity span-ratio of 2.02 (with an activity increase from 2311 to 4663 relative fluorescent HTRF units in the presence of tridecylenic aldehyde). The observed $EC_{50}$ value for OR5AN1 allele 4 exhibited a 6.25 fold shift (from 10.1 µM to 1.6 µM in the presence of 250 µM tridecylenic aldehyde) and an activity span-ratio of 2.16 (with an activity increase from 2328 to 5026 relative fluorescent HTRF units in the presence of tridecylenic aldehyde). Both potency and efficacy shifted favorably and led to an activity level more comparable to the presumably stronger activity elicited by MUSCENONE® for people carrying allele 2. These data suggest that individuals carrying these alleles may be more sensitive to a perfumery application containing an OR5AN1 activating musk in the presence of an enhancing perfumery ingredient.

Example 7: Human Sensitivity to a Musk Compound is Increased in the Presence of an Enhancer Sensitivity of human individuals to MUSCENONE® was evaluated by performing an odor detection threshold (ODT)

test. The ODT test consisted of identifying the concentration for which 50%, preferably 66%, of the panelists are able to determine which of three containers contains the target compound MUSCENONE® in a forced-choice triangle tests. Two tests were performed to calculate the ODT in mixtures containing MUSCENONE® plus a perceivable background odor of chemically similar molecules a) the enhancer tridecylenic aldehyde and b) the non-enhancing volatile compound, nonanal. These two molecules are chemically similar but nonanal does not exhibit the necessary α-β-unsaturation for enhancement to occur identified in Example 5.

Figure 14:
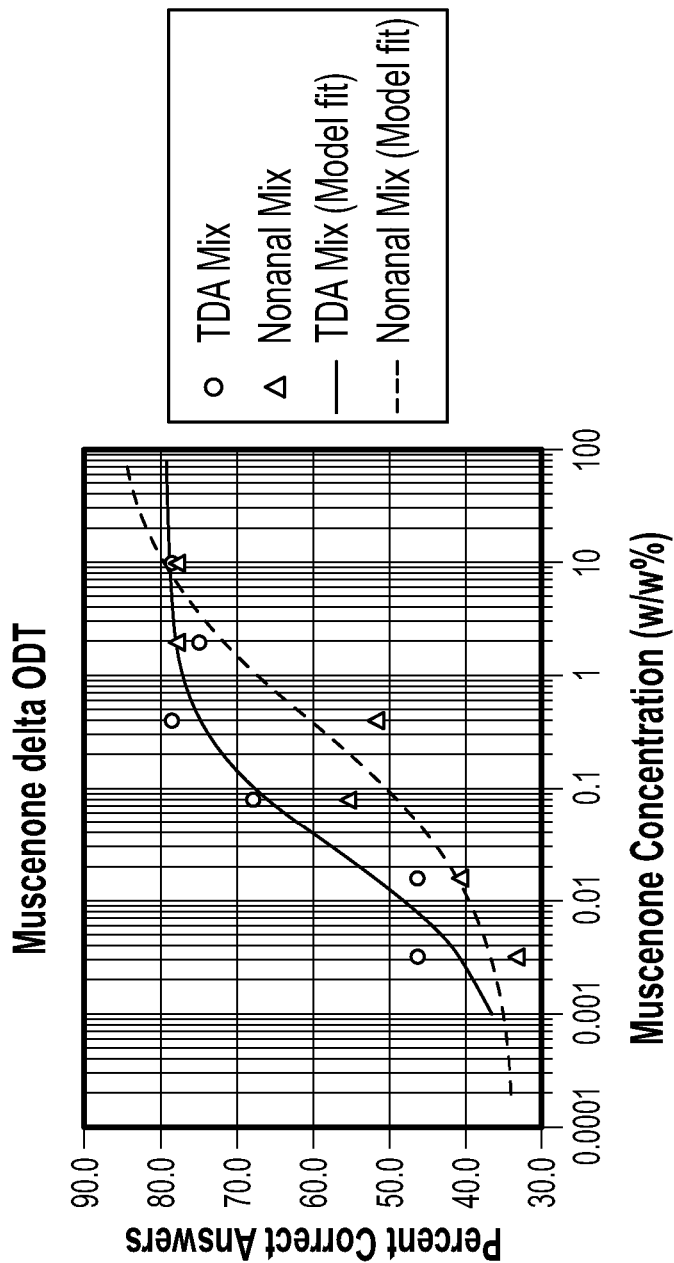
FIG. 14 shows human panelists more sensitive to MUSCENONE® in the presence of an enhancer compared to a non-enhancing compound.

28 panelists were given a series of triangle tests with increasing concentrations of MUSCENONE® in the presence of tridecylenic aldehyde at a concentration of 0.1%. Within each triangle test, the three samples contained tridecylenic aldehyde at 0.1% and one sample also contained MUSCENONE®. 27 panelists were given a series of triangle tests with increasing concentration of MUSCENONE® in the presence of nonanal at a concentration of 0.1%. Within each triangle test, the three samples contained nonanal at 0.1% and one sample also contained MUSCENONE®. In each triangle test, the panelists were asked to identify the one sample that was different from the other two samples. The ODT was calculated by fitting a non-linear regression model onto the data and calculating the MUSCENONE® concentration at which the proportion of correct responses was equal to 2/3 (66%, the midpoint between chance rate 1/3 and all correct answers 1). There was a lower ODT value when the musk was mixed with the enhancer than with the neutral compound: 0.09% compared to 0.93%, respectively, indicating distinct musk detection levels under experimentally similar conditions (FIG. 14).

Example 8: Identification of Putative OR10J5 Activity Enhancers

Following the same screening method as described in Examples 1 to 5, a human floral muguet odorant receptor, OR10J5, is screened to identify putative enhancers. The Lucy-Flag-Rho-tagged receptor is co-transfected with the olfactory canonical G-protein Golf and exposed to a binary mixture of a single concentration of a floral muguet compound and a test compound.

Figure 15:
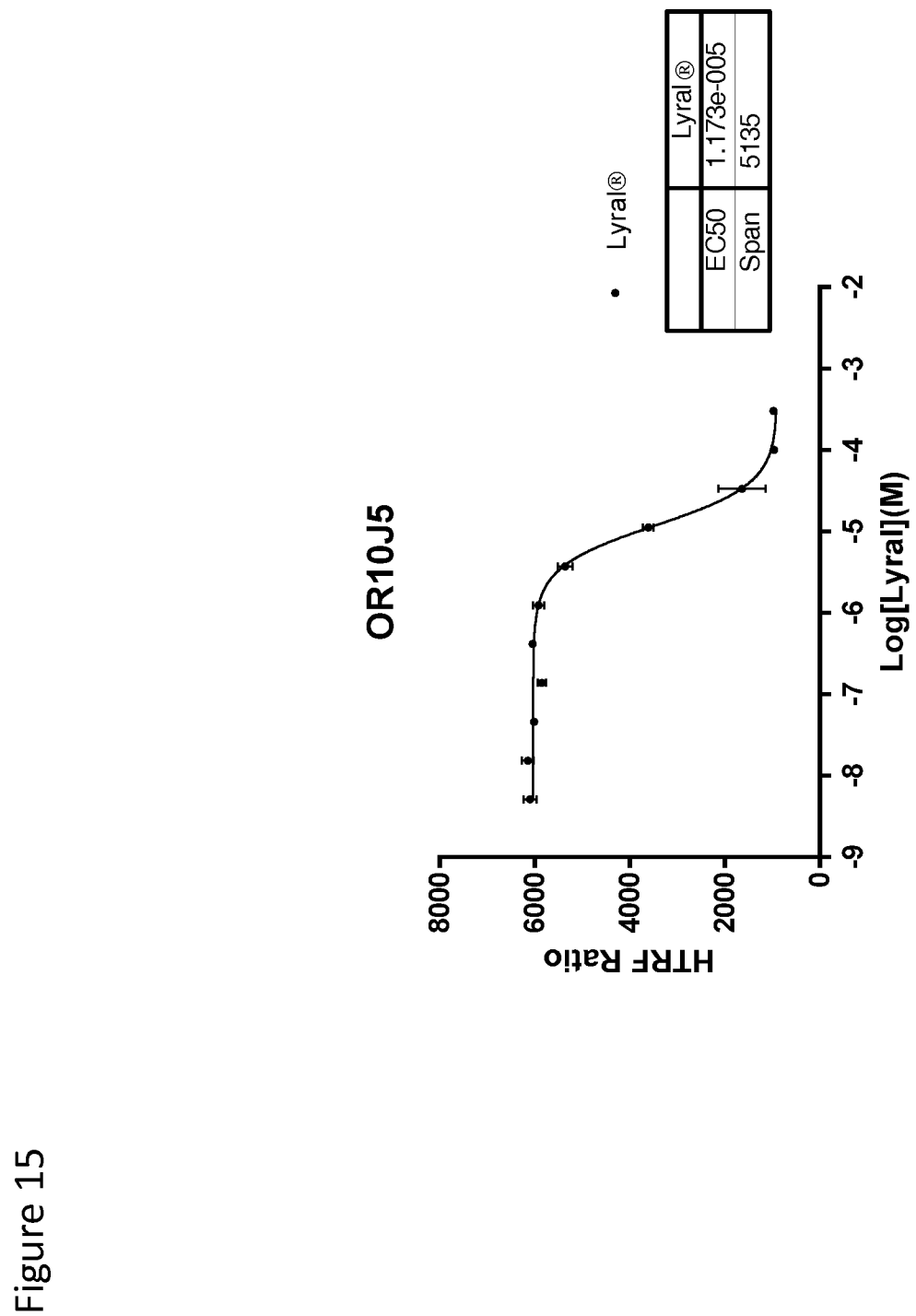
FIG. 15 shows a dose-response curve of OR10J5 to the floral muguet compound LYRAL®.

A dose response curve showing the activation of OR10J5 in response to the floral muguet compound 33-(4-hydroxy-4-methylpentyl)cyclohex-3-ene-1-carbaldehyde, 4-(4-hydroxy-4-methylpentyl)cyclohex-3-ene-1-carbaldehyde or a mixture thereof (sold under the tradename LYRAL®, hereinafter referred to as "LYRAL®") is shown in FIG. 15. Using a cell-based assay, OR10J5 activity was tested in a HEK293T cell line wherein the endogenous chaperone RTP1 gene has been activated and the odorant receptor chaperone was expressed according to the methods disclosed in International Patent Application Publication No. WO2016/201153 A1. The Flag-Rho-tagged receptor was co-transfected with the olfactory canonical G-protein Golf and was exposed to a binary mixture of a single concentration of LYRAL® and a test compound.

A library of volatile compounds was used to create binary mixtures of each compound with LYRAL® at approximately $EC_{20}$, a concentration eliciting only approximately 20% of full activity level of OR10J5 by itself. An activation cell-based assay was used for the initial enhancer candidate identification. Single binary mixture-induced receptor activity was detected by measuring the cAMP increase in the cytosol using an HTRF (Homogenous Time-Resolved Fluorescence unit) based kit (CisBio, cAMP dynamic 2 kit, 62AM4PEJ).

Figure 16:
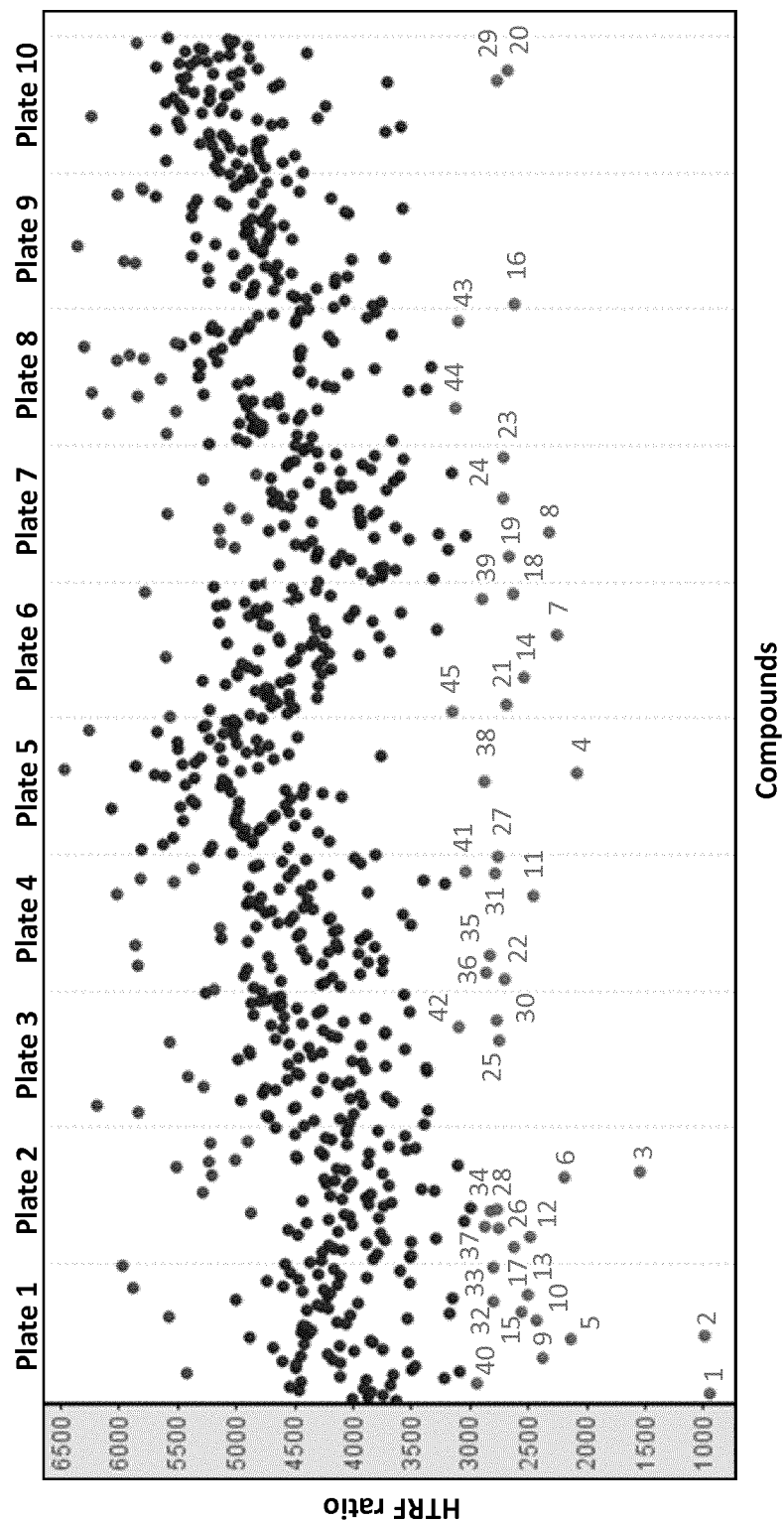
FIG. 16 shows the result of a single point binary mixture of the floral muguet compound 3-(4-hydroxy-4-methylpentyl)cyclohex-3-ene-1-carbaldehyde, 4-(4-hydroxy-4-methylpentyl)cyclohex-3-ene-1-carbaldehyde or a mixture thereof (sold under the tradename LYRAL®, hereinafter referred to as "LYRAL®") and perfumery raw materials screening for OR10J5 LYRAL®-induced activity enhancement.
Figure 17B:
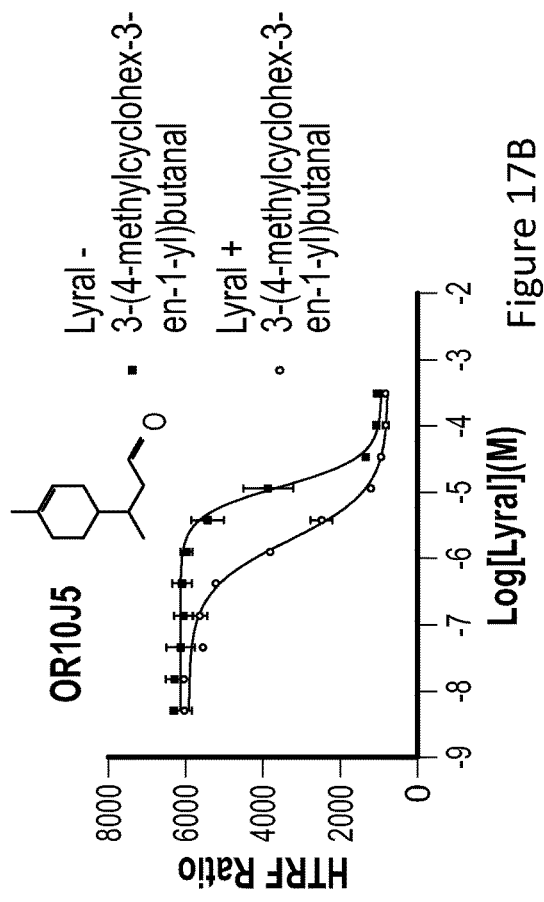
FIG. 17 shows the distinct enhancement levels obtained on OR10J5 LYRAL®-induced activation with a) heliopropanal, b) 3-(4-methylcyclohex-3-en-1-yl)butanal, c) heliotropine and d) cyclomethylene citronellol, and the absence of enhancement for the latter two compounds.
Figure 17D:
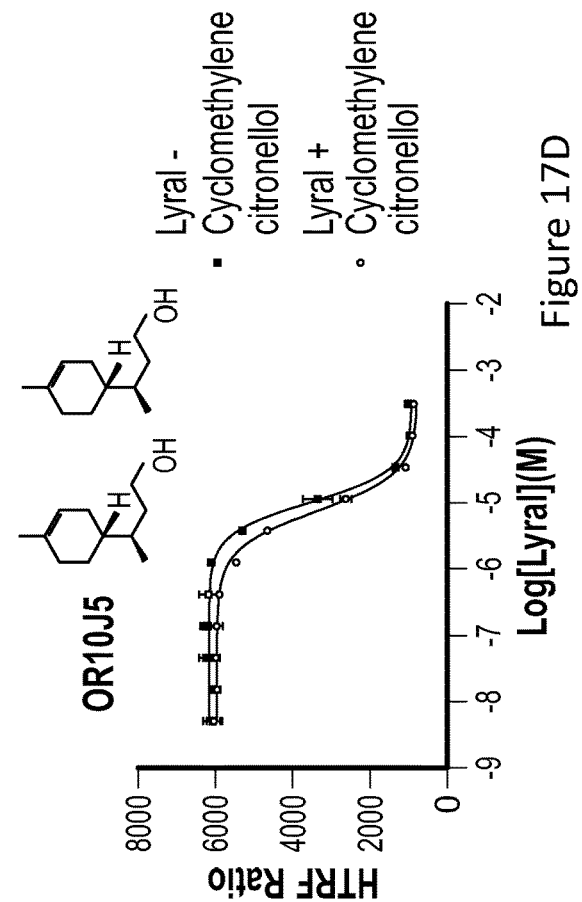
Figure 17A:
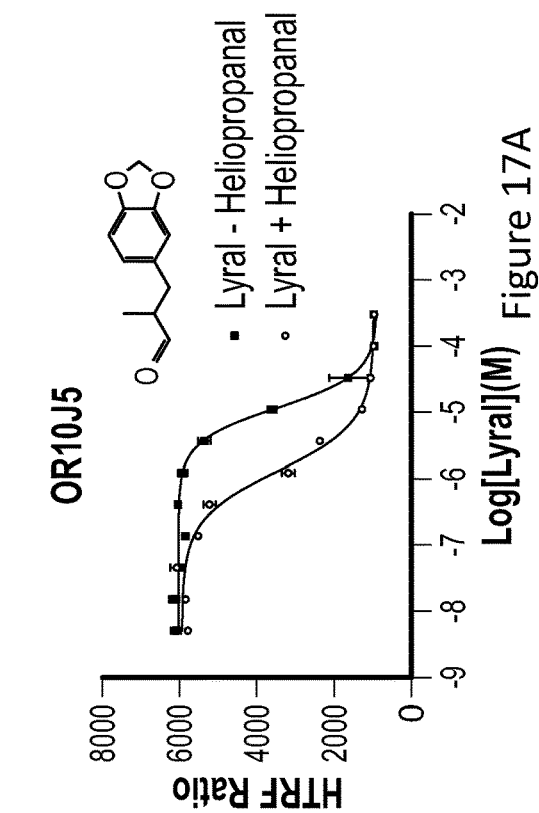
Figure 17C:
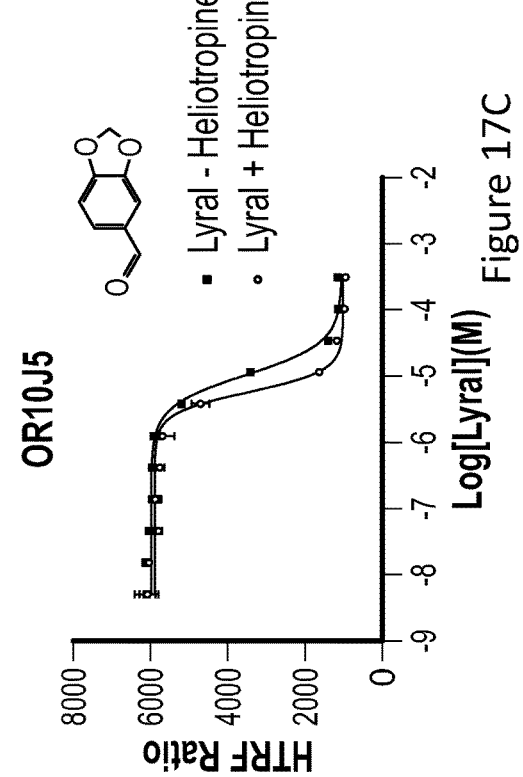

800 binary mixtures were created by mixing a LYRAL® stock solution with a stock solution of each test compound to a final concentration 4.6 and 300 µM, respectively. Stock solutions were made of compounds dissolved in pure DMSO. Each mixture was presented to a cell line expressing the OR10J5 olfactory receptor. The final concentration of DMSO in each binary mixture was 0.1%, and had no visible effect on the cells (see FIG. 16).

The resulting activation was then measured and compared to LYRAL® alone (defining the baseline of the enhancement assay). The quality of the HTS process was determined and the window variability and signal reliability were assessed by calculating the Z' value of each plate. 45 hits were obtained, eight of which were OR10J5 olfactory receptor agonists (hit no 1, 2, 5, 6, 10, 15, 25 and 34), see Table 4. These OR10J5 olfactory receptor agonists further confirmed that the dynamic range of the assay window was sufficient (as the responses recorded were well above baseline) and thus likely sensitive enough to detect even low levels of putative enhancement.

37 candidates, marked as "enhancement" in Table 5 were identified and were tested in two parallel dose-response experiments to confirm the true enhancement properties of the potential candidates. First, a dose-response of each individual candidate was performed to determine if it was an agonist by itself. Second, the same candidate dose-response curve in the presence of $EC_{20}$ LYRAL® concentration (generating 20% activity on OR10J5) was assessed for activity level increase. Molecules that increased the response of the OR10J5 olfactory receptor to LYRAL® beyond $EC_{20}$, but did not display measurable intrinsic activity themselves were considered to be true enhancers and were selected for further studies. From this analysis, 20 molecules were identified that showed enhancement properties. See Table 4.

TABLE 4

| Compounds confirmed as true enhancers of OR10J5 lyral activation. | | | |
|---|---|---|---|
| 1. Octanal | 2. (E)-Dec-2-enal | 3. 2-Phenylpropanal | 4. (E)-But-2-enal |
| 5. 3-Methylbenzaldehyde | 6. 3-(1,3-Benzodioxol-5-yl)-2-methylpropanal | 7. (+−)3-(4-Methyl-3-penten-1-yl)-3-cyclohexene-1-carbaldehyde (A) + (+−)4-(4-Methyl-3-penten-1-yl)-3-cyclohexene-1-carbaldehyde (B) | 8. Heptanal |
| 9. 4-Propan-2-ylbenzaldehyde | 10. (3R)-3,7-Dimethyloct-6-enal | 11. (+)-(3S)-3-[(1R)-4-Methyl-3-cyclohexen-1-yl]butanal (A) + (+)-(3R)-3-[(1R)-4-Methyl-3-cyclohexen-1-yl]butanal | 12. Hexanal |

TABLE 4-continued

Compounds confirmed as true enhancers of OR10J5 lyral activation.

13. 2,6-Dimethylhept-5-enal
14. Benzaldehyde
15. 2-Methyl-3-(4-methylphenyl)propanal
16. 3,5,6-Trimethyl-3-Cyclohexene-1-Carbaldehyde (A) + 2,4,6-Trimethyl-3-Cyclohexene-1-Carbaldehyde (B)
17. 2,4,6-Trimethylcyclohex-3-ene-1-carbaldehyde
18. 4-Ethylbenzaldehyde
19. 6-Methoxy-2,6-dimethylheptanal
20. (E)-Non-2-enal

TABLE 5

Compounds selected from the enhancement screen, numbered by decreasing OR10J5 activity (span).

| | Molecules | Hit Type |
|---|---|---|
| 1 | Lyronol 50 Dipg | Agonist |
| 2 | Lyral | Agonist |
| 3 | Octenal | Enhancement |
| 4 | 2-Decenal | Enhancement |
| 5 | Hydroxycitronellal Synth P Fab | Agonist |

TABLE 5-continued
Compounds selected from the enhancement screen, numbered by decreasing OR10J5 activity (span).
| | Molecules | Hit Type |
|---|---|---|
| 6 | 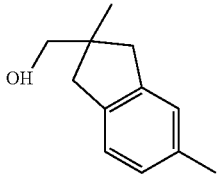<br>Lilyflore | Agonist |
| 7 | 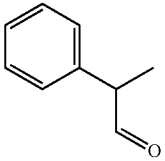<br>Hydrotropic Aldehyde | Enhancement |
| 8 | 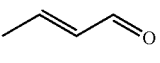<br>E-2-Butenal | Enhancement |
| 9 | 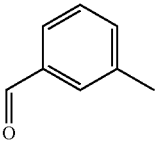<br>m-tolualdehyde | Enhancement |
| 10 | 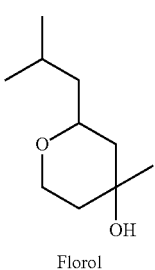<br>Florol | Agonist |
| 11 | 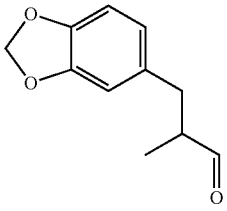<br>Heliopropanal | Enhancement |

TABLE 5-continued

Compounds selected from the enhancement screen, numbered by decreasing OR10J5 activity (span).

| | Molecules | Hit Type |
|---|---|---|
| 12 | Acropal | Enhancement |
| 13 | Base XIV p = Syringa Aldehyde | Enhancement |
| 14 | Farenal HR | Enhancement |
| 15 | Amandolene Pur | Agonist |
| 16 | Heptanal | Enhancement |
| 17 | Cuminaldehyde | Enhancement |
| 18 | Citronella cp | Enhancement |
| 19 | Methyloctylacetaldehyde | Enhancement |

TABLE 5-continued
Compounds selected from the enhancement screen, numbered by decreasing OR10J5 activity (span).
| | Molecules | Hit Type |
|---|---|---|
| 20 | Liminal | Enhancement |
| 21 | Zantryl 50 Dipg | Enhancement |
| 22 | Lemongrass Oil | Enhancement |
| 23 | Cis Nonenal 10 Dipg | Enhancement |
| 24 | Aldehyde C6 Fc | Enhancement |
| 25 | Hydroxycitronellal | Agonist |
| 26 | Precyclemone B | Enhancement |
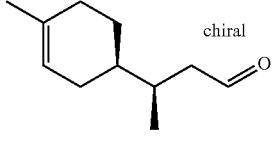
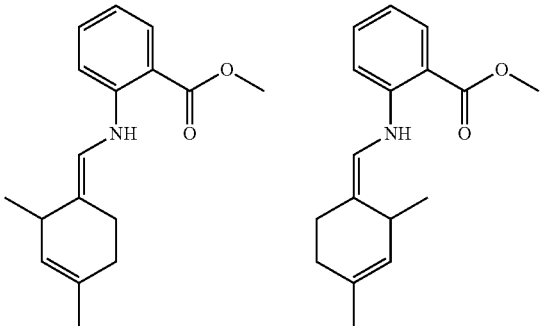
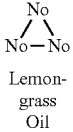
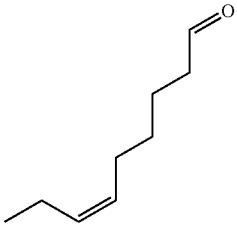
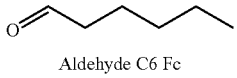
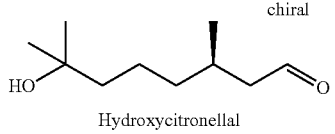
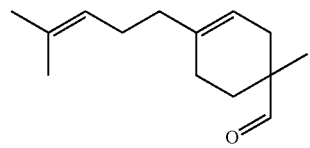

TABLE 5-continued

Compounds selected from the enhancement screen, numbered by decreasing OR10J5 activity (span).

| | Molecules | Hit Type |
|---|---|---|
| 27 | Melonal | Enhancement |
| 28 | Benzaldehyde | Enhancement |
| 29 | Costenal | Enhancement |
| 30 | Neral & Geranial | Enhancement |
| 31 | Citronella Oil Java | Enhancement |
| 32 | E2, E4-Decadienal | Enhancement |
| 33 | Nonanal | Enhancement |
| 34 | Dihydromyrcenol iff | Agonist |
| 35 | Undecalactone Delta | Enhancement |
| 36 | Satinaldehyde | Enhancement |

TABLE 5-continued

Compounds selected from the enhancement screen, numbered by decreasing OR10J5 activity (span).

| | Molecules | Hit Type |
|---|---|---|
| 37 | Heliotropine | Enhancement |
| 38 | Isocyclocitral | Enhancement |
| 39 | Vertonal | Enhancement |
| 40 | Ethyl Maltol | Enhancement |
| 41 | Aldehyde E | Enhancement |
| 42 | Natactone 50 Mip | Enhancement |
| 43 | Methoxymelonal | Enhancement |
| 44 | Nonylenic Aldehyde | Enhancement |

TABLE 5-continued

Compounds selected from the enhancement screen, numbered by decreasing OR10J5 activity (span).

| Molecules | Hit Type |
|---|---|
| 45 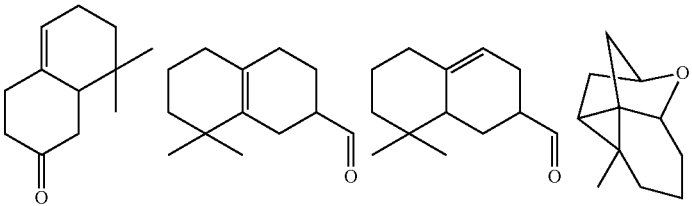 Cyclemone A | Enhancement |

Example 9: Characterization of OR10J5 Activity Enhancement Specificity

LYRAL® enhancement specificity was tested on compounds that were structurally similar to enhancers identified. Dose response curves to LYRAL® were obtained in the presence of a steady concentration of a test compound and compared to a dose-response curve of LYRAL® alone. The resulting enhancement was quantified by means of $EC_{50}$-fold shift (potency increase) and the efficacy span ratio (efficacy increase).

The $EC_{50}$-fold shift was obtained by dividing the $EC_{50}$ of LYRAL®+compound by the reference $EC_{50}$ of LYRAL® alone. The span ratio was obtained by dividing the span of LYRAL®+compound by the reference span of LYRAL® alone.

FIG. 17 shows the distinct enhancement levels obtained with a) heliopropanal and b) 3-(4-methylcyclohex-3-en-1-yl)butanal, and the absence of enhancement with c) heliotropine and d) cyclomethylene citronellol for OR10J5. OR10J5 activation by LYRAL® was specifically enhanced by heliopropanal and 3-(4-methylcyclohex-3-en-1-yl)butanal, but not by structurally related compounds as indicated by the corresponding fold shifts: a 9.2 and 6.7 fold shift for heliopropanal and 3-(4-methylcyclohex-3-en-1-yl)butanal respectively, versus a 1.8 and 1.3 fold shift for heliotropine and cylcomethylene citronellol, respectively.

FIG. 18 shows the distinct enhancement levels obtained with heliopropanal and 3-(4-methylcyclohex-3-en-1-yl)butanal, and the absence of enhancement with heliotropine and cyclomethylene citronellol for the mouse ortholog of OR10J5, Olfr16. Olfr16 activation by LYRAL® was specifically enhanced by heliopropanal and 3-(4-methylcyclohex-3-en-1-yl)butanal, but not by structurally related compounds as indicated by the corresponding fold shifts: a 5 fold shift for both heliopropanal and 3-(4-methylcyclohex-3-en-1-yl)butanal, versus a 1.5 and 1.1 fold shift for heliotropine and cylcomethylene citronellol, respectively. These results indicate enhancement of other mammalian olfactory receptors.

Example 10: Floral Muguet Compound Enhancers Act as Positive Allosteric Modulators (PAM) to Enhance OR10J5 Olfactory Receptor Activity Functional dose-response experiments were performed to reveal the allosteric nature of the interaction between heliopropanal, 3-(4-methylcyclohex-3-en-1-yl)butanal, melonal and heptanal and OR10J5. The level of enhancement of OR10J5's activation was evaluated at distinct concentrations of each enhancer. Using the same cell-based assay described earlier, dose response curves of OR10J5 to LYRAL® in the presence of serial concentrations of the enhancers spanning from 0 to 600 µM were performed, see FIG. 19. The curves were obtained by applying the simplified Allosteric EC50 shift effect equation (available in Prism7) derived from the ternary complex interaction model. The enhancement levels recorded were not linearly dependent on the concentration of the enhancer, and the following key parameters values for $\alpha$ (the cooperativity factor) and $K_B$ (the equilibrium dissociation constant of the enhancer) were obtained from the model for each enhancer: heliopropanal, $\alpha=6.3$ and $K_B=10$ µM; 3-(4-methylcyclohex-3-en-1-yl)butanal, $\alpha=7.5$ and $K_B=15$ µM; melonal, $\alpha=4.1$ and $K_B=16$ µM; and heptanal; $\alpha=3.2$ and $K_B=51$ µM. $\alpha>1$ is indicative of positive allosteric modulation.

Example 11: Human Sensitivity to LYRAL® is Increased in the Presence of an Enhancer Sensitivity of human individuals to LYRAL® was evaluated by performing an odor detection threshold (ODT) test. The ODT test consisted of identifying the concentration for which 50%, preferably 66%, of the panelists are able to determine which of three containers contains the target compound LYRAL® in a series of forced-choice triangle tests. Two tests were performed to calculate the ODT in mixtures containing LYRAL® plus a perceivable background odor of chemically similar molecules a) the enhancer, 3-(4-methylcyclohex-3-en-1-yl)butanal and b) the non-enhancing volatile compound, Cyclomethylene citronellol. These two molecules are chemically similar.

Figure 20:
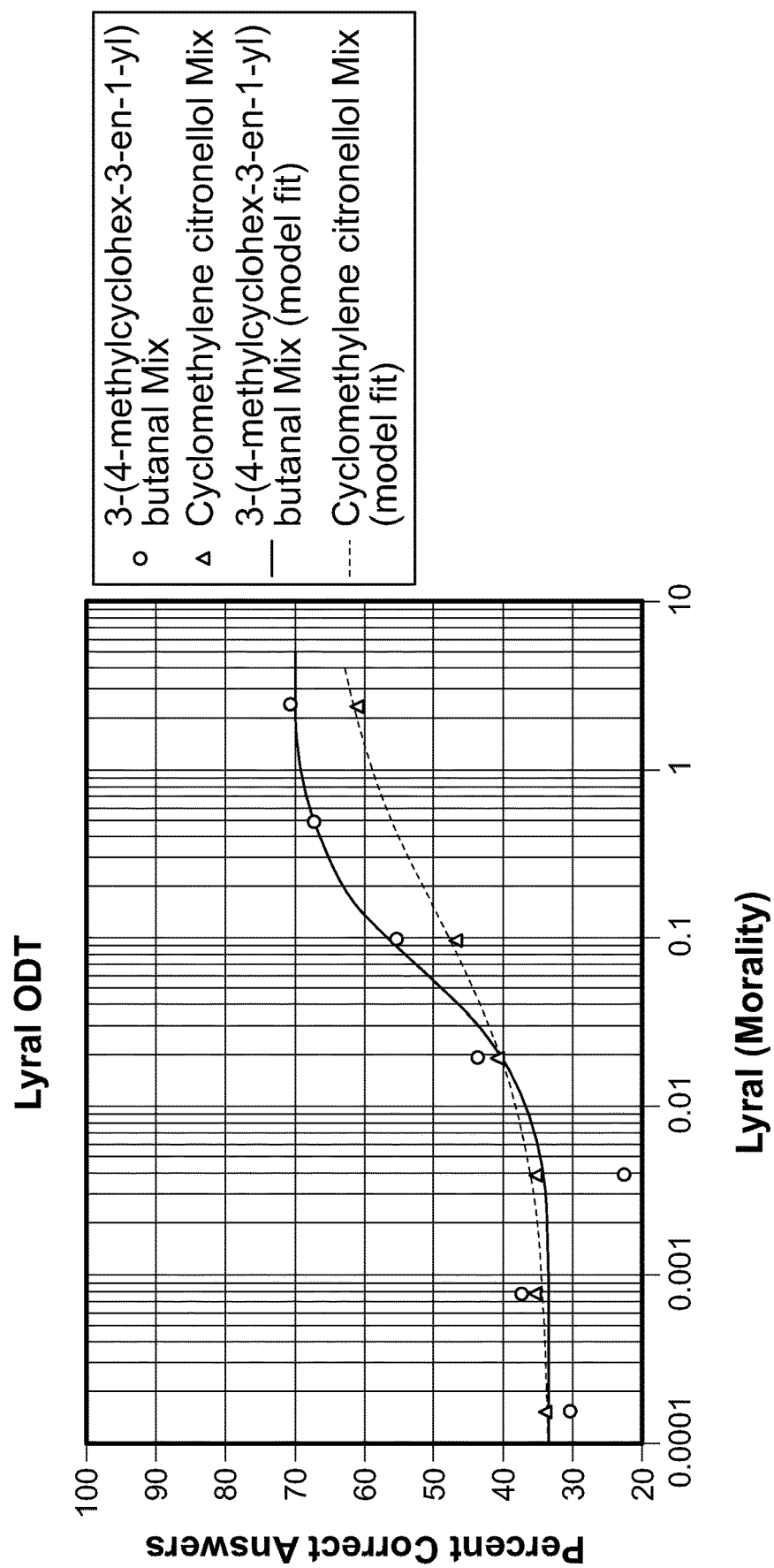
FIG. 20 shows human panelists more sensitive to LYRAL® in the presence of an enhancer compared to a non-enhancing compound.

28 panelists were given a series of triangle tests with increasing concentrations of LYRAL® in the presence of 3-(4-methylcyclohex-3-en-1-yl)butanal at a concentration of 0.1%. Within each triangle test, the three samples contained 3-(4-methylcyclohex-3-en-1-yl)butanal at 0.1% and one sample also contained LYRAL®. 28 panelists were given a series of triangle tests with increasing concentration of Lyral® in the presence of Cyclomethylene citronellol at a concentration of 7%. Within each triangle test, the three samples contained Cyclomethylene citronellol at 7% and one sample also contained LYRAL®. In each triangle test, the panelists were asked to identify the one sample that was different from the other two samples. Corresponding results are shown in FIG. 20.

Figure 21:
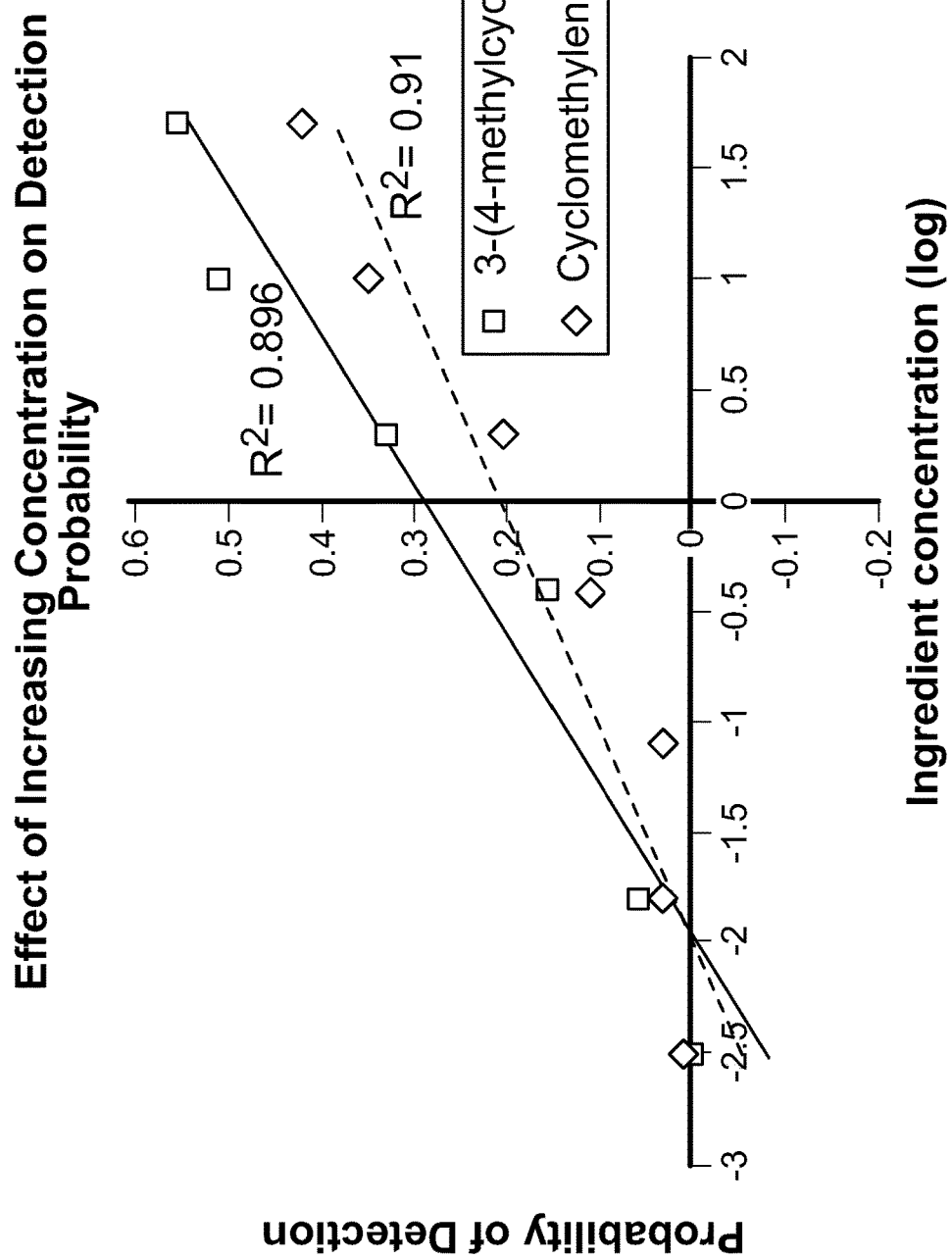
FIG. 21 shows human panelists increased LYRAL® detection as a function of enhancer concentration compared to non-enhancing compound.

The proportion of correct responses was adjusted to account for the probability of guessing using Abbott's formula frequently used in the field (Lawless, 2010). A linear regression, with Material (Enhancer versus Neutral compound) and log-transformed Concentration Level as explanatory variables, and proportion of correct responses as a response variable, yielded a significant main effect of Material (p=0.03) and a marginally significant interaction (p=0.052), indicating that with increasing concentration, proportion of correct responses increased at a higher rate when LYRAL® was mixed with the enhancer (versus neutral compound. See FIG. 21).

Example 12: OR10J5 Activity Enhancement is Independent of OR10J5 Agonists

OR10J5 activity enhancement was tested with an additional agonist and with one of the test compounds and conditions described in the Examples above. Dose response curves to (+−)-2,5-dimethyl-2-indanmethanol was obtained in the presence of a steady concentration of the test compound and compared to a dose-response curve of the agonist alone. The resulting enhancement was quantified by means of $EC_{50}$-fold shift (potency increase) and the efficacy span ratio (efficacy increase) as described above.

Figure 22A:
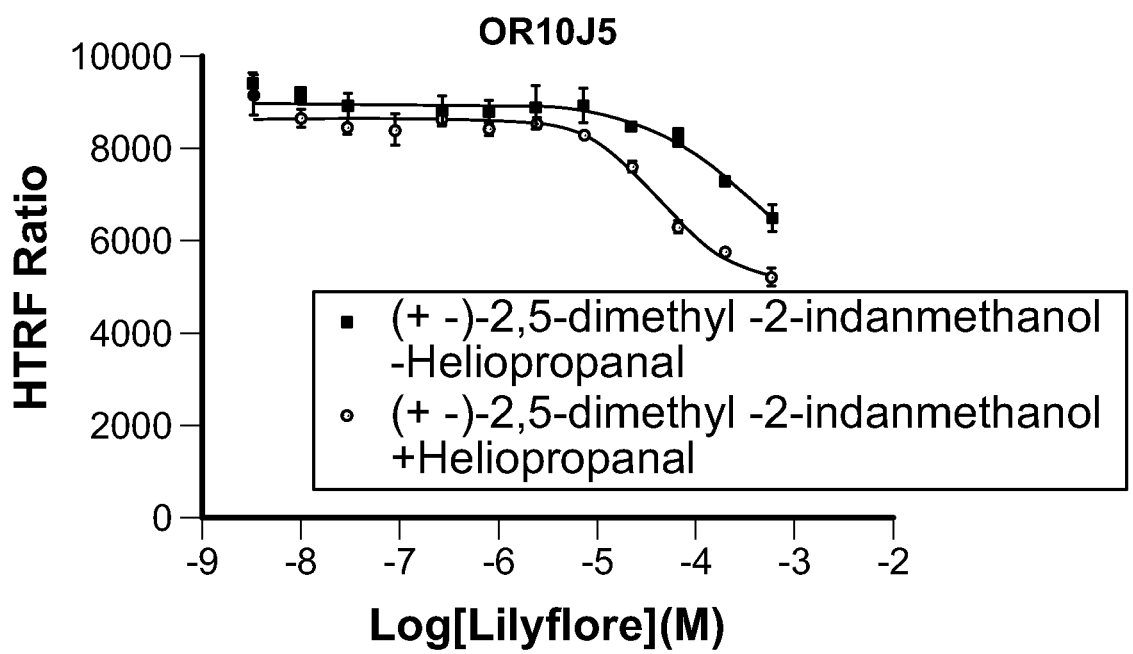
FIG. 22 shows the distinct enhancement levels obtained on OR10J5 (+−)-2,5-dimethyl-2-indanmethanol-induced activation with a) heliopropanal, and b) heliotropine, and the absence of enhancement for the latter compound.
Figure 22B:
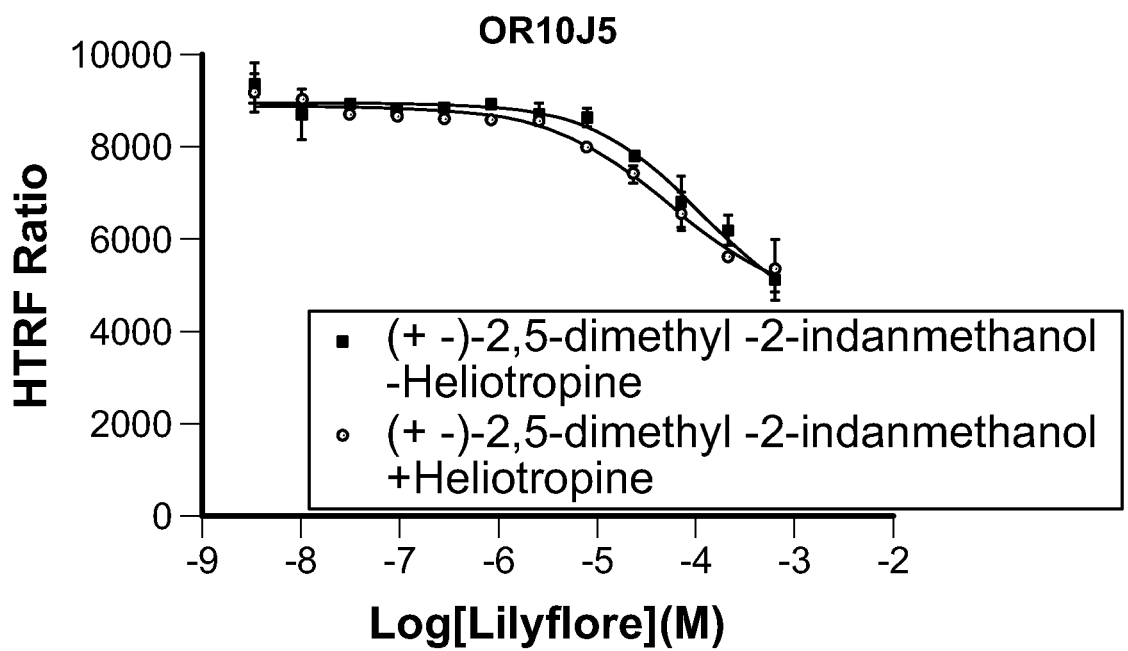

FIG. 22 shows the distinct enhancement levels obtained with a) heliopropanal, and the absence of enhancement with b) heliotropine OR10J5 activation by (+−)-2,5-dimethyl-2-indanmethanol was specifically enhanced by heliopropanal, but not by the structurally related compound as indicated by the corresponding fold shifts: a 8.6 and 2.0 fold shift for heliopropanal and heliotropine, respectively.

This demonstrates that the test compound is specifically enhancing the activity of OR10J5 independently of the nature of the agonist (activating compound). In this particular case (+−)-2,5-dimethyl-2-indanmethanol, is a partial agonist of OR10J5 and yet was enhanced by heliopropanal which led to a 1.7 fold efficacy increase within the dynamic range of the dose response in addition to the potency increase (see FIG. 22a). This further indicated that the enhancement was mediated through a receptor binding event and not likely mediated by receptor-independent effects such as on the assay cells themselves.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A high-throughput assay system for identifying one or more compounds from a group of compounds wherein the one or more compounds positively modulates the activity of an olfactory receptor induced by an agonist odorant compound, comprising:
   a) one or more isolated cells, each cell expressing one mammalian olfactory receptor, wherein the one or more cells comprises a target olfactory receptor that is activated by one or more odorant,
   b) a first compound that binds to the olfactory receptor and that activates the olfactory receptor, and
   c) at least one second compound that binds to the receptor non-competitively relative to the first compound and that enhances the activity of the receptor exposed to the first compound when compared to the activity of the receptor exposed to the first compound in the absence of the second compound,
   wherein the olfactory receptor comprises a polypeptide that
   comprises an amino acid sequence having at least 95% sequence identity to SEQ ID NO: 2, 4, 6, or 8; or
   is encoded by a nucleic acid molecule comprising a nucleotide sequence having at least 95% sequence identity to SEQ ID NO: 1, 3, 5, or 7, or the reverse complement thereof,
   wherein the first compound is an agonist odorant compound of the olfactory receptor,
   wherein the first compound is a musk or a floral muguet compound,
   wherein the first compound and the second compound are different compounds,
   wherein the second compound is not an agonist of the receptor,
   wherein the second compound has the structure:

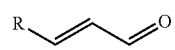

Formula (I)

in the form of any one of its stereoisomers or a mixture thereof,
   wherein R represents a $C_{3-11}$ linear alkyl group optionally substituted by a $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, or
   wherein the second compound is at least one positive allosteric modulator selected from the group consisting of (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof, 4-ethylbenzaldehyde; 6-methoxy-2,6-dimethylheptanal; (E)-non-2-enal; and combinations thereof,
   wherein the second compound is a positive allosteric modulating compound, and
   wherein the activity of the receptor is synergistically enhanced by the combination of the first compound and the second compound.

2. The assay system of claim 1, wherein the at least one second compound is selected from a pool of compounds based on structure-activity relationship (SAR) analysis.

3. The assay system of claim 1, wherein prior to step a) the one or more cells were transformed to express the target olfactory receptor.

4. The assay system of claim 1, wherein the polypeptide
a) comprises an amino acid sequence having at least 98%, 99% or 100% sequence identity to SEQ ID NO: 2, 4, 6, or 8; or
b) is encoded by a nucleic acid molecule comprising a nucleotide sequence having at least 98%, 99% or 100% sequence identity to SEQ ID NO: 1, 3, 5, or 7, or the reverse complement thereof.

5. The assay system of claim 1, wherein the mammalian olfactory receptor is a mouse olfactory receptor or a human olfactory receptor.

6. The assay system of claim 1, wherein the first compound comprises a musk compound and the olfactory receptor comprises a polypeptide that
a) comprises an amino acid sequence having at least 95% sequence identity to SEQ ID NO: 2 or 6; or
b) is encoded by a nucleic acid molecule comprising a nucleotide sequence having at least 95% sequence identity to SEQ ID NO: 1 or 5, or the reverse complement thereof.

7. The assay system of claim 1, wherein the musk compound comprises a macrocyclic ketone or a nitromusk compound.

8. The assay system of claim 1, wherein the first compound comprises a floral muguet compound and the olfactory receptor comprises a polypeptide that
a) comprises an amino acid sequence having at least 95% sequence identity to SEQ ID NO: 4 or 8; or
b) is encoded by a nucleic acid molecule comprising a nucleotide sequence having at least 95% sequence identity to SEQ ID NO: 3 or 7, or the reverse complement thereof.

9. The assay system of claim 1, wherein the modulated activity comprises
a) modulating the binding affinity of the first compound to the orthosteric site,
b) modulating the binding activation efficacy of the first compound to the orthosteric site, or
c) modulating the G-protein binding site.

10. A method for identifying at least one positive allosteric modulating compound that enhances the activity of an olfactory receptor in the presence of an agonist of the receptor, comprising
a) providing one or more isolated cells, each cell expressing one mammalian olfactory receptor,
b) exposing the one or more cells to a first compound that activates the olfactory receptor,
c) exposing the one or more cells to one or more test compound, and
d) selecting at least one second compound from the one or more test compounds when the at least one second compound in combination with the first compound has a synergistic effect on the receptor activity as a positive allosteric modulating compound;
wherein the olfactory receptor comprises a polypeptide that
comprises an amino acid sequence having at least 95% sequence identity to SEQ ID NO: 2, 4, 6, or 8; or
is encoded by a nucleic acid molecule comprising a nucleotide sequence having at least 95% sequence identity to SEQ ID NO: 1, 3, 5, or 7, or the reverse complement thereof,
wherein the first compound is an agonist odorant compound of the olfactory receptor,
wherein the first compound is a musk or a floral muguet compound,
wherein the second compound has the structure:

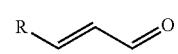

Formula (I)

in the form of any one of its stereoisomers or a mixture thereof,
wherein R represents a $C_{3-11}$ linear alkyl group optionally substituted by a $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, or
wherein the second compound is at least one positive allosteric modulator selected from the group consisting of (E)-dec-2-enal; 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof; hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof, 4-ethylbenzaldehyde; 6-methoxy-2,6-dimethylheptanal; (E)-non-2-enal; and combinations thereof,
wherein the first compound and the second compound are different compounds, and
wherein the second compound is not an agonist of the receptor.

11. The method of claim 10, wherein the activation of the olfactory receptor to the first compound is measured by measuring the response of said olfactory receptor in the presence and absence of the first compound.

12. The method of claim 10, wherein the at least one second compound is selected from one or more test compounds based on structure-activity relationship (SAR) analysis.

13. The method of claim 10, wherein the second compound binds to a site on the olfactory receptor distinct from the site where the first compound binds.

14. The method of claim 10, wherein prior to step a) the one or more cells is transformed to express the olfactory receptor.

15. The method of claim 10, wherein the olfactory receptor is heterologous to the one or more cells.

16. The method of claim 10, wherein the cell is selected from the group consisting of HEK293, CHO, Xenopus oocytes, COS, insect, yeast and cells derived from the olfactory placode.

17. A method for identifying a compound that enhances the activity of an olfactory receptor induced by an agonist odorant compound comprising:
(i) screening one or more compounds in a binding assay in the presence of the agonist odorant compound;
(ii) selecting one or more of the compounds screened that specifically enhances the specific binding or the effect of the binding of an agonist odorant compound to a mammalian olfactory receptor; and
(iii) identifying compounds that potentially modulate the perception of the agonist odorant compound based on their enhancement of the specific binding or the effect of the binding of the agonist odorant compound to the olfactory receptor,
wherein the olfactory receptor comprises a polypeptide that
comprises an amino acid sequence having at least 95% sequence identity to SEQ ID NO: 2, 4, 6, or 8; or
is encoded by a nucleic acid molecule comprising a nucleotide sequence having at least 95% sequence identity to SEQ ID NO: 1, 3, 5, or 7, or the reverse complement thereof,
wherein the agonist odorant compound is a musk or a floral muguet compound,
wherein the compound has the structure:

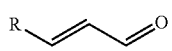

Formula (I)

in the form of any one of its stereoisomers or a mixture thereof,
wherein R represents a $C_{3-11}$ linear alkyl group optionally substituted by a $C_{1-4}$ alkyl carboxylester group or a hydroxyl group, a $C_{4-11}$ branched alkyl group optionally substituted by a $C_{1-3}$ alkoxy group, a $C_{6-12}$ linear or branched alkenyl or alkadienyl group, a phenyl group substituted by one or two $C_{1-3}$ alkyl groups, a $C_{5-8}$ alicyclic alkenyl group or a benzyloxymethyl group, or
wherein the compound is at least one positive allosteric modulator selected from the group consisting of (E)-dec-2-enal, 2-phenylpropanal; (E)-but-2-enal; 3-methylbenzaldehyde; 3-(1,3-benzodioxol-5-yl)-2-methylpropanal; (+−)-3-(4-methyl-3-penten-1-yl)-3-cyclohexene-1-carbaldehyde, (+−)-4-(4-methyl-3-penten-1-yl)-3-cyclohexene-1-carbaldehyde, and mixtures thereof; heptanal, 4-Propan-2-ylbenzaldehyde; (3R)-3,7-dimethyloct-6-enal; (+)-(3S)-3-[(1R)-4-methyl-3-cyclohexen-1-yl]butanal, (+)-(3R)-3-[(1R)-4-methyl-3-cyclohexen-1-yl]butanal, and mixtures thereof, hexanal; 2,6-dimethylhept-5-enal; benzaldehyde; 2-methyl-3-(4-methylphenyl)propanal; 3,5,6-trimethyl-3-cyclohexene-1-carbaldehyde, 2,4,6-trimethyl-3-cyclohexene-1-carbaldehyde, and mixtures thereof, 4-ethylbenzaldehyde; 6-methoxy-2,6-dimethylheptanal; (E)-non-2-enal; and combinations thereof.

18. The method of claim 17, wherein the mammalian olfactory receptor is a mouse olfactory receptor or a human olfactory receptor.

19. The method of claim 17, wherein the polypeptide
a) comprises an amino acid sequence having at least 98%, 99% or 100% sequence identity to SEQ ID NO: 2, 4, 6, or 8; or
b) is encoded by a nucleic acid molecule comprising a nucleotide sequence having at least 98%, 99% or 100% sequence identity to SEQ ID NO: 1, 3, 5, or 7, or the reverse complement thereof.

20. The method of claim 17, wherein the agonist odorant compound is a musk compound and the olfactory receptor comprises a polypeptide that
a) comprises an amino acid sequence having at least 95% sequence identity to SEQ ID NO: 2 or 6; or
b) is encoded by a nucleic acid molecule comprising a nucleotide sequence having at least 95% sequence identity to SEQ ID NO: 1 or 5, or the reverse complement thereof.

21. The method of claim 20, wherein the musk compound is a macrocyclic ketone or a nitromusk compound.

22. The method of claim 17, wherein the agonist odorant compound is a floral muguet compound and the olfactory receptor comprises a polypeptide that
a) comprises an amino acid sequence having at least 95% sequence identity to SEQ ID NO: 4 or 8; or
b) is encoded by a nucleic acid molecule comprising a nucleotide sequence having at least 95% sequence identity to SEQ ID NO: 3 or 7, or the reverse complement thereof.

23. The method of claim 17, wherein the modulated activity comprises
a) modulating the binding affinity of the agonist odorant compound to the orthosteric site,
b) modulating the binding activation efficacy of the compound to the orthosteric site, or
c) modulating the G-protein binding site.

24. The method of claim 17, wherein the enhancement of the effect of the binding of the agonist odorant compound to the olfactory receptor comprises enhancing the potency or efficacy of the activity of the receptor compared to the activity of the receptor in the absence of the selected compound.

25. The method of claim 17, wherein the compound of Formula (I) is selected from the group consisting of: (E,E)-2,4-decadienal, (E)-2-undecenal, (E,E)-2,4-nonadienal, (E)-2-tridecenal, (2E)-2-dodecenal, (2E,6Z)-2,6-nonadienal, (E,E)-2,6-nonadienal, (2E)-2,4-undecadienal, (2E)-2,4-dodecadienal, (E)-2-nonenal, (2E,4E,7Z)-decatrienal, (Z)-2-decenal, (E)-2-octenal, (E)-2-decenal, (Z)-4-(benzyloxy)but-2-enal, (E)-4-(benzyloxy)but-2-enal, (E)-4-cyclohexylidenebut-2-enal, (2E)-3-(4-methylphenyl)-2-propenal, (2E,5E)-6,10-dimethyl-2,5,9-undecatrienal, (2E)-7,8-dimethyl-2,7-nonadienal, methyl(5E)-7-oxo-5-heptenoate, (2E)-7-methyl-2,6-octadienal, (2E)-6,6-dimethyl-2-heptenal, (+−)-(2E)-5,9-dimethyl-2,8-decadienal, (E)-2-tetradecenal, (E)-8-methoxy-4,8-dimethylnon-2-enal, and combinations thereof.

26. The method of claim 17, wherein the one or more selected compound is selected based on structure-activity relationship (SAR) analysis specifically designed to identify the chemical determinants of putative enhancement.

27. The method of claim 17, wherein the screening comprises calculating an activation window to measure the synergistic effect enhancement at EC05-50.

* * * * *